US007491507B2

(12) United States Patent
Flambard

(10) Patent No.: US 7,491,507 B2
(45) Date of Patent: Feb. 17, 2009

(54) PROCESS FOR PREPARING PEPTIDES WITH ANTI-HYPERTENSIVE PROPERTIES

(75) Inventor: Bénédicte Flambard, Frederiksberg (DK)

(73) Assignee: Chr. Hansen A/S, Horsholm (DK)

( * ) Notice: Subject to any disclaimer, the term of this patent is extended or adjusted under 35 U.S.C. 154(b) by 20 days.

(21) Appl. No.: 10/637,544

(22) Filed: Aug. 11, 2003

(65) Prior Publication Data

US 2004/0106171 A1    Jun. 3, 2004

Related U.S. Application Data

(60) Provisional application No. 60/404,396, filed on Aug. 20, 2002.

(30) Foreign Application Priority Data

Aug. 9, 2002    (DK) ............................. 2002 01194
Mar. 11, 2003   (DK) ............................. 2003 00361

(51) Int. Cl.
    *C12P 1/00*    (2006.01)
(52) U.S. Cl. ........................................ 435/41
(58) Field of Classification Search ............... None
    See application file for complete search history.

(56) References Cited

FOREIGN PATENT DOCUMENTS

| EP | 0058074 B1 | 8/1982 |
| EP | 0 737 690 | * 10/1996 |
| EP | 0821968 A2 | 2/1998 |
| EP | 1016709 A1 | 7/2000 |
| WO | 01/32836 A1 | 5/2001 |
| WO | WO 01/32836 A1 | 5/2001 |
| WO | WO 01/32905 A1 | 5/2001 |

OTHER PUBLICATIONS

Maeno et al., Identification of an antihypertensive peptide from casein hydrolysate produced by a proteinase from *Lactobacillus helveticus* CP790. J Dairy Sci. Aug. 1996;79(8):1316-21.*
Yamamoto et al., Purification and characterization of an antihypertensive peptide from a yogurt-like product fermented by *Lactobacillus helveticus* CPN4. J Dairy Sci. Jul. 1999(b);82(7):1388-93.*
GenEmbl database Accession No. CQ759881 Mar. 3, 2004 Pridmore et al. Alignment with SEQ ID No. 1.*
Guo et al, Protein tolerance to random amino acid change. Proc Natl Acad Sci U S A. Jun. 22, 2004;101(25):9205-9210. Epub Jun. 14, 2004.*
Jeffrey A. Pederson et al., "Genetic characterization of a cell envelope-associated proteinase from *Lactobacillus helveticus* CNRZ32," Journal of Bacteriology, Aug. 1999, pp. 4592-4597, vol. 181, No. 15.
Naoyuki Yamamoto et al., "Molecular cloning and sequence analysis of a gene encoding an extracellular proteinase from *Lactobacillus helveticus* CP790," Biosci. Biotechnol. Biochem. 64 (6), pp. 1217-1222, 2000.

Anders Fuglsang et al., "Cardiovascular effects of fermented milk containing angiotensin-converting enzyme inhibitors evaluated in permanently catheterized, Spontaneously hypertensive rats," Applied and Environmental Microbiology, Jul. 2002, pp. 3566-3569.
Gobbetti et al., "Production of Angiontensin-I-Converting-Enzyme-Inhibitory Peptides in Fermented Milks Started by *Lactobacillus delbrueckii* subsp. *bulgaricus* SS1 and *Lactococcus lactis* subsp. *cremoris* FT4," Applied and Environmental Microbiology, Sep. 2000, p. 3898-3904, vol. 66, No. 9, American Society for Microbiology.
Lowry et al., "Protein Measurement with the Folin Phenol Reagent," J. Biol. Chem, 1951, 193:265-275.
Yamamoto et al., "Antihypertensive Effect of the Peptides Derived from Casein by an Extracellular Proteinase from *Lactobacillus helveticus* CP790," 1994, J. Dairy Sci., 77:917-922.
Shin et al., "His-His-Leu, an Angiotensin I Converting Enzyme Inhibitory Peptide Derived from Korean Soybean Paste, Exerts Antihypertensive Activity in Vivo," J. Agric. Food Chem., 2001, 49, pp. 3004-3009, American Chemical Society.
Flambard, "Role of bacterial cell wall proteinase in antihypertension," Sciences Des Aliments, 22(2002) pp. 209-222.
International Search Report dated Dec. 3, 2003 for PCT/DK03/00522.
Fitzgerald, et al., "Milk protein-derived peptide inhibitors of angiotensin-I-converting enzyme," British Journal of Nutrition 84:S33-S37 (Suppl. I 2002).
Gobetti, et al., "Production to Angiotensin-I-Converting-Enzyme-Inhibitory Peptides in Fermented Milks Started by *Lactobacillus delbrueckii* subsp. *bulgaricus* SS1 and *Lactococcus lactis* subsp. *cremoris* FT4" Applied and Environmental Microbiology, vol. 66, No. 9, p. 3898-3904 (Sep. 2000).
Nakamura, et al., "Antihypertensive effect of sour milk and peptides isolated from it that are inhibitors toangiotensin-I-converting enzyme," J. Dairy Sci. 78: 1253-1257 (1995).
Yamamoto, et al., "Antihypertensive effect of the peptides derived from casein by an extracellular proteinase from *Lactobacillus helveticus* CP790," J. Dairy Sci. 77:917-922 (1994).
Meisel, et al., "Bioactive peptides encrypted in milk proteins: proteolytic activation and thropho-functional properties", Antonie van Leeuwenhoek 76: 207-215 (1999).
Law, et al., Proteolytic enzymes of lactic acid bacteria, Int., Dairy Journal 7(1):1-11 (1997).
Yin, et al., "Effect of lactic acid bacterial fermentation on the characteristics of minced mackerel," Journal of Food Science 67(2):786-792 (2002).
Flambard, " Role of bacterial cell wall proteinase in antihypertension, " Sciences Des Aliments 22:209-222 (2002).

(Continued)

*Primary Examiner*—Sheridan Swope
(74) *Attorney, Agent, or Firm*—Hunton & Williams

(57)    ABSTRACT

Use of a lactic acid bacterium comprising a cell wall proteinase of around 200 kDa to prepare peptides with anti-hypertensive properties and a method for obtaining such a lactic acid bacterium.

4 Claims, 1 Drawing Sheet

OTHER PUBLICATIONS

Figure 1:
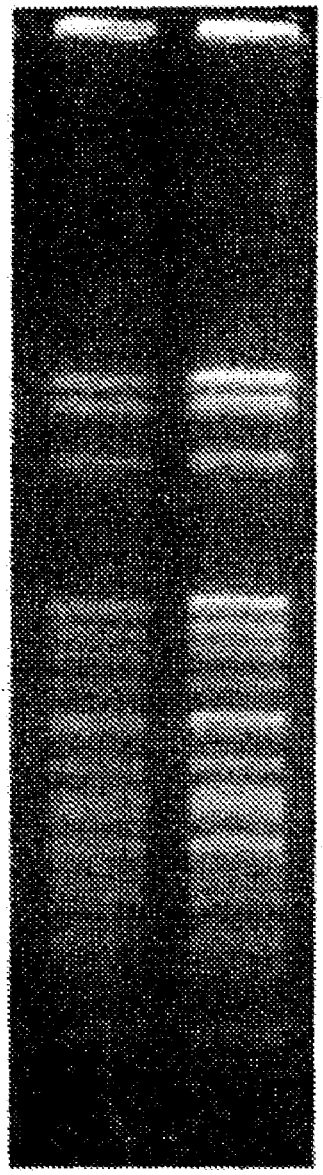

Shin, et al., "His-His-Leu, an angiotensin I converting Enzyme inhibitory peptide derived from Korean soybean paste, exerts antihypertensive activty in vivo," J.Agric. Food Chem. 49:3004-3009 (2001).

International Search Report dated Dec. 3, 2002 for International Application No. PCT/DK03/00522.

International Search Report dated Aug. 31, 2004 for International Application No. PCT/DK2004/000239.

Altschul, et al., "Basic Local Alignment Search Tool" J. Mol. Biol. 215:403-410 (1990).

McGinnis, et al., "Blast: at the core of a powerful and diverse set of sequence analysis tools," Nucleic Acids Research 32:W20-W25 (Web Server issue 2004).

Maniatis, et al., "Molecular Cloning: A laboratory manual," (Cold Spring Harbor Laboratories, 2nd ed., vol. 3 1989).

Ausbel, et al., Current protocols in molecular biology, (John Wiley and Sons 1995).

Teo, et al., Circulation 102:1748-1754 (2000).

Marmur, Journal of Molecular Biology 3:208-218 (1961).

\* cited by examiner

PROCESS FOR PREPARING PEPTIDES WITH ANTI-HYPERTENSIVE PROPERTIES

CROSS-REFERENCE TO RELATED APPLICATIONS

I claim the benefit of the filing dates of the following patent applications: Denmark Application PA 2003 00361, filed Mar. 11, 2003; Denmark Application PA 2002 01194, filed Aug. 9, 2002; and U.S. Provisional Application 60/404,396, filed Aug. 20, 2002.

FIELD OF INVENTION

The present invention relates to use of a lactic acid bacterium comprising a cell wall proteinase of around 200 kDa to prepare peptides with anti-hypertensive properties and a method for obtaining such a lactic acid bacterium.

DESCRIPTION OF THE BACKGROUND ART

Hypertension (high blood pressure) has been reported to be one of the most important risk factors associated with heart attack in industrialized countries. Hypertension is frequently treated with drugs that strongly inhibit the angiotensin-converting enzyme (ACE). The prevention of high blood pressure in the early stage of the development of the disease, can be an alternative, to the treatment of hypertension with drugs. A large number of food-derived bioactive compounds are currently considered as beneficial for general well being or as health promoting.

In the regulation of blood pressure, angiotensin I-converting enzyme (ACE) plays an important role. ACE acts to increase the blood pressure. In the renin-angiotensin system, ACE converts angiotensin-I to angiotensin-II by hydrolysing His-Leu from its C-terminal. Angiotensin II exhibits a strong vasoconstricting action. Additionally, in the kinin kallikrein system, ACE deactivates bradykinin, which aids vasodilation. ACE inhibitors are therefore useful in reducing blood pressure. Currently several ACE inhibitors already exist. The first reported ACE inhibitors were naturally occurring peptides found in snake venom. Since then, many other ACE inhibitors have also been discovered.

It is known that milk fermented by lactic acid bacteria (LAB) may produce anti-hypertensive effects due to the liberation of peptides from casein in the milk by the proteolytic activity of the lactic acid bacteria. The peptides act as ACE inhibitors.

The article of the company Calpis Food Industry [Yamamoto et al (1994, *J. Dairy Sci.*, 77: 917-922)] discloses that milk fermentation by a *Lactobacillus helveticus* CP790 strain produced anti-hypertensive effects due to the liberation of peptides from casein in the milk by the proteolytic activity of *L. helveticus*. The peptides act as ACE inhibitors. The anti-hypertensive activity of these peptides was tested on spontaneously hypertensive rats. Milk fermentation by an isogenic mutant of *Lb. helveticus* that does not have proteolytic activity does not show any anti-hypertensive effects.

The article [Gobbetti M. et al (2000, *Appl Environ Microbiol*, 66 (9), 3898-3904.], describes fermented milk containing ACE-inhibitory peptides that were produced by using either *Lactococcus lactis* subspecies *cremoris* FT4 or *Lactobacillus delbrueckii* subspecies *bulgaricus* SS1 to ferment the milk.

EP821968 (Calpis Food Industry) describes fermented milk containing ACE-inhibitory peptides that were produced by using a *Lactobacillus helveticus* strain with deposit accession number FERM BP-4835.

EP1016709 (Calpis Food Industry) describes fermented milk containing ACE-inhibitory peptides that were produced by using a *Lactobacillus helveticus* strain with deposit accession number FERM BP-6060.

WO01/32836 (Valio Ltd) describes fermented milk containing ACE-inhibitory peptides that were produced by using a *Lactobacillus helveticus* strain with deposit accession number DSM 13137.

Because lactic acid bacteria (LAB) are auxotrophic for a number of amino acids, LAB depend upon a complex proteolytic system to obtain essential amino acids from casein during growth in milk. The hydrolysis of casein into amino acids for use by LAB is initiated by cell wall proteinases that hydrolyse casein into oligopeptides. Oligopeptides are then transported into the bacterial cell via an oligopeptides transport system. Once the oligopeptides are inside the cell, intracellular peptidases hydrolyze them to free amino acids.

The article of University of Wisconsin and Utah State University [Pederson et al (1999, *J. of Bacteriology*, 181: 4592-4597] describes the DNA and amino acid sequence of a prtH 204 kDa cell wall proteinase from the *Lactobacillus helveticus* CNRZ32 strain. This article does not describe nor suggest using of the strain to make peptides with anti-hypertensive properties.

The article of the company Calpis Food Industry [Yamamoto et al (2000), *Biosci. Biotechnol. Biochem.*, 64(6): 1217-1222] describes the DNA and amino acid sequence of a prtY 45 kDa cell wall proteinase from the *Lactobacillus helveticus* CP790 strain. The CP790 strain does not comprises the prth 204 kDa cell wall proteinase [see "Discussion" section of Yamamoto et al (2000)]. The CP790 strain is used in a commercial product of Calpis Food Industry as the Materials and Methods sections reads, "CP790, was isolated from the starter culture of Calpis, a Japanese fermented milk product".

SUMMARY OF INVENTION

The problem to be solved by the present invention is to provide a method to obtain lactic acid bacteria (LAB) with improved characteristic in particular in relation to make peptides with anti-hypertensive properties.

The solution is based on that the present inventors have identified that lactic acid bacteria comprising a specific cell wall proteinase has such properties. The specific cell wall proteinase is herein termed prtH200. In working example 5 herein is demonstrated in vivo that a lactic acid bacteria having a prtH200 cell wall proteinase, as described herein, is capable of making peptides with improved anti-hypertensive properties.

The prtH200 proteinase, as described herein, correspond to the prtH 204 kDa cell wall proteinase from the *Lactobacillus helveticus* CNRZ32 strain described in the article of University of Wisconsin and Utah State University [Pederson et al (1999)] (see above). In this article it is not described nor suggested to use the CNRZ32 strain to make peptides with anti-hypertensive properties.

To the knowledge of the present inventor(s), no other references explicitly describe a lactic acid bacterium comprising a cell wall proteinase corresponding to the prtH200 proteinase as described herein.

In working example 3 herein it experimentally demonstrated that the *Lactobacillus helveticus* strain with deposit accession number DSM 13137, as described in WO01/32836

(Valio Ltd), does not comprise a prtH200 cell wall proteinase gene sequence identifiable by the specific prtH200 PCR primers as described herein.

As explained in the article of the company Calpis Food Industry [Yamamoto et al (2000)] (see above), at least one Japanese fermented milk product Calpis Food Industry comprises a strain (CP790) not having a prtH200 cell wall proteinase as described herein.

The presence, in a lactic acid bacterium, of a gene sequence encoding the prtH200 proteinase may preferably be verified by PCR amplification using suitable designed PCR primers. When the skilled person has suitable designed PCR primers it is easy for him to verify the presence or not of the gene sequence in a lactic acid bacterium using his general knowledge to make a specific suitable PCR amplification protocol.

Consequently, the skilled person may rapidly screen a number of lactic acid bacteria, identify the ones comprising a prtH200 gene sequence, and thereby obtain specific selected lactic acid bacteria with improved industrial relevant characteristic.

Accordingly, a first aspect of the invention relates to a method for obtaining a lactic acid bacterium comprising (i) investigating whether a lactic acid bacterium is a lactic acid bacterium that comprises a gene sequence encoding a cell wall proteinase (termed prtH200) wherein the gene sequences is identifiable by PCR amplification of genomic DNA of the lactic acid bacterium using sets of PCR primers selected from the group consisting of [sense sequence (S); antisense sequence (A)]:

```
PrtH200:
(a): (S): 5' CGATGATAATCCTAGCGAGC 3', (A): 5' TGGCAGAACCTGTGCCTA 3';

(b): (S): 5' GCCAAGACGCCTCTGGTA 3', (A): 5' TAGGTATAGTTTCCATCAGGA 3'; and (c): (S): 5' AARGTWCCWTAYGGYYWYAAYTA 3', (A): 5' GCCATDSWDGTRCCDSWCATDTK 3'; and
```

(ii) if the lactic acid bacterium fulfills the criteria of step (i) then the lactic acid bacterium is obtained; or (iii) if the lactic acid bacterium does not fulfill the criteria of step (i) then repeat step (i) with another lactic acid bacterium, with the exception of the situation wherein the lactic acid bacterium is the *Lactobacillus helveticus* CNRZ32 strain.

The term "*Lactobacillus helveticus* CNRZ32 strain" refers to the strain described in the article of University of Wisconsin and Utah State University [Pederson et al (1999)] (see above).

The DNA and amino acid sequence of prtH200 of *Lactobacillus helveticus* DSM 14998 is shown in SEQ ID NO 1 and SEQ ID NO 2.

Based on the prtH200 sequences and sequences homologues to these suitable PCR primers may routinely be identified in order to identify the prtH200 gene of SEQ ID NO 1 and genes homologous to this.

Accordingly, a second aspect of the invention relates to a method for obtaining a lactic acid bacterium comprising (i) investigating whether a lactic acid bacterium is a lactic acid bacterium that comprises a gene sequence encoding a cell wall proteinase (termed prtH200), wherein the gene sequence is defined as prtH200 is a DNA sequence encoding an enzyme exhibiting cell wall proteinase activity, which DNA sequence is selected from the group consisting of:

(a) the DNA sequence shown in positions 1-5550 in SEQ ID NO 1;

(b) a DNA sequence comprising a fragment of at least 75 base pairs (bp) that is at least 50% identical to a corresponding fragment of the DNA sequence defined in (a);

(c) a DNA sequence that encodes a polypeptide, exhibiting cell wall proteinase activity, comprising a fragment of at least 200 amino acids (aa) that is at least 30% identical to a corresponding fragment of the polypeptide sequence shown in positions 1-1849 of SEQ ID NO 2;

(d) a DNA sequence which hybridizes with a double-stranded DNA probe comprising the DNA sequence shown in positions 1-5550 in SEQ ID NO 1 at low stringency; and (e) a DNA sequence which is a fragment of the DNA sequences specified in (a), (b), (c), or (d); and (ii) if the lactic acid bacterium fulfills the criteria of step (i) then the lactic acid bacterium is obtained; or (iii) if the lactic acid bacterium does not fulfill the criteria of step (i) then repeat step (i) with another lactic acid bacterium, with the exception of the situation wherein the lactic acid bacterium is the *Lactobacillus helveticus* CNRZ32 strain.

As said above, an advantage of lactic acid bacteria comprising a prtH200 proteinase, as described herein, is improved characteristic in relation to make peptides with anti-hypertensive properties.

Consequently, in a third aspect the invention relates to a process for preparing peptides with anti-hypertensive properties, the process comprising fermenting a food material, comprising animal milk proteins or vegetable proteins, with a lactic acid bacterium to obtain a fermented food material which comprises the peptides with anti-hypertensive properties, characterized in that the lactic acid bacterium comprises a gene sequence encoding a cell wall proteinase (termed prtH200) and the presence of the cell wall proteinases is identifiable by PCR amplification of genomic DNA of the lactic acid bacterium using sets of PCR primers selected from the group consisting of [sense sequence (S); antisense sequence (A)]:

```
PrtH200:
(a): (S): 5' CGATGATAATCCTAGCGAGC3', (A): 5' TGGCAGAACCTGTGCCTA 3';

(b): (S): 5' GCCAAGACGCCTCTGGTA 3', (A): 5' TAGGTATAGTTTCCATCAGGA 3'; and (c): (S): 5' AARGTWCCWTAYGGYYWYAAYTA 3', (A): 5' GCCATDSWDGTRCCDSWCATDTK 3'.
```

In a fourth aspect, the invention relates to a process for preparing peptides with anti-hypertensive properties, the process comprising fermenting a food material, comprising animal milk proteins or vegetable proteins, with a lactic acid bacterium to obtain a fermented food material which comprises the peptides with anti-hypertensive properties, characterized in that the lactic acid bacterium comprises a gene sequence encoding a cell wall proteinase (termed prtH200), wherein the gene sequence is defined as prtH200 is a DNA sequence encoding an enzyme exhibiting cell wall proteinase activity, which DNA sequence is selected from the group comprising of:
  (a) the DNA sequence shown in positions 1-5550 in SEQ ID NO 1;
  (b) a DNA sequence comprising a fragment of at least 75 base pairs (bp) that is at least 50% identical to a corresponding fragment of the DNA sequence defined in (a);
  (c) a DNA sequence that encodes a polypeptide, exhibiting cell wall proteinase activity, comprising a fragment of at least 200 amino acids (aa) that is at least 30% identical to a corresponding fragment of the polypeptide sequence shown in positions 1-1849 of SEQ ID NO 2;
  (d) a DNA sequence which hybridizes with a double-stranded DNA probe comprising the DNA sequence shown in positions 1-5550 in SEQ ID NO 1 at low stringency; and
  (e) a DNA sequence which is a fragment of the DNA sequences specified in (a), (b), (c), or (d).

As explained above, to the knowledge of the present inventor(s), no references explicitly describe the use of a lactic acid bacterium as described herein in a process according to the third and fourth aspect herein. However, it might be that future experiments demonstrate that a lactic acid bacterium, described prior to the filing date of the present application to have been used in a process according to the third and fourth aspect herein, does comprise the prtH200 gene sequences as described herein. In such a hypothetical case the specific lactic acid bacterium will be disclaimed from the scope of the claims of the third and fourth aspect of the present invention. In other words, the third and fourth aspect will include a statement that could read "with the exception of a possible specific lactic acid strain".

A fifth aspect of the invention relates to a process for preparing peptides comprising
  (i) obtaining a lactic acid bacterium by a method for obtaining a lactic acid bacterium according to the first and second aspect of the invention;
  (ii) fermenting a material comprising proteins with the lactic acid bacterium obtained in (i) to obtain a fermented material which comprises the peptides.

An embodiment of the fifth aspect of the invention relates to a process for preparing peptides with anti-hypertensive properties comprising
  (i) obtaining a lactic acid bacterium by a method for obtaining a lactic acid bacterium according to the first and/or second aspect of the invention;
  (ii) fermenting a food material, comprising animal milk proteins or vegetable proteins, with the lactic acid bacterium obtained in (i) to obtain a fermented food material which comprises the peptides with anti-hypertensive properties.

The disclaimer discussion above, in relation to the third and fourth aspect of the invention, is not relevant for the fifth aspect and its embodiments. The fifth aspect includes a step of actively investigating the presence, in the lactic acid bacterium, of the prtH200 proteinase discussed herein. In the present context this step is novel.

Peptides produced as described herein, may be used to prepare a functional food product with anti-hypertensive properties.

Accordingly, a sixth aspect the invention relates to a process for preparing a functional food product comprising peptides with anti-hypertensive properties, the process comprising following steps:
  (i) preparing a fermented food material according to a process for preparing peptides with anti-hypertensive properties, as described herein, and
  (ii) packing it in a suitable way to get a functional food product.

The term "packing" should be understood broadly. It denotes that once a food material is fermented and a fermented food material is obtained, the fermented food material should be packed in order to could be provided to the consumer. It may be packed in a bottle, a tetra-pack, etc. Preferably, on the package or in corresponding marketing material is indicated that the functional food product has anti-hypertensive properties.

The process of the sixth aspect, illustrates one of the advantages of the processes as described herein. The use of lactic acid bacteria comprising the prtH200 proteinases as described herein provides directly after the fermentation a useful amount of peptides with very good anti-hypertensive properties. Consequently, it is not considered necessary to further purify or up-concentrate the peptides from the fermented food material. The fermented food material may be packed directly and provided to the market as a functional food product.

In a seventh aspect the invention relates to peptides with anti-hypertensive properties obtainable by a process for preparing peptides with anti-hypertensive properties as described herein.

Peptides, produced by fermentation with lactic acid bacteria comprising the prtH200 proteinase as described herein, are different from peptides produced by fermentation with lactic acid bacteria not comprising these proteinases. This may be verified functionally by the improved anti-hypertensive effects of the peptides produced by fermentation with lactic acid bacteria comprising the prtH200 proteinase as described herein.

In an eighth aspect the invention relates to a functional food product comprising peptides with anti-hypertensive properties obtainable by a process for preparing a functional food product as described herein.

In a ninth aspect the invention relates to use of peptides with anti-hypertensive properties of the seventh aspect for the manufacture of a medicament for the treatment of hypertension.

In a tenth aspect the invention relates to use of a functional food product comprising peptides with anti-hypertensive properties of the eighth aspect for the manufacture of a medicament for the treatment of hypertension.

DEFINITIONS

Prior to a discussion of the detailed embodiments of the invention is provided a definition of specific terms related to the main aspects of the invention.

The term "lactic acid bacteria" denotes herein a group of Gram-positive, non-sporing bacteria, which carry out a lactic acid fermentation of sugars.

The term "gene" is herein defined according to is usual meaning as the fundamental physical and functional unit of heredity. A gene is an ordered sequence of nucleotides (e.g. DNA or RNA) located in a particular position on a particular chromosome that encodes a specific functional product (i.e., a protein or RNA molecule).

The "nomenclature of degenerated primers" is according to the standard nomenclature in the art. Y=C or T; R=A or G; M=A or C; K=G or T; S=G or C; W=A or T; H=A or C or T; B=G or T or C; V=G or C or A; D=G or A or T; N=G, A, C or T.

The term a "fragment" in relation to a DNA/amino acid sequence comprising a fragment denotes a continuous partial sequence. For instance, from position 75 to 300 in an amino acid sequence having 600 amino acids.

The term "a corresponding fragment" in relation to identity comparison between two sequences relates to a fragment of corresponding size. Preferably, the size difference, between the two fragments to be compared, is less than 50%. In order words, if one fragment is 100 bp the other is preferably less than 150 bp. More preferably, the size difference, between the two fragments to be compared, is less than 25%, and even more preferably the size difference, between the two fragments to be compared, is less than 5%.

Embodiment(s) of the present invention is described below, by way of example(s) only.

DRAWINGS

FIG. 1: The FIGURE contains pulsed field gel electrophoresis (PFGE) fingerprinting of *Lactobacillus helveticus* strain CHCC5951 (deposited with accession number DSM 14998) This FIGURE and working example 7 show that a PFGE fingerprint of the CHCC5951 strain identifies at least 12 characterizing bands described infra.

DETAILED DESCRIPTION OF THE INVENTION prtH200 Cell Wall Proteinase

The activity of a cell wall proteinase is preferably verified while it is present in the lactic acid bacteria. A suitable strategy is to construct a lactic acid bacterium with a lethal mutation in the gene encoding the cell wall proteinase to be analyzed. The proteolytic activity (for a suitable assay see below) of this constructed bacterium could then be compared with the corresponding wildtype bacterium. A measurable decrease in proteolytic activity of the lactic acid bacterium with a lethal mutation as compared with the corresponding wildtype bacterium would experimentally confirm that the gene encoding the cell wall proteinase to be analyzed is a gene encoding a active lactic acid cell wall proteinase.

The skilled person knows how to construct a lactic acid bacterium with a suitable lethal mutation. Reference is made to e.g. Pederson et al (1999) and Yamamoto et al (1994) (see above).

At the filing date of the present invention, the National Center for Biotechnology Information (NCBI) offered at its Internet site the possibility of making a standard BLAST computer sequence homology search.

The DNA and amino acid sequence of prtH200 of *Lactobacillus helveticus* DSM 14998 as shown in SEQ ID NO 1 and SEQ ID NO 2 has been published at the GeneBank database with accession number AF133727. The database sequence identification is gi|5758038|gb|AF133727.1|AF133727.

Standard protein-protein BLAST [blastp] search using the prtH200 amino acid sequence shown in position 1-1849 in SEQ ID NO 2 as reference sequence gave, among others, following results (in italic is given the database sequence identification. This info unambiguously identifies the published sequence and the skilled person know how to get the sequence based on this):

gi|129346|sp|P15293|P2P_LACLC: PII-type proteinase precursor (Lactocepin) (Cell wall-associated serine proteinase). Organism: *Lactococcus lactis* subsp. *cremoris*. Identity: a 1600 amino acid fragment with 50% identity of to a corresponding fragment of the prtH200 amino acid sequence of SEQ ID NO 2.

gi|149582|gb|AAA25248.1|: proteinase Organism: *Lactobacillus paracasei*. Identity: a 1632 amino acid fragment with 49% identity of to a corresponding fragment of the prtH200 amino acid sequence of SEQ ID NO 2.

gi|1381114|gb|AAC41529.1|: (L48487) proteinase precursor Organism: *Lactobacillus delbrueckii*. Identity: a 1682 amino acid fragment with 32% identity of to a corresponding fragment of the prtH200 amino acid sequence of SEQ ID NO 2.

gi|18568398|gb|AAL76069.1|: (AF468027) cell-envelope proteinase. Organism: *Lactobacillus pentosus*. Identity: a 415 amino acid fragment with 63% identity of to a corresponding fragment of the prtH200 amino acid sequence of SEQ ID NO 2.

gi|9963932|gb|AAG09771.1|AF243528_1: (AF243528) cell envelope proteinase. Organism: *Streptococcus thermophilus* Identity: a 781 amino acid fragment with 30% identity of to a corresponding fragment of the prtH200 amino acid sequence of SEQ ID NO 2.

gi|482386|pir||A44833: lactocepin (EC 3.4.21.96). Organism: *Lactococcus lactis*. Identity: a 264 amino acid fragment with 61% identity of to a corresponding fragment of the prtH200 amino acid sequence of SEQ ID NO 2.

These specific sequences are all representing a DNA sequence that encodes a polypeptide, exhibiting cell wall proteinase activity, comprising a fragment of at least 200 amino acids (aa) that is at least 30% identical to a corresponding fragment of the polypeptide sequence shown in positions 1-1849 of SEQ ID NO 2.

Standard nucleotide-nucleotide BLAST [blastn] search using the prtH200 DNA sequence shown in position 1-5550 in SEQ ID NO 1 as reference sequence gave, among others, following results gi|149580|gb|M83946.1|LBAMPRO. Proteinase (prtP) gene. Organism: *Lactobacillus paracasei*. Identity: a 102 bp fragment with 84% identity of to a corresponding fragment of the prtH200 DNA sequence of SEQ ID NO 1.

gi|47197|emb|X14130.1|SLPRT763. plasmid pLP763 prt gene for cell wall-associated serine proteinase. Organism: *Streptococcus lactis* Identity: a 81 bp fragment with 86% identity of to a corresponding fragment of the prtH200 DNA sequence of SEQ ID NO 1.

gi|472834|gb|M24767.1|STRWGPROT. Wg2 proteinase gene. Organism: *S. cremoris* Identity: a 81 bp fragment with 86% identity of to a corresponding fragment of the prtH200 DNA sequence of SEQ ID NO 1.

gi|149476|gb|J04962.1|LACPRASE. PIII-type proteinase (prtP) and maturation protein. Organism: *Lactococcus lactis*. Identity: a 81 bp fragment with 86% identity of to a corresponding fragment of the prtH200 DNA sequence of SEQ ID NO 1.

gi|8568397|gb|AF468027.1|. cell-envelope proteinase (prtP) gene. Organism: *Lactobacillus pentosus* Identity: a 102 bp fragment with 83% identity of to a corresponding fragment of the prtH200 DNA sequence of SEQ ID NO 1.

These specific sequences are all representing a DNA sequence comprising a fragment of at least 75 base pairs (bp) that is at least 50% identical to a corresponding fragment of the DNA sequence shown in positions 1-5550 of SEQ ID NO 1.

Other "fingerprint" gene sequences (orfF3, orfF4 and orfF1):

The prtH200 gene sequence discussed herein may be seen as a "fingerprint" of the lactic acid bacteria (LAB).

orfF3:

Preferably, beside a prtH200 gene sequence the LAB also comprises a gene comprising an open reading frame herein termed orfF3. This gene may be seen as an additional fingerprint.

The DNA and amino acid sequence of orfF3 of *Lactobacillus helveticus* DSM 14998 is shown in SEQ ID NO 3 and SEQ ID NO 4. Working example 3 shows identification of orfF3 based on suitable primers.

Accordingly, in a preferred embodiment, a lactic acid bacterium, as described herein, comprises the prtH200 gene and a gene sequence (termed orfF3) encoding an open reading frame wherein the gene sequences is identifiable by PCR amplification of genomic DNA of the lactic acid bacterium using sets of PCR primers selected from the group consisting of [sense sequence (S); antisense sequence (A)]:

```
orfF3:
(a): (S): 5' CGAAGGCGATAAGTCAAACTTTGATAATGC 3',
     (A): 5' CCCGGTTCTGTAAGATAATTTGGATCG 3'; and
(b): (S): 5' ASTCWRRYTTYGATRATGCW 3',
     (A): 5' BHKYAMSAWARTTTGGATCR 3'.
```

As said above suitable PCR primers may be identified based on the sequences disclosed herein.

Accordingly, in a preferred embodiment, a lactic acid bacterium, as described herein, comprises the prtH200 gene and a gene sequence encoding an open reading frame (termed orfF3), wherein the gene sequence is defined as orfF3 is a DNA sequence encoding an open reading frame, which DNA sequence is selected from the group comprising of:
  (a) the DNA sequence shown in positions 1-2679 in SEQ ID NO 3;
  (b) a DNA sequence comprising a fragment of at least 75 base pairs (bp) that is at least 40% identical to a corresponding fragment of the DNA sequence defined in (a);
  (c) a DNA sequence that encodes a polypeptide comprising a fragment of at least 200 amino acids (aa) that is at least 30% identical to a corresponding fragment of the polypeptide sequence shown in positions 1-893 of SEQ ID NO 4;
  (d) a DNA sequence which hybridizes with a double-stranded DNA probe comprising the DNA sequence shown in positions 1-2679 in SEQ ID NO 3 at low stringency; and
  (e) a DNA sequence which is a fragment of the DNA sequences specified in (a), (b), (c), or (d).

The term "open reading frame" denotes a stretch of DNA that contains a signal for the start of translation followed in the correct register by a sufficient length of amino acid encoding triplets to form a protein, followed by a signal for termination of translation, and which may therefore indicate the presence of a protein coding gene.

At the filing date of the present application, a standard protein-protein BLAST [blastp] search using the deduced orfF3 amino acid sequence shown in position 1-893 in SEQ ID NO 4 as reference sequence gave relatively limited conclusive results in relation to published homologous sequences.

However, without being limited to theory, it is believed that an orfF3 gene as described herein encodes a cell wall proteinase. Consequently, in a preferred embodiment the orfF3 gene as described herein encodes a cell wall proteinase.

orfF4:

Preferably, beside a prtH200 gene sequence the LAB also comprises a gene comprising an open reading frame herein termed orfF4.

The DNA and amino acid sequence of orfF4 of *Lactobacillus helveticus* DSM 14998 is shown in SEQ ID NO 5 and SEQ ID NO 6. Working example 3 shows identification of orfF4 based on suitable primers.

Accordingly in a preferred embodiment, a lactic acid bacterium, as described herein, comprises the prtH200 gene and a gene sequence (termed orfF4) encoding an open reading frame wherein the gene sequences is identifiable by PCR amplification of genomic DNA of the lactic acid bacterium using sets of PCR primers selected from the group consisting of [sense sequence (S); antisense sequence (A)]:

```
orfF4:
(a): (S): 5' GGTGTTGCTCCTGAAGC 3'
     (A): 5' ACTCTAGCACCAGCTAATTGAACATCATG 3'.
```

As said above suitable PCR primers may be identified based on the sequences disclosed herein.

Accordingly, in a preferred embodiment, a lactic acid bacterium, as described herein, comprises the prtH200 gene and a gene sequence encoding an open reading frame (termed orfF4), wherein the gene sequence is defined as orfF4 is a DNA sequence encoding an open reading frame, which DNA sequence is selected from the group comprising of:
  (a) the DNA sequence shown in positions 1-4881 in SEQ ID NO 5;
  (b) a DNA sequence comprising a fragment of at least 75 base pairs (bp) that is at least 40% identical to a corresponding fragment of the DNA sequence defined in (a);
  (c) a DNA sequence that encodes a polypeptide comprising a fragment of at least 200 amino acids (aa) that is at least 30% identical to a corresponding fragment of the polypeptide sequence shown in positions 1-1627 of SEQ ID NO 6;
  (d) a DNA sequence which hybridizes with a double-stranded DNA probe comprising the DNA sequence shown in positions 1-4881 in SEQ ID NO 5 at low stringency; and
  (e) a DNA sequence which is a fragment of the DNA sequences specified in (a), (b), (c), or (d).

At the filing date of the present application, a standard protein-protein BLAST [blastp] search using the deduced orfF4 amino acid sequence shown in position 1-1627 in SEQ ID NO 6 as reference sequence gave relatively limited conclusive results in relation to published homologous sequences.

However, without being limited to theory, it is believed that an orfF4 gene as described herein encodes a cell wall proteinase. Consequently, in a preferred embodiment the orfF4 gene as described herein encodes a cell wall proteinase.

Preferably, a lactic acid bacterium, as described herein, comprises the prtH200 gene, the orfF3 gene and the orf4 gene as described herein.

orfF1:

Preferably, beside a prtH200 gene sequence the LAB also comprises a gene comprising an open reading frame herein termed orfF1.

The DNA and amino acid sequence of orfF1 of *Lactobacillus helveticus* DSM 14998 is shown in SEQ ID NO 19 and SEQ ID NO 20.

Accordingly, in a preferred embodiment, a lactic acid bacterium, as described herein, comprises the prtH200 gene and a gene sequence encoding an open reading frame (termed orfF1), wherein the gene sequence is defined as orfF1 is a DNA sequence encoding an open reading frame, which DNA sequence is selected from the group comprising of:
  (a) the DNA sequence shown in positions 1-5358 in SEQ ID NO 19;
  (b) a DNA sequence comprising a fragment of at least 75 base pairs (bp) that is at least 40% identical to a corresponding fragment of the DNA sequence defined in (a);
  (c) a DNA sequence that encodes a polypeptide comprising a fragment of at least 200 amino acids (aa) that is at least 30% identical to a corresponding fragment of the polypeptide sequence shown in positions 1-1785 of SEQ ID NO 20;
  (d) a DNA sequence which hybridizes with a double-stranded DNA probe comprising the DNA sequence shown in positions 1-5358 in SEQ ID NO 19 at low stringency; and
  (e) a DNA sequence which is a fragment of the DNA sequences specified in (a), (b), (c), or (d).

At the filing date of the present application, a standard protein-protein BLAST [blastp] search using the deduced orfF1 amino acid sequence shown in position 1-1785 in SEQ ID NO 20 as reference sequence gave relatively limited conclusive results in relation to published homologous sequences.

However, without being limited to theory, it is believed that an orfF1 gene as described herein encodes a cell wall proteinase. Consequently, in a preferred embodiment the orfF1 gene as described herein encodes a cell wall proteinase.

Preferably, a lactic acid bacterium, as described herein, comprises the prtH200 gene, the orfF3 gene, the orfF4 gene and the orfF1 gene as described herein.

Pulsed Field Gel Electrophoresis (PFGE) Fingerprinting

Another suitable way of characterizing a LAB as described herein is by use a so-called pulsed field gel electrophoresis (PFGE) fingerprinting technique.

PFGE fingerprinting is a standard technique. The herein preferred protocol is that chromosomal DNA is isolated from a bacterium of interest, completely digested with restriction enzyme SmaI and run on an agarose gel together with a suitable standard MW marker. Working example 7 herein describes a preferred PFGE protocol in further details.

By analyzing the agarose gel, specific DNA bands for a LAB of interest may be identified. FIG. 1 herein, shows this for the herein described very preferred *Lactobacillus helveticus* strain CHCC5951 (deposited with accession number DSM 14998). FIG. 1 and working example 7 show that a PFGE fingerprint of the CHCC5951 strain identifies at least 12 characterizing bands. These bands are:
  band no. 1: 283 kbp
  band no. 2: 259 kbp
  band no. 3: 219 kbp
  band no. 4: 138 kbp
  band no. 5: 127 kbp
  band no. 6: 119 kbp
  band no. 7: 106 kbp
  band no. 8: 88 kbp
  band no. 9: 71 kbp
  band no. 10: 59 kbp
  band no. 11: 54 kbp
  band no. 12: 46 kbp Identical PFGE fingerprints have been made for a number of strains including the Calpis Food Industry and Valio Ltd strains described in the background art section above.

None of the tested strains comprised a combination of the two bands corresponding to band no. 1 of 283 kbp and band no 3 of 219 kbp. Further none of the tested strains comprised a band corresponding to the band no. 12 of 46 kbp.

These bands encode information that is responsible for the improved characteristic of a LAB as described herein.

Accordingly, in a preferred embodiment, a lactic acid bacterium, as described herein, comprises the prtH200 gene and a combination of the two PFGE fingerprinting bands corresponding to the of 283 kbp and the band of 219 kbp of a PFGE fingerprint of the *Lactobacillus helveticus* bacterium with the registration number DSM 14998, wherein the PFGE fingerprinting is made by a protocol comprising isolation of chromosomal DNA of the lactic acid bacterium, completely digest the chromosomal DNA with restriction enzyme SmaI and electrophorese the digested DNA on an agarose gel.

The term "PFGE fingerprinting band corresponding to the specific mentioned size band of a PFGE fingerprint of the *Lactobacillus helveticus* bacterium with the registration number DSM 14998" should be understood in the sense that *Lactobacillus helveticus* DSM 14998 may be seen as a reference strain. Preferably, there should be made an identical (using the same protocol) PFGE fingerprint of a LAB of interest and the *Lactobacillus helveticus* DSM 14998. The digested DNA of the LAB of interest and the *Lactobacillus helveticus* DSM 14998 could thereafter be electrophoresed on the same agarose gel together with a suitable MW marker. By analyzing the electrophoresed agarose gel, the skilled person may then by use of routine skills determine if the LAB of interest comprise the band(s) corresponding to the specific mentioned size band of the *Lactobacillus helveticus* DSM 14998. As known to the skilled person, there might be some minor variation is size. In the present context, such minor variation should preferably be within ±5 kbp. Accordingly, if the reference band of *Lactobacillus helveticus* DSM 14998 is e.g. 283 kbp then the corresponding band of an analyzed LAB of interest should preferably be of a size of 283 kbp ±5 kb.

In another preferred embodiment, a lactic acid bacterium, as described herein, comprises the prtH200 gene and the PFGE fingerprinting band corresponding to the 46 kbp band of a PFGE fingerprint of the *Lactobacillus helveticus* bacterium with the registration number DSM 14998, wherein the PFGE fingerprinting is made by a protocol comprising isolation of chromosomal DNA of the lactic acid bacterium, completely digest the chromosomal DNA with restriction enzyme SmaI and electrophorese the digested DNA on an agarose gel.

Analyzed in the same way it is more preferred that the lactic acid bacterium, as described herein, comprises all of the following PFGE fingerprinting bands:
  band corresponding to the 283 kbp band of the *Lactobacillus helveticus* DSM 14998,
  band corresponding to the 219 kbp band of the *Lactobacillus helveticus* DSM 14998,
  band corresponding to the 46 kbp band of the *Lactobacillus helveticus* DSM 14998.

Most preferably, the lactic acid bacterium, as described herein, comprises bands corresponding to all of the twelve PFGE fingerprinting bands given above for the *Lactobacillus helveticus* DSM 14998.

PCR Amplification

As said above, the presence of the gene sequences, as described herein, may preferably be verified by PCR amplification using PCR primers designed according to the teaching herein. When the skilled person has suitable designed PCR primers it is easy for him to verify the presence or not of these genes in a lactic acid bacterium using his general knowledge to make a specific suitable PCR amplification protocol.

Preferably the PCR amplification protocol (reaction) is made according to the description of Example 1 herein.

Once the PCR have been performed it is routine for the skilled person to investigate whether or not the resulting PCR amplified fragments corresponds to fragments of genes as described herein. Normally this may be identified already based on the size of the PCR fragment, since the skilled person generally roughly knows how big the size of a positive PCR fragment would be. A positive PCR fragment relates to a PCR fragment of a gene as described herein. Alternatively, the PCR fragment may be DNA sequenced and the resulting DNA sequence may then be compared with the sequences disclosed herein. Further, a lactic acid bacterium with a lethal mutation in the gene corresponding to the PCR fragment could be constructed. The proteolytic activity (see below) of this constructed bacterium could then be compared with the corresponding wildtype bacterium and a measurable change in proteolytic activity between the two cells would experimentally confirm whether or not the gene corresponding to the amplified PCR fragment is a gene encoding a lactic acid cell wall proteinase as described herein.

In summary, the skilled person can routinely identify whether or not a specific lactic acid bacterium comprises gene(s) capable of giving corresponding positive PCR fragments using PCR primers designed according to the teaching herein.

PCR is the preferred way to investigate the presence or not in the lactic acid bacteria of the genes as described herein. However, it may be done in other ways such as e.g. by Southern blot analysis.

PCR primers:

As explained above suitable PCR primers in relation to the PrtH200 gene are:

```
PrtH200:
(a): (S): 5' CGATGATAATCCTAGCGAGC3', (A): 5' TGGCAGAACCTGTGCCTA 3';

(b): (S): 5' GCCAAGACGCCTCTGGTA 3', (A): 5' TAGGTATAGTTTCCATCAGGA 3'; and (c): (S): 5' AARGTWCCWTAYGGYYWYAAYTA 3', (A): 5' GCCATDSWDGTRCCDSWCATDTK 3'.
```

PrtH200: (a): (S) is shown in SEQ ID NO 7; PrtH200: (a): (A) is shown in SEQ ID NO 8;
PrtH200: (b): (S) is shown in SEQ ID NO 9; PrtH200: (b): (A) is shown in SEQ ID NO 10;
PrtH200: (c): (S) is shown in SEQ ID NO 11; PrtH200: (c): (A) is shown in SEQ ID NO 12.

When using the primer set (a) the amplified PrtH200 PCR fragment should preferably be of a size between 400 bp and 800 bp, more preferably of a size between 500 bp and 700 bp. When using the primer set (b) the amplified PrtH200 PCR fragment should preferably be of a size between 200 bp and 500 bp, more preferably of a size between 250 bp and 375 bp. When using the primer set (c) the amplified PrtH200 PCR fragment should preferably be of a size between 400 bp and 800 bp, more preferably of a size between 500 bp and 700 bp.

The most preferred PrtH200 related PCR primers are primer set (a) and primer set (b).

As said above suitable PCR primers in relation to orfF3 are:

```
orfF3:
(a): (S): 5' CGAAGGCGATAAGTCAAACTTTGATAATGC 3', (A): 5' CCCGGTTCTGTAAGATAATTTGGATCG 3'; and (b): (S): 5' ASTCWRRYTTYGATRATGCW 3', (A): 5' BHKYAMSAWARTTTGGATCR 3'.
``` orfF3: (a): (S) is shown in SEQ ID NO 13; orfF3: (a): (A) is shown in SEQ ID NO 14;
orfF3: (b): (S) is shown in SEQ ID NO 15; orfF3: (b): (A) is shown in SEQ ID NO 16.

When using the primer set (a) the amplified orfF3 PCR fragment should preferably be of a size between 1250 bp and 1900 bp, more preferably of a size between 1500 bp and 1725 bp. When using the primer set (b) the amplified orfF3 PCR fragment should preferably be of a size between 1250 bp and 1900 bp, more preferably of a size between 1500 bp and 1725 bp.

The most preferred orfF3 related PCR primers is the primer set (a).

As said above suitable PCR primers in relation to orfF4 is:

```
orfF4:
(a): (S): 5' GGTGTTGCTCCTGAAGC 3'

(A): 5' ACTCTAGCACCAGCTAATTGAACATCATG 3'.
``` orfF4: (a): (S) is shown in SEQ ID NO 17; orfF4: (a): (A) is shown in SEQ ID NO 18.

When using the primer set (a) the amplified orfF4 PCR fragment should preferably be of a size between 700 bp and 1150 bp, more preferably of a size between 875 bp and 1025 bp.

Homology/Identity of DNA Sequences

The DNA sequence homology/identity referred to above is determined as the degree of identity between two sequences indicating a deviation of the first sequence from the second.

At the filing date of the present invention, the National Center for Biotechnology Information (NCBI) offered at it Internet site (http://www.ncbi.nlm.nih.gov/) the possibility of making a standard BLAST computer sequence homology search.

BLAST program is described in [Altschul et al (1997), "Gapped BLAST and PSI-BLAST: a new generation of protein database search programs", Nucleic Acids Res. 25:3389-3402].

In the present context, a preferred computer homology search program is a "Standard nucleotide-nucleotide BLAST [blastn]" search as specified, at the filing date of the present application, at the NCBI Internet site with setting filter: Low complexity; Expect: 10, Word Size: 11.

The reference sequence is introduced into the program and the program identifies fragments of published sequences together the identity percentage to a corresponding fragment of the reference sequence.

Using this Standard nucleotide-nucleotide BLAST computer program, a prtH200 sequence as described herein is preferably a DNA sequence comprising a fragment of at least 75 base pairs (bp) that is at least 60% identical to a corresponding fragment of the prtH200 DNA sequence shown in position 1-5550 of SEQ ID NO 1, more preferably a DNA sequence comprising a fragment of at least 75 base pairs (bp) that is at least 70% identical to a corresponding fragment of the prtH200 DNA sequence shown in position 1-5550 of SEQ ID NO 1, and even more preferably a DNA sequence comprising a fragment of at least 75 base pairs (bp) that is at least 80% identical to a corresponding fragment of the prtH200 DNA sequence shown in position 1-5550 of SEQ ID NO 1.

With the identity percentages given above, it is preferred that the fragment is at least 100 bp pairs (bp), more preferably that the fragment is at least 200 bp pairs (bp), even more preferably that the fragment is at least 400 bp pairs (bp), and most preferably that the fragment is at least 1500 bp pairs (bp).

Using this Standard nucleotide-nucleotide BLAST computer program, a orfF3 sequence as described herein is preferably a DNA sequence comprising a fragment of at least 75 base pairs (bp) that is at least 60% identical to a corresponding fragment of the orfF3 DNA sequence shown in position 1-2679 of SEQ ID NO 3, more preferably a DNA sequence comprising a fragment of at least 75 base pairs (bp) that is at least 70% identical to a corresponding fragment of the orfF3 DNA sequence shown in position 1-2679 of SEQ ID NO 3, and even more preferably a DNA sequence comprising a fragment of at least 75 base pairs (bp) that is at least 80% identical to a corresponding fragment of the orfF3 DNA sequence shown in position 1-2679 of SEQ ID NO 3.

With the identity percentages given above, it is preferred that the fragment is at least 100 bp pairs (bp), more preferably that the fragment is at least 200 bp pairs (bp), even more preferably that the fragment is at least 400 bp pairs (bp), and most preferably that the fragment is at least 1500 bp pairs (bp). p Using this Standard nucleotide-nucleotide BLAST computer program, a orfF4 sequence as described herein is preferably a DNA sequence comprising a fragment of at least 75 base pairs (bp) that is at least 60% identical to a corresponding fragment of the orfF4 DNA sequence shown in position 1-4881 of SEQ ID NO 5, more preferably a DNA sequence comprising a fragment of at least 75 base pairs (bp) that is at least 70% identical to a corresponding fragment of the orfF4 DNA sequence shown in position 1-4881 of SEQ ID NO 5, and even more preferably a DNA sequence comprising a fragment of at least 75 base pairs (bp) that is at least 80% identical to a corresponding fragment of the orfF4 DNA sequence shown in position 1-4881 of SEQ ID NO 5.

With the identity percentages given above, it is preferred that the fragment is at least 100 bp pairs (bp), more preferably that the fragment is at least 200 bp pairs (bp), even more preferably that the fragment is at least 400 bp pairs (bp), and most preferably that the fragment is at least 1500 bp pairs (bp).

Alternatively, the homology/identity may suitably be determined by means of computer programs known in the art, such as GAP provided in the GCG program package (Program Manual for the Wisconsin Package, Version 8, Aug. 1994, Genetics Computer Group, 575 Science Drive, Madison, Wis., USA 53711)(Needleman, S. B. and Wunsch, C. D., (1970), Journal of Molecular Biology, 48, 443-453).

Using GAP with the following settings for DNA sequence comparison, GAP creation penalty of 5.0 and GAP extension penalty of 0.3, the preferred identity percentages given above in relation to the BLAST program are also the preferred identities when using GAP.

Homology to Amino Acid Sequences

Similar to the nucleotide homology analysis, in the present context, a preferred computer homology search program is a "Standard protein-protein BLAST [blastp]" search as specified, at the filing date of the present application, at the NCBI Internet site with settings Composition-based statistics: yes, filter: Low complexity; Expect: 10, Word Size: 3, Matrix: BLOSUM 62, Gap Costs: Existence 11 Extension 1.

Using this standard protein-protein BLAST computer program, a prtH200 sequence as described herein is preferably a DNA sequence that encodes a polypeptide, exhibiting cell wall proteinase activity, comprising a fragment of at least 200 amino acids (aa) that is at least 40% identical to a corresponding fragment of the prtH200 polypeptide sequence shown in positions 1-1849 of SEQ ID NO 2, more preferably a DNA sequence that encodes a polypeptide, exhibiting cell wall proteinase activity, comprising a fragment of at least 200 amino acids (aa) that is at least 50% identical to a corresponding fragment of the prtH200 polypeptide sequence shown in positions 1-1849 of SEQ ID NO 2, even more preferably a DNA sequence that encodes a polypeptide, exhibiting cell wall proteinase activity, comprising a fragment of at least 200 amino acids (aa) that is at least 65% identical to a corresponding fragment of the prtH200 polypeptide sequence shown in positions 1-1849 of SEQ ID NO 2, and most preferably a DNA sequence that encodes a polypeptide, exhibiting cell wall proteinase activity, comprising a fragment of at least 200 amino acids (aa) that is at least 80% identical to a corresponding fragment of the prtH200 polypeptide sequence shown in positions 1-1849 of SEQ ID NO 2.

With the identity percentages given above, it is preferred that the fragment is at least 300 amino acids (aa), more preferably that the fragment is at least 400 amino acids (aa), even more preferably that the fragment is at least 800 amino acids (aa), and most preferably that the fragment is at least 1200 amino acids (aa).

Using this standard protein-protein BLAST computer program, a orfF3 sequence as described herein is preferably a DNA sequence that encodes a polypeptide comprising a fragment of at least 200 amino acids (aa) that is at least 40% identical to a corresponding fragment of the orfF3 polypeptide sequence shown in positions 1-893 of SEQ ID NO 4, more preferably a DNA sequence that encodes a polypeptide comprising a fragment of at least 200 amino acids (aa) that is at least 50% identical to a corresponding fragment of the orfF3 polypeptide sequence shown in positions 1-893 of SEQ ID NO 4, even more preferably a DNA sequence that encodes a polypeptide comprising a fragment of at least 200 amino acids (aa) that is at least 65% identical to a corresponding fragment of the orfF3 polypeptide sequence shown in positions 1-893 of SEQ ID NO 4, and most preferably a DNA sequence that encodes a polypeptide comprising a fragment of at least 200 amino acids (aa) that is at least 80% identical to a corresponding fragment of the orfF3 polypeptide sequence shown in positions 1-893 of SEQ ID NO 4.

With the identity percentages given above, it is preferred that the fragment is at least 300 amino acids (aa), more preferably that the fragment is at least 400 amino acids (aa), even more preferably that the fragment is at least 800 amino acids (aa), and most preferably that the fragment is at least 1200 amino acids (aa).

Using this standard protein-protein BLAST computer program, a orfF4 sequence as described herein is preferably a DNA sequence that encodes a polypeptide comprising a fragment of at least 200 amino acids (aa) that is at least 40% identical to a corresponding fragment of the orfF4 polypeptide sequence shown in positions 1-1627 of SEQ ID NO 6, more preferably a DNA sequence that encodes a polypeptide comprising a fragment of at least 200 amino acids (aa) that is at least 50% identical to a corresponding fragment of the orfF4 polypeptide sequence shown in positions 1-1627 of SEQ ID NO 6, even more preferably a DNA sequence that encodes a polypeptide comprising a fragment of at least 200 amino acids (aa) that is at least 65% identical to a corresponding fragment of the orfF4 polypeptide sequence shown in positions 1-1627 of SEQ ID NO 6, and most preferably a DNA sequence that encodes a polypeptide comprising a fragment of at least 200 amino acids (aa) that is at least 80% identical to a corresponding fragment of the orfF4 polypeptide sequence shown in positions 1-1627 of SEQ ID NO 6.

With the identity percentages given above, it is preferred that the fragment is at least 300 amino acids (aa), more preferably that the fragment is at least 400 amino acids (aa), even more preferably that the fragment is at least 800 amino acids (aa), and most preferably that the fragment is at least 1200 amino acids (aa).

Alternatively, the homology may suitably be determined by means of computer programs known in the art such as GAP provided in the GCG program package (Program Manual for the Wisconsin Package, Version 8, Aug. 1994, Genetics Computer Group, 575 Science Drive, Madison, Wis., USA 53711) (Needleman, S. B. and Wunsch, C. D., (1970), Journal of Molecular Biology, 48, 443-453.

Using GAP with the following settings for polypeptide sequence comparison: GAP creation penalty of 3.0 and GAP extension penalty of 0.1, the preferred identity percentages given above in relation to the BLAST program are also the preferred identities when using GAP Hybridization The hybridization referred to above is intended to comprise an analogous DNA sequence which hybridizes to a double-stranded DNA probe. Suitable experimental conditions for determining hybridization at low, medium, or high stringency between a nucleotide probe and a homologous DNA or RNA sequence involve presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 mu g/ml of denatured sonicated salmon sperm DNA (Sambrook et al. 1989), followed by hybridization in the same solution containing 10 ng/ml of a random-primed (Feinberg, A. P. and Vogelstein, B. (1983) Anal. Biochem. 132:6-13), P-dCTP-labeled (specific activity>1×10 cpm/ mu g ) probe for 12 hours at 45° C. The filter is then washed twice for 30 minutes in 2×SSC, 0.5% SDS at a temperature of at least 55° C. (low stringency), more preferably at least 60° C. (medium stringency), still more preferably at least 65° C. (medium/high stringency), even more preferably at least 70° C. (high stringency), even more preferably at least 75° C. (very high stringency).

Molecules to which the oligonucleotide probe hybridizes under these conditions are detected using an X-ray film.

A Fermentable Material Comprising Proteins

The term "a material comprising proteins" in relation expressions such as "fermenting a material comprising proteins with a lactic acid bacteria" denotes herein any material comprising proteins wherein the lactic acid bacterium may growth and thereby make it possible to obtain a fermented material that comprises peptides. Peptides should be understood as peptides obtained by lactic acid bacteria cell wall proteinase based hydrolysis the proteins.

For example, a material comprising proteins may be a suitable standard lactic acid bacteria fermentation media such as M17 broth or MRS broth. Preferably the media comprises animal milk proteins preferably enumerated by, for example milk protein components, such as whole or defatted animal milk or milk casein.

Food Material

The food material should comprise animal milk proteins or vegetable proteins.

Preferably it comprises animal milk proteins preferably enumerated by, for example milk protein components, such as whole or defatted animal milk or milk casein.

Food material with vegetable proteins may preferably be enumerated by, for example corn, corn protein, wheat, wheat protein, soybean, defatted soybean or soybean protein.

Lactic Acid Bacterium

The term "lactic acid bacteria" denotes herein a group of Gram-positive, non-sporing bacteria, which carry out a lactic acid fermentation of sugars.

Among others, it includes species of lactic acid bacteria belonging to genus *Lactobacillus*, such as *Lactobacillus helveticus, Lactobacillus delbruekii* subsp. *bulgaricus*, etc., lactic acid bacteria belonging to genus Lactococcus, such as *Lactococcus lactis*, lactic acid bacteria belonging to genus Streptococcus, such as *Streptococcus salivarius* subsp. *thermophilus*, lactic acid bacteria belonging to genus Leuconostoc, such as *Leuconostoc lactis*, lactic acid bacteria belonging to genus Bifidobacterium, such as *Bifidobacterium longum* or *Bifidobacterium breve*, and lactic acid bacteria belonging to genus Pediococcus.

The lactic acid bacteria may be used as a mixture with other microorganisms, e.g. yeasts.

Numerous different lactic acid bacteria are publicly available to the skilled person. Reference is e.g. made to Deutsche Sammlung von Mikroorganismen und Zellkulturen GmbH (DSMZ); and the Internet taxonomy browser of NCBI.

In order to identify a suitable specific lactic acid bacterium, it is routine work for the skilled person to simply e.g. obtain an adequate amount of different public available bacteria and identify one or more specific strains, which comprise the gene sequence(s) as discussed herein. Preferably, this is done by a PCR amplification protocol as described herein.

Preferably, the lactic acid bacterium is a bacterium of the phylium Firmicutes, more preferably of the class *Bacilli*, even more preferably of the order Lactobacillales. Within this order a preferred lactic acid bacterium is a bacterium of the family Lactobacillaceae, more preferably of the genus *Lactobacillus*. Most preferably it is a *Lactobacillus helveticus* strain. For further details in relation to taxomony reference is made to (Bergey's Manual of Systematic Bacteriology, Second Edition, Volume 1: The Archea and the Deeply Branching and Phototrophic Bacteria).

A sample of a particular preferred *Lactobacillus helveticus* strain CHCC5951 has been deposited at DSMZ (Deutsche Sammlung von Mikroorganismen und Zellkulturen GmbH) under the accession number DSM 14998 with a deposit date of 15$^{th}$ May 2002. The deposit has been made under the conditions of the Budapest Treaty on the International Recognition of the Deposit of Microorganisms for the Purposes of Patent Procedure.

Accordingly, a particular preferred embodiment relates to a process as described herein wherein the lactic acid bacterium is *Lactobacillus helveticus* with the registration number DSM 14998.

In this relation, a separate aspect of the invention relates to a *Lactobacillus helveticus* bacterium with the registration number DSM 14998 or a mutant thereof.

Using as starting material the deposited the deposited DSM 14998 strain, the skilled reader can by conventional mutagenesis or re-isolation techniques obtain further mutants or derivatives which retain the ability to be suitable for preparing peptides with anti-hypertensive properties.

Further a sample of a *Lactobacillus helveticus* strain CHCC4080 has been deposited at DSMZ (Deutsche Sammlung von Mikroorganismen und Zellkulturen GmbH) under the accession number DSM 14997 with a deposit date of $15^{th}$ May 2002. The deposit has been made under the conditions of the Budapest Treaty on the International Recognition of the Deposit of Microorganisms for the Purposes of Patent Procedure.

Proteolytic Activity of the Lactic Acid Bacteria

The prtH200, orfF3 and orfF4 gene sequences as described herein may be seen as fingerprints highly suitable to identity useful lactic acid bacteria as described herein. Without being limited to theory, theoretically it may be that some strains could exist that despite comprising the fingerprint gene sequence(s) as described herein are not exhibiting the advantageous properties as described herein.

Accordingly, once having identified, in a lactic acid bacterium, the presence of fingerprint gene sequence(s) as described herein, it may be advantageous to test the proteolytic activity of the lactic acid bacterium. In the present context, a preferred lactic acid bacterium has preferably a proteolytic activity as described below.

In the present context, a lactic acid bacterium is considered to have proteolytic activity when it is capable of synthesizing an active cell wall proteinase. In other words, capable of proving a proteinase, which is active outside the intracellular part of the bacterium. Further, the proteinase should have a specificity making it capable of degrading proteins (e.g. casein comprised in milk) to obtain peptides with anti-hypertensive properties.

Preferably, the proteolytic activity of a bacterium is ascertained by a protocol comprising the steps:
  (i) fermenting overnight 200 ml of a food material with the bacterium,
  (ii) extracting the produced peptides, and
  (iii) measuring the anti-hypertensive properties of the extracted peptides by an assay measuring the peptidic concentration required to inhibit 50% of the ACE activity.

The ACE inhibition activity assay is herein also termed DL50. The lower the DL50 value is the better is the anti-hypertensive effect of the peptides comprised in the fermented food material.

In step (i) of the protocol, the food material is preferably fresh milk. Further, the bacterium is preferably inoculated to the food material in the form of an overnight stock culture of (1% v/v) and maintained overnight at a suitable temperature. A suitable temperature is a temperature that is suitable for growth of the bacterium. The skilled person knows how to identify this for a particular lactic acid bacterium. For *Lactobaccillus* species a suitable temperature is 37° C. and for *Lactococcus* species a suitable temperature is 30° C.

In working example 2 herein is provided a detailed preferred protocol for the fermenting and extracting steps and a detailed preferred protocol for the DL50 ACE activity assay.

Preferably, the lactic acid bacterium has a proteolytic activity making it capable of, in a protocol comprising the steps:
  (i) fermenting overnight 200 ml of a food material with the bacterium,
  (ii) extracting the produced peptides, and
  (iii) measuring the anti-hypertensive properties of the extracted peptides by an assay measuring the peptidic concentration required to inhibit 50% of the ACE activity (DL50), producing peptides with an angiotensin-converting enzyme (ACE) inhibition activity (DL50) of from 0.25 to 5.0 (mg/ml).

More preferably, the lactic acid bacterium is capable of producing peptides with an angiotensin-converting enzyme (ACE) inhibition activity (DL50) of from 0.25 to 4.0 (mg/ml), and even more preferably the proteolytic lactic acid bacterium is capable of producing peptides with an angiotensin-converting enzyme (ACE) inhibition activity (DL50) of from 0.25 to 3.5 (mg/ml).

The lower DL50 range may be, instead of 0.25 mg/ml, 1.0 mg/ml.

Fermentation

In the process of the present invention, the food material is fermented by lactic acid bacteria under operating conditions, which may be varied depending on the types of the food material and/or the combination of the lactic acid bacteria. Preferably, if the food material is not already an aqueous solution, food material is dissolved in a suitable aqueous solution, which is then admixed with lactic acid bacteria and cultivated by way of fermentation.

The culturing of the lactic acid bacteria may be performed by adding pre-cultured lactic acid bacteria starter to the food material medium, which may have been previously heat-sterilized and cooled to the predetermined temperature for incubation. The inoculation amount of the lactic acid bacteria starter may preferably be $10^5$ to $10^7$ cells of lactic acid bacteria/ml medium. The temperature for incubation is usually 20 to 50° C. and preferably 30 to 45° C. The incubation time is usually 3 to 48 hours and preferably 6 to 24 hours. Particularly, it is preferred to perform cultivation in the medium having pH in a range of 3.5 to 7, more preferably 5 to 6, in order to perform cultivation of lactic acid bacteria efficiently. Further, it is preferred to perform pH-stat cultivation maintaining pH in a range of 4 to 7. The incubation may be terminated, without restriction, when the number of lactic acid bacteria exceeds $10^8$ cells/ml.

A preferred embodiment relates to a process, as described herein, wherein the fermenting of the food material is performed under conditions, which produce from 0.5 to 25 mg peptides with anti-hypertensive properties per 100 ml of the food material, more preferably which produce from 1 to 5 mg peptides with anti-hypertensive properties per 100 ml of the food material.

Subsequent Purification of the Anti-hypertensive Peptides from the Fermented Food Material As stated above, the use of the lactic acid bacteria, as described herein, provides directly after the fermentation a useful amount of peptides with very good anti-hypertensive properties.

However, in some circumstances it may be preferred to perform a subsequent purification of the anti-hypertensive peptides from the fermented food material. This may for instance be when the peptides are to be used in a pharmaceutical tablet, which requires a very high concentration of the anti-hypertensive peptides.

Accordingly, an embodiment of the invention relates to a process for preparing peptides with anti-hypertensive properties of as described herein, wherein the fermented food material is further processed in a way that purify or up-concentrate the peptides with anti-hypertensive properties.

For instance, the fermented food material containing peptides with anti-hypertensive properties may be centrifuged, and the resulting supernatant may be subjected to purifying treatment with a reverse-phase resin, for obtaining a sample in which the content of the peptides with anti-hypertensive properties is increased.

The centrifugation may preferably be performed, for example, at 2,000 to 20,000 rpm for 1 to 20 minutes. The centrifugation may also be performed in a centrifugator.

The purifying treatment with a reverse-phase resin may be performed by absorption and elution of the peptides with a reverse-phase resin, and/or by reverse-phase chromatography, thereby increasing purity of the peptides.

For further technical details in relation to this reverse-phase resin protocol reference is made to EP821968.

Alternatively, the fermented food material is further processed in a way wherein a nanofiltration is performed on the fermented food material. This may be done in order to remove lactic acid or monovalent ions from the fermented food material.

For further technical details in relation to this nanofiltration protocol reference is made to WO01/32905.

A Functional Food Product Comprising Peptides with Anti-hypertensive Properties

As said above, the use of lactic acid bacteria comprising the prtH200 proteinases as described herein provides directly after the fermentation a useful amount of peptides with very good anti-hypertensive properties. Consequently, it is not considered necessary to further purify or up-concentrate the peptides from the fermented food material. The fermented food material may be packed directly and provided to the market as a functional food product or a food product additive, e.g. in a freeze-dried form.

In Example 6 this is demonstrated. In short, the results of Example 6 show that fermented milk in itself without any further treatment has good blood pressure reducing effects. Further freeze-dried fermented milk could be suspended in neutral milk and thereby give a suitable functional food product. The freeze-dried fermented milk could therefore be seen as a suitable food additive product.

Accordingly, an embodiment of the invention relates to a process for preparing a functional food product comprising peptides with anti-hypertensive properties, the process comprising following steps:
(i) preparing a fermented food material according to a process for preparing peptides with anti-hypertensive properties as described herein,
(ia) drying the fermented food material, and
(ii) packing it in a suitable way to get a functional food product.

Step (ia) is preferably freeze drying.

In other words, since there is no need for further treatment of the final functional food product it may also be characterized by it comprises a substantial part of the lactic acid bacteria that were present during the fermentation. Example 6 clearly demonstrates that such a product works fine and since lactic acid bacteria are know to be beneficial in a number of contexts it might actually be an advantage that such lactic acid bacteria are present in the functional food product.

Accordingly, an embodiment of the invention relates to a process for preparing a functional food product comprising peptides with anti-hypertensive properties, the process comprising following steps:
(ii) preparing a fermented food material according to a process for preparing peptides with anti-hypertensive properties as described herein,
(ia) keeping at least a part of the lactic acid bacteria present during the fermentation in the fermented food material, and
(ii) packing it in a suitable way to get a functional food product.

The term "keeping at least a part of the lactic acid bacteria present during the fermentation in the fermented food material" should be understood in view of above explaining that it is not considered necessary to remove the lactic acid bacteria. Some of the bacteria may be removed. Quantitatively, it may be expressed as keeping at least a 5% part of the lactic acid bacteria present during the fermentation in the fermented food material or keeping at least a 20% part of the lactic acid bacteria present during the fermentation in the fermented food material.

As shown in example 6 the lactic acid bacteria kept in the functional food product may be dead or alive, since a heat-treated fermented food material also had good blood reducing properties.

It may be preferred to perform a subsequent purification of the anti-hypertensive peptides from the fermented food material.

Accordingly, an embodiment of the invention relates to a process for preparing a functional food product comprising peptides with anti-hypertensive properties, the process comprising following steps:
(iii) preparing a fermented food material according to a process for preparing peptides with anti-hypertensive properties as described herein,
(ia) the fermented food material of step (i) is further processed in a way that purify or up-concentrate the peptides with anti-hypertensive properties according to a process as described above,
(ib) the purified or up-concentrated peptides of step (ia) is then added to a food material, and
(iv) packing it in a suitable way to get a functional food product.

Preferably, the food material of step (ib) is a fermented food material prepared according to a process as described herein. This corresponds to a situation where one wants a relatively high concentration of the peptides with anti-hypertensive properties in the functional food product.

Use and Preferred Doses of the Peptides with Anti-hypertensive Properties

The peptides with anti-hypertensive properties, obtained by a process of the present invention, are usually a mixture of peptides, and may contain other peptides. For use as foods and drinks, the fermented food material containing the petides and/or purified products thereof may be used directly. Alternatively, the agent may be powdered by freeze drying, spray drying or drum dryer drying, before use.

A preferred effective amount of the anti-hypertensive peptides of the present invention varies depending upon the age and condition of a person, and is in a range of 0.05 to 10 mg/kg body weight/day. It is preferable to administer 0.3 to 3.0 mg/kg body weight/day. If the dose is not less than 0.05 mg/kg body weight/day, sufficient effect may be expected. If the dose is not more than 10 mg/kg body weight/day, the effect may be exhibited efficiently.

Use for Cholesterol Lowering Therapy

The article (Teo, K. et al, Circulation (2000) 102:1748-1754) describes that ACE inhibition drugs (EnalApril) may have a positive effect in a cholesterol lowering therapy in particular in reducing coronary atherosclerotic disease.

Accordingly, a separate aspect of the invention relates to use of peptides with anti-hypertensive properties obtained by a process of the present invention for the manufacture of a medicament or a functional food product for use in a cholesterol lowering therapy in particular in relation to reducing coronary atherosclerotic disease.

Claim Presentation of Aspects and Embodiments

Aspects and embodiments of the invention may be presented in a so-called claim format. Some aspect and embodiments of the invention are given below is such a claim format.

1. A method for obtaining a lactic acid bacterium comprising
    (i) investigating whether a lactic acid bacterium is a lactic acid bacterium that comprises a gene sequence encoding a cell wall proteinase (termed prtH200) wherein the gene sequences is identifiable by PCR amplification of genomic DNA of the lactic acid bacterium using sets of PCR primers selected from the group consisting of [sense sequence (S); antisense sequence (A)]:

```
PrtH200:
 (a): (S): 5' CGATGATAATCCTAGCGAGC3', (A): 5' TGGCAGAACCTGTGCCTA 3';

(b): (S): 5' GCCAAGACGCCTCTGGTA 3', (A): 5' TAGGTATAGTTTCCATCAGGA 3'; and (c): (S): 5' AARGTWCCWTAYGGYYWYAAYTA 3', (A): 5' GCCATDSWDGTRCCDSWCATDTK 3'; and
```

(ii) if the lactic acid bacterium fulfills the criteria of step (i) then the lactic acid bacterium culture is obtained; or
    (iii) if the lactic acid bacterium does not fulfill the criteria of step (i) then repeat step (i) with another lactic acid bacterium.

2. The method for obtaining a lactic acid bacterium of claim 1, wherein step (i) also comprises investigating whether the lactic acid bacterium comprises a gene sequence (termed orfF3) encoding an open reading frame wherein the gene sequences is identifiable by PCR amplification of genomic DNA of the lactic acid bacterium using sets of PCR primers selected from the group consisting of [sense sequence (S); antisense sequence (A)]:

```
orfF3:
 (a): (S): 5' CGAAGGCGATAAGTCAAACTTTGATAATGC 3', (A): 5' CCCGGTTCTGTAAGATAATTTGGATCG 3'; and (b): (S): 5' ASTCWRRYTTYGATRATGCW 3', (A): 5' BHKYAMSAWARTTTGGATCR 3'.
```

3. A method for obtaining a lactic acid bacterium comprising
    (i) investigating whether a lactic acid bacterium is a lactic acid bacterium that comprises a gene sequence encoding a cell wall proteinase (termed prtH200), wherein the gene sequence is defined as prtH200 is a DNA sequence encoding an enzyme exhibiting cell wall proteinase activity, which DNA sequence is selected from the group consisting of:
   (a) the DNA sequence shown in positions 1-5550 in SEQ ID NO 1;
   (b) a DNA sequence comprising a fragment of at least 75 base pairs (bp) that is at least 50% identical to a corresponding fragment of the DNA sequence defined in (a);
   (c) a DNA sequence that encodes a polypeptide, exhibiting cell wall proteinase activity, comprising a fragment of at least 200 amino acids (aa) that is at least 30% identical to a corresponding fragment of the polypeptide sequence shown in positions 1-1849 of SEQ ID NO 2;
   (d) a DNA sequence which hybridizes with a double-stranded DNA probe comprising the DNA sequence shown in positions 1-5550 in SEQ ID NO 1 at low stringency; and
   (e) a DNA sequence which is a fragment of the DNA sequences specified in (a), (b), (c), or (d);
    (ii) if the lactic acid bacterium fulfills the criteria of step (i) then the lactic acid bacterium is obtained; or
    (iii) if the lactic acid bacterium does not fulfill the criteria of step (i) then repeat step (i) with another lactic acid bacterium.

4. The method for obtaining a lactic acid bacterium of claim 3, wherein step (i) also comprises investigating whether the lactic acid bacterium comprises a gene sequence encoding an open reading frame (termed orfF3), wherein the gene sequence is defined as orfF3 is a DNA sequence encoding an open reading frame, which DNA sequence is selected from the group comprising of:
   (a) the DNA sequence shown in positions 1-2679 in SEQ ID NO 3;
   (b) a DNA sequence comprising a fragment of at least 75 base pairs (bp) that is at least 40% identical to a corresponding fragment of the DNA sequence defined in (a);
   (c) a DNA sequence that encodes a polypeptide comprising a fragment of at least 200 amino acids (aa) that is at least 30% identical to a corresponding fragment of the polypeptide sequence shown in positions 1-893 of SEQ ID NO4;
   (d) a DNA sequence which hybridizes with a double-stranded DNA probe comprising the DNA sequence shown in positions 1-5550 in SEQ ID NO 3 at low stringency; and
   (e) a DNA sequence which is a fragment of the DNA sequences specified in (a), (b), (c), or (d).

5. The method for obtaining a lactic acid bacterium of any of claims 1 to 4, wherein the lactic acid bacterium has a proteolytic activity making it capable of, in a protocol comprising the steps:
   (i) fermenting overnight 200 ml of a food material with the bacterium;
   (ii) extracting the produced peptides, and
   (iii) measuring the anti-hypertensive properties of the extracted peptides by an assay measuring the peptidic concentration required to inhibit 50% of the ACE activity (DL50), producing peptides with an angiotensin-converting enzyme (ACE) inhibition activity (DL50) of from 0.25 to 5.0 (mg/ml).

6. The method for obtaining a lactic acid bacterium of any of the preceding claims, wherein the lactic acid bacterium is a bacterium of the phylum Firmicutes, more preferably of the class *Bacilli*, even more preferably of the order Lactobacillales.

7. The method for obtaining a lactic acid bacterium of claim 6, wherein the bacterium, of the order Lactobacillales, is a bacterium of the family Lactobacillaceae, more preferably of the genus *Lactobacillus*, and even more preferably a *Lactobacillus helveticus* bacterium.

8. The method for obtaining a lactic acid bacterium of claim 7, wherein the bacterium is a *Lactobacillus helveticus* bacterium with the registration number DSM 14998 or a mutant thereof.

9. A process for preparing peptides with anti-hypertensive properties, the process comprising fermenting a food material, comprising animal milk proteins or vegetable proteins, with a lactic acid bacterium to obtain a fermented food material which comprises the peptides with anti-hypertensive properties, characterized in that the lactic acid bacterium comprises a gene sequence encoding a cell wall proteinase (termed prtH200) wherein the gene sequences is identifiable by PCR amplification of genomic DNA of the lactic acid bacterium using sets of PCR primers selected from the group consisting of [sense sequence (S); antisense sequence (A)]:

```
PrtH200:
(a): (S): 5' CGATGATAATCCTAGCGAGC3',
    (A): 5' TGGCAGAACCTGTGCCTA 3';
(b): (S): 5' GCCAAGACGCCTCTGGTA 3',
    (A): 5' TAGGTATAGTTTCCATCAGGA 3'; and
(c): (S): 5' AARGTWCCWTAYGGYYWYAAYTA 3',
    (A): 5' GCCATDSWDGTRCCDSWCATDTK 3'.
```

10. The process for preparing peptides with anti-hypertensive properties of claim 10, wherein the lactic acid bacterium also comprises a gene sequence (termed orfF3) encoding an open reading frame wherein the gene sequences is identifiable by PCR amplification of genomic DNA of the lactic acid bacterium using sets of PCR primers selected from the group consisting of [sense sequence (S); antisense sequence (A)]:

```
orfF3:
(a): (S): 5' CGAAGGCGATAAGTCAAACTTTGATAATGC 3',
    (A): 5' CCCGGTTCTGTAAGATAATTTGGATCG 3'; and
(b): (S): 5' ASTCWRRYTTYGATRATGCW 3',
    (A): 5' BHKYAMSAWARTTTGGATCR 3'.
```

11. A process for preparing peptides with anti-hypertensive properties, the process comprising fermenting a food material, comprising animal milk proteins or vegetable proteins, with a lactic acid bacterium to obtain a fermented food material which comprises the peptides with anti-hypertensive properties, characterized in that the lactic acid bacterium comprises a gene sequence encoding a cell wall proteinase (termed prtH200), wherein the gene sequence is defined as prtH200 is a DNA sequence encoding an enzyme exhibiting cell wall proteinase activity, which DNA sequence is selected from the group consisting of:

(a) the DNA sequence shown in positions 1-5550 in SEQ ID NO 1;

(b) a DNA sequence comprising a fragment of at least 75 base pairs (bp) that is at least 50% identical to a corresponding fragment of the DNA sequence defined in (a);

(c) a DNA sequence that encodes a polypeptide, exhibiting cell wall proteinase activity, comprising a fragment of at least 200 amino acids (aa) that is at least 30% identical to a corresponding fragment of the polypeptide sequence shown in positions 1-1849 of SEQ ID NO 2;

(d) a DNA sequence which hybridizes with a double-stranded DNA probe comprising the DNA sequence shown in positions 1-5550 in SEQ ID NO 1 at low stringency; and (e) a DNA sequence which is a fragment of the DNA sequences specified in (a), (b), (c), or (d).

12. The process for preparing peptides with anti-hypertensive properties of claim 11, wherein the lactic acid bacterium also comprises a gene sequence encoding an open reading frame (termed orfF3), wherein the gene sequence is defined as orfF3 is a DNA sequence encoding an open reading frame, which DNA sequence is selected from the group comprising of:

(a) the DNA sequence shown in positions 1-2679 in SEQ ID NO 3;

(b) a DNA sequence comprising a fragment of at least 75 base pairs (bp) that is at least 40% identical to a corresponding fragment of the DNA sequence defined in (a);

(c) a DNA sequence that encodes a polypeptide comprising a fragment of at least 200 amino acids (aa) that is at least 30% identical to a corresponding fragment of the polypeptide sequence shown in positions 1-893 of SEQ ID NO4;

(d) a DNA sequence which hybridizes with a double-stranded DNA probe comprising the DNA sequence shown in positions 1-2679 in SEQ ID NO 3 at low stringency; and (e) a DNA sequence which is a fragment of the DNA sequences specified in (a), (b), (c), or (d).

13. A process for preparing peptides comprising
(i) obtaining a lactic acid bacterium by a method for obtaining a lactic acid bacterium according to any of claims 1 8;
(ii) fermenting a material comprising proteins with the lactic acid bacterium obtained in (i) to obtain a fermented material which comprises the peptides.

14. The process for preparing peptides of claim 13, wherein the process is a process for preparing peptides with anti-hypertensive properties comprising
(i) obtaining a lactic acid bacterium by a method for obtaining a lactic acid bacterium according to any of claims 1 8;
(ii) fermenting a food material, comprising animal milk proteins or vegetable proteins, with the lactic acid bacterium obtained in (i) to obtain a fermented food material which comprises the peptides with anti-hypertensive properties.

15. The process for preparing peptides of any of claims 9 to 14, wherein the food material comprises animal milk proteins.

16. The process for preparing peptides of claim 15, wherein an animal milk protein is casein.

17. The process for preparing peptides of claim 15, wherein the food material is milk or milk based material.

18. The process for preparing peptides of any of the claims 9 to 17, wherein the lactic acid bacterium has a proteolytic activity making it capable of, in a protocol comprising the steps:
   (iv) fermenting overnight 200 ml of a food material with the bacterium;
   (v) extracting the produced peptides, and
   (vi) measuring the anti-hypertensive properties of the extracted peptides by an assay measuring the peptidic concentration required to inhibit 50% of the ACE activity (DL50), producing peptides with an angiotensin-converting enzyme (ACE) inhibition activity (DL50) of from 0.25 to 5.0 (mg/ml).

19. The process for preparing peptides of any of the claims 9 to 18, wherein the lactic acid bacterium is a bacterium of the phylium Firmicutes, more preferably of the class *Bacilli*, even more preferably of the order Lactobacillales.

20. The process for preparing peptides of claim 19, wherein the bacterium, of the order Lactobacillales, is a bacterium of the family Lactobacillaceae, more preferably of the genus *Lactobacillus*, and even more preferably a *Lactobacillus helveticus* bacterium.

21. The process for preparing peptides of claim 20, wherein the bacterium is a *Lactobacillus helveticus* bacterium with the registration number DSM 14998 or a mutant thereof.

22. The process for preparing peptides of any of the claims 9 to 21, wherein the fermenting of the food material is performed under conditions, which produce from 0.5 to 25 mg peptides with anti-hypertensive properties per 100 ml of the food material.

23. The process for preparing peptides of any of the claims 9 to 22, wherein the fermenting of the food material is performed at 20 to 50° C. for 3 to 48 hours.

24. The process for preparing peptides of any of the claims 9 to 23, wherein the fermenting of the food material is performed under conditions wherein the pH is in a range from pH 3.5 to 7.

25. The process for preparing peptides of any of the claims 9 to 24, wherein the fermented food material is further processed in a way that purify or up-concentrate the peptides with anti-hypertensive properties.

26. The process for preparing peptides of claim 25, wherein the fermented food material is centrifuged and the obtained supernatant, comprising the peptides with anti-hypertensive properties, is isolated.

27. The process for preparing peptides of claim 26, wherein the peptides are purified from the supernatant with a reverse-phage resin.

28. The process for preparing peptides of claim 25, wherein a nanofiltration is performed on the fermented food material.

29. A process for preparing a functional food product comprising peptides with anti-hypertensive properties, the process comprising following steps:
   (i) preparing a fermented food material according to a process of any of claims 9 to 24, and
   (ii) packing it in a suitable way to get a functional food product.

30. The process for preparing a functional food product of claim 29, comprising following further intermediate steps [between steps (i) and (ii)]:
   (ia) the fermented food material of step (i) of claim 20 is further processed in a way that purify or up-concentrate the peptides with anti-hypertensive properties according to a process of any of claims 25 to 28,
   (ib) the purified or up-concentrated peptides of step (ia) is then added to a food material.

31. The process for preparing a functional food product of claim 30, wherein the food material of step (ib) of claim 21 is a fermented food material prepared according to a process of any of claims 9 to 24.

32. Peptides with anti-hypertensive properties obtainable by a process for preparing peptides with anti-hypertensive properties of any of claims 25-28.

33. A functional food product comprising peptides with anti-hypertensive properties obtainable by a process for preparing a functional food product of any of claims 29 to 31.

34. Use of peptides with anti-hypertensive properties of claim 32 for the manufacture of a medicament for the treatment of hypertension.

35. Use of a functional food product comprising peptides with anti-hypertensive properties of claim 33 for the manufacture of a medicament for the treatment of hypertension.

36. A *Lactobacillus helveticus* bacterium with the registration number DSM 14998 or a mutant thereof.

EXAMPLES

If not otherwise mentioned, individual steps were performed using standard methods as e.g. described in the general textbooks (Maniatis, T., Fritsch, E. F., Sambrook, J. "Molecular Cloning. A laboratory manual". Cold Spring Harbor Laboratories, 2nd Edition/3 Volume, 1989; Ausubel, F. M., et al. (eds.)"Current Protocols in Molecular Biology". John Wiley and Sons, 1995.

Example 1

PCR Amplification Reaction

Template DNA was obtained by phenol-chloroform extraction as previously described (Marmur (1961, *Journal of Molecular Biology*, 3, 208-218). The final preparation was genomic template DNA in a TE buffer+RNAse.

The PCR reaction was prepared as follows:
(i) 1.0 µl of template DNA
   1.0 µl of forward primer (5 pmol/µl)
   1.0 µl of reverse primer (5 pmol/µl)
   1.0 µl 2.5 mM dNTD (mixture of dATP, dCTP, dGTP, dTTP)
   5.0 µl Mg buffer (20 mM MgS04)
   0.5 µl DNA polymerase (Pwo, 100 U)
   10.5 µl H20
(ii) The thermal program for the PCR amplification was 30 cycles of 1 min at 94° C., 90 s at 50° C. (when primers Tm was around 55° C.), 90 s at 55° C. (when primers Tm was around 62° C.), 90 s at 45° C. (when primers Tm was around 50° C.) and 1 min at 72° C . The samples were cooled to 4° C. after the 30 cycles were completed.
(iii) The PCR products were run on a 1.5% agarose gel at 60 V, excised from the gel under UV light and purified using a QIAquick Gel Extraction Kit according to the manufacturer's instructions (Qiagen, Cat. No. 28704).

Example 2

Proteolytic (ACE) Activity Assay

Preparation of Stock Culture

*Lactobacillus* species were streaked on MRS agar and incubated anaerobically for 48 h at 37° C. A single colony was picked, inoculated into MRS broth and grown overnight at 37° C. *Lactococcus* species were streaked on M17 agar and incubated aerobically for 48 h at 30° C. A single colony was picked, inoculated into M17 broth and grown overnight at 30° C. Stock cultures were prepared from these overnight cultures and were stored at −80° C. in 20% glycerol.

Preparation of Fermented Milk and Extraction of Peptides

Fermentation is performed by inoculate 200 ml of fresh milk with an overnight stock culture of example 1 (1% v/v) and maintain overnight at 37° C. or 30° C. dependent on the strain used.

From the fermented milk, extraction of the peptides may be achieved by using the following protocol:

Centrifuge at 3000 g for 10 min at room temperature.
Withdraw the supernatant and adjust to pH 8.3 (optimal pH for ACE activity test) with NaOH.
Centrifuge the obtained supernatant at 3000 g for 10 min at room temperature.
Withdraw the supernatant (whey), which comprises the peptides.
Determine the concentration of peptides in the whey by the Lowry test (mg peptide/ml whey) (Lowry et al, 1951. *J. Biol. Chem.*, 193:265-275).

The whey may be used directly for ACE assay or freeze at −20° C. The whey comprising the peptides is termed "peptide solution" in example 3.

ACE Activity Assay

The peptide pools of milk fermented are tested for ACE activity in vitro. The DL50 (mg/ml) is the peptidic concentration, which inhibits 50% of ACE activity. The lower this value is, the better the anti-hypertensive effect of the fermented milk. The ACE activity of the extracted peptides is measured by the following protocol:

The essence of the assay is that ACE degrades a hippuryl-L-histidyl-L-leucine (HHL) substrate and adding a colour agent develops a colour. If peptides are present the peptides inhibit ACE and less HHL substrate is degraded. This means less colour is developed after addition of the colour agent.

Solution preparation:
Incubation buffer: 188 mmol/l boric acid pH 8.3, 1.375 mmol/l potassium chloride. (Dissolve 2.91 g of boric acid and 25.63 g potassium chloride in 200 ml of distilled water. Adjust the pH to 8.3 with 1 mol/l potassium hydroxide and dilute to 250 ml with distilled water. Store at room temperature).
Substrate solution: 5.8 mmol/l hippuryl-L-histidyl-L-leucine (HHL). (Dissolve 250 mg hippuryl-L-histidyl-L-leucine in about 90 ml incubation buffer and fill up to 100 ml with the same buffer. Store at 40° C. The substrate solution can be used for at least 2 weeks).
Stop solution: 100 mmol/l HEPES pH 9, 2.5 mmol EDTA. (Dissolve 23.83 g HEPES and 0.93 g EDTA in 800 ml distilled water. Adjust to pH 9 with 1 mol/l sodium hydroxide and dilute to 1 l with distilled water. Store at room temperature).
Colour reagent: 136 mmol/l cyanuric chloride in 1,4-dioxane. (Dissolve 12.50 g cyanuric chloride in about 400 ml of 1,4-dioxane and fill up with 1,4-dioxane to 500 ml. Store at room temperature in dark-brown glass bottle).

Assay: (all solutions are equilibrated to room temperature)
Make a dilution series of the peptide solution with incubation buffer. The series consist of 6 dilutions going from the undiluted peptide solution to a blank (only incubation buffer)
For each of the dilutions, place 10 µl of peptide solution, 40 µl of substrate (HHL) solution (2.5 g/l) and 2.5 µl of ACE (0.25 Units/ml) in a glass tube.
The positive control comprises 2.5 µl ACE, 10 µl of incubation and 40 µl of substrate (HHL)
The negative control comprises 12 µl of incubation buffer and 40 µl of substrate (HHL)
Incubate at 37° C. for 1 hour.
Stop the reaction by adding 300 µl of stop solution, followed by 150 µl of colour reagent
Mix vigorously.
Allow to stand for 5 minutes and centrifuge at 3300 g for 30 min at room temperature to remove denatured protein and excess cyanuric chloride.
Transfer 300 µl of supernatant of each sample to microtiter plate hole.
Read at 405 nm against water as a blank.

The ACE inhibition percentage is expressed by the formula:

$$ACE \text{ inhibition activity} = \frac{OD405 \text{ nm positive control} - OD405 \text{ nm sample}}{OD405 \text{ nm positive control} - OD405 \text{ nm negative control}}$$

Each dilution has its own ACE inhibition percentage value that gives a curve expressing the ACE inhibition percentage in function of the peptide concentration of the whey. DL50 (peptidic concentration that inhibits 50% of ACE activity) is obtained by reading the peptidic concentration at the intersection point between the curve and the corresponding 50% ACE inhibition point on the axe.

Example 3

Investigation of Presence of the prtH200, orfF3 and orfF4 Gene Sequences in Different Bacteria Different lactic acid bacterial strains were investigated for the presence of the prtH200, orfF3 and orfF4 gene sequences. PCR reactions were performed as described in Example 1. Table 1a shows peptides and PCR primers used to investigate for presence of a prtH200 gene encoding a proteinase. Table 1b shows peptides and PCR primers used to investigate for presence of a orfF3 gene. Table 1c shows peptides and PCR primers used to investigate for presence of a orfF4 gene.

In these tables are also given the estimated length of these amplified sequences. The estimated length was determined based on prtH200 SEQ ID NO 1, orfF3 SEQ ID NO 3 and orfF4 SEQ ID NO 5.

TABLE 1a (prtH200 proteinase)

| Primer set number | Sequence | | Estimated length of PCR fragment |
|---|---|---|---|
| (a) | (S): | 5' CGATGATAATCCTAGCGAGC3', | 620 bp |
|  | (A): | 5' TGGCAGAACCTGTGCCTA 3' |  |
| (b) | (S): | 5' GCCAAGACGCCTCTGGTA 3', | 313 bp |
|  | (A): | 5' TAGGTATAGTTTCCATCAGGA 3' |  |
| (c) | (S): | 5' AARGTWCCWTAYGGYYWYAAYTA 3', | 624 bp |
|  | (A): | 5' GCCATDSWDGTRCCDSWCATDTK 3' |  |

TABLE 1b

(orfF3 proteinase)

| Primer set number | Sequence | Estimated length of PCR fragment |
|---|---|---|
| (a) | (S): 5' CGAAGGCGATAAGTCAAACTTTGATAATGC 3', | 1605 bp |
|  | (A): 5' CCCGGTTCTGTAAGATAATTTGGATCG 3' |  |
| (b) | (S): 5' ASTCWRRYTTYGATRATGCW 3', | 1587 bp |
|  | (A): 5' BHKYAMSAWARTTTGGATCR 3'. |  | sense sequence (S),
antisense sequence (A)

TABLE 1c

(orfF4 proteinase)

| Primer set number | Sequence | Estimated length of PCR fragment |
|---|---|---|
| (a) | (S): 5' GGTGTTGCTCCTGAAGC 3' | 950 |
|  | (A): 5' ACTCTAGCACCAGCTAATTGAACATCATG 3 |  | sense sequence (S),
antisense sequence (A)

Table 2 shows the results of the PCR based investigations.

TABLE 2

| Species | Ref (CHCC) | p: (a) | p: (b) | p: (c) | o3: (a) | o3: (b) | o4 (a) |
|---|---|---|---|---|---|---|---|
| Lb. helveticus | 5951 | + | + | + | + | + | + |
| Lb. helveticus | 4080 | − | − | − | − | − | − |
| Lb. helveticus | 3610 | + | + | + | − | − | ? |
| Lb. helveticus | 637 | − | − | − | + | ? | + |
| Lb. helveticus | 3552 | − | − | − | − | ? | + |
| Lb. helveticus | DSM 13137 | − | − | ? | + | ? | + |

"p:" is prtH200 primer sets.
"o3:" is orfF3 primer sets.
"o4:" is orfF4 primer sets.
"+" denote a positive PCR fragment.
"−" denotes no PCR fragment or a negative PCR fragment.
"?" denotes not tested.
"Lb. helveticus DSM 13137" is described in WO01/32836 (Valio Ltd).

The positive fragments of Table 2 were within the expected size given in Table 1. They were all DNA sequenced and confirmed to comprise a DNA sequence corresponding to an expected DNA sequence.

The specific strain with ref number 5951 comprises prtH200, orfF3 and orfF4 gene sequences according to the present invention.

Example 4

ACE Activity

Cultures of the strains mentioned in Example 3 were tested in proteolytic (ACE) activity test as described in Example 2. Table 3 gives the results.

TABLE 3

| Culture used | Anti-hypertensive effect with DL 50 (mg/ml). Average of three determinations |
|---|---|
| Lb. helveticus 5951 | 2.99 |
| Lb. helveticus 4080 | 2.34 |
| Lb. helveticus 637 | 3.32 |

Example 5

In vivo Test of Anti-hypertensive Properties

Materials and Methods

Strains and Cultivation

Strains were streaked on MRS agar and incubated anaerobically for 48 h at 37° C. A single colony was picked, inoculated into MRS broth and grown overnight at 37° C. Stock cultures were prepared from this overnight culture and were stored at −80° C. in 20% glycerol. The strains were precultivated in milk overnight and inoculated 1% (v/v) in fresh milk for the fermentation.

Preparation of the Samples

Concentrated fermented milk:

The milk was fermented with the strains of single or mixed cultures for 16 hours with an inoculation level of 1% (v/v). The total product was freeze-dried. A second fermentation, with the same conditions as the first one, was centrifuged. The pellet was discarded and the whey was filtered through a 0,45 mm filter and frozen. The whey was used to solubilize the freeze-dried powder to concentrate it with a factor 5 before feeding the rats.

Spontaneously Hypertensive Rats:

Spontaneously Hypertensive Rats (SHR) was obtained from IFFA CREDO (a Charles River company), Lyon, France.

All treatments (fermented products) were administered between 09:00 h and 09:15 h by gavages at a dose of 2 ml of product.

Experimental Design:

Three groups were formed:

Group 1 (n=16): receiving treatment 1 (milk; n=16)
Group 2 (n=12): receiving successive treatment 2-7, each administration separated by a 3-day washout period
Group 3 (n=12): receiving successive treatment 8-12, each administration separated by a 3-day washout period Investigated Parameters:
Systolic blood pressure was determined by plethysmography in conscious SHR before as well as 5 and 24 hours after gavages, at the different times described below.
Prior to the experiments all SHR were acclimated to the animal facilities for 9 weeks. Moreover, all animals were accustomed to gavage and measurement of systolic blood pressure 3 days before the first gavage.
Systolic blood pressure of Group 1 was determined parallel to those of groups 2 and 3 and serves as control.
The day of the gavage systolic blood pressure was determined before as well as 6 and 24 hours after gavage.

Results

In table 4 is shown the variation of systolic blood pressure determined 5 and 24 hours after administration of different substances.

TABLE 4

|  | Milk | Tap water | Enalapril | Calpis commercial product | CHCC 4080 | CHCC 5951 | CHCC 637 |
| --- | --- | --- | --- | --- | --- | --- | --- |
| 5 hours | −4 | −4 | −30 | −13 | −14 | −18 | −8 |
| 24 hours | −4 | −2 | −17 | +2 | −1 | −19 | −8 |

Milk: this sample is non fermented milk, 9.5% reconstituted skim milk.

Enalapril: Enalapril is a medicine usually used to treat patients with high blood pressure. It was added to the milk at the high concentration of 20 mg/kg, to test the capacity of the rats to react to an anti-hypertensive compound.

Calpis commercial product: It is a commercial product of Calpis Food Industry. The name of the product is called Calpis. It is liquid fermented milk with a mixture of *Lb. helveticus* and *Saccharomyces cerevisiae* strains.

CHCC 4080: Concentrated fermented milk with CHCC 4080

CHCC 5951: Concentrated fermented milk with CHCC 5951

CHCC 637: Concentrated fermented milk with CHCC 637

The results demonstrate that CHCC 5951 is the lactic acid bacteria strain that is capable of making peptides with the best anti-hypertensive properties. Table 2 (above) shows that this strain comprises the prtH200, orfF3 and orfF4 genes as described herein. At 24 hours the peptides produced by use of the CHCC 5951 strain had an effect comparable to the medicament Enalapril.

CHCC 4080 comprises none of the genes. CHCC 637 comprises orfF3 and orfF4 but not prtH200.

As said above, a commercial product of Calpis Food Industry are made by using the CP790 lactic acid bacterium and this strain does not comprise prtH200 [Yamamoto et al (2000)].

Example 6

Further in vivo Tests using the CHCC5951 Strain

Strains and Cultivation and SHR Rats: The same as in Example 5

Preparation of the Samples
Fermented milk:
The milk was fermented with the strains of single or mixed cultures for 16 hours with an inoculation level of 1% (v/v). The total product was freeze-dried. A second fermentation, with the same conditions as the first one, was centrifuged. The pellet was discarded and the whey was filtered through a 0,45 mm filter and frozen. The whey was used to solubilize the freeze-dried powder to concentrate it with different factors before feeding the rats.

Experimental Design:
Animals: Spontaneously Hypertensive Rats (22 week old).
Groups:
1) Placebo (Milk)
2) Sample 1 (Fermented milk administered at 3 different whey concentrated 3 doses. Dose 1: factor 1, Dose 2: factor 2.5, Dose 3: factor 5)
3) Sample 2 (freeze-dried fermented milk suspended in neutral pH milk)
4) Sample 3 (just the fermented milk product)
5) Sample 4 (Fermented milk that was heat treated after fermentation)
6) Sample 5 (milk that had not been fermented but it included the live bacteria)

All treatments were administered between 10:00$^h$ and 10:05$^h$ by gavage at a dose of 2 ml of product.

Investigated Parameters: Systolic blood pressure was determined for 24 hours after gavage by telemetry (Data Sciences Int.) in conscious SHR at different time points In brief, the mean (over a 1 minute period) of systolic, diastolic blood pressures were recorded every 15 minutes, the 24 hours before administration and the 48 hours after administration. From these tracings, 24 hours mean of systolic and diastolic blood pressures were calculated in each group. Furthermore, the variations induced by each substance compared to placebo of the same parameters, i.e. over 24 hours, and during the 3 to 6, the 12 to 15 and the 21 to 24 hours after gavage, were calculated.

Prior to the experiments all SHR were acclimated to the animal facilities for 9 weeks. Moreover, all animals were accustomed to gavage the 3 days before the first administration of the substance.

Statistics.

All results are expressed as mean±standard error of mean.

Result table.

TABLE 1

Systolic blood pressure after gavage

| Groupe | Period | | | | Variation vs. untreated 1 | | | |
|---|---|---|---|---|---|---|---|---|
| | 0-24 | 3-6 | 1 | 2 | 0-24 | 3-6 | 12-15 | 2 |
| Placebo 1 | 184 ± 6 | 184 ± 6 | 183 ± 5 | 190 ± 8 | | | | |
| Sample 1 | | | | | | | | |
| Dose 1 | 178 ± 4* | 172 ± 4* | 176 ± 5* | 184 ± 7 | — | — | — | — |
| Dose 2 | 178 ± 4* | 175 ± 5* | 172 ± 4* | 184 ± 5 | — | −9.6 ± 2.7 | — | — |
| Dose 3 | 178 ± 3* | 174 ± 4* | 175 ± 3* | 186 ± 4 | — | — | — | — |
| | | | | | Variation vs. untreated 2 | | | |
| Placebo 2 | 176 ± 9 | 169 ± 9 | 179 ± 9 | 161 ± 9 | | | | |
| Sample 2 | 169 ± 9* | 163 ± 9* | 172 ± 7* | 166 ± 9* | — | −5.9 ± 2.7 | — | — |
| Sample 3 | 170 ± 8* | 168 ± 9 | 169 ± 7* | 165 ± 8* | — | −0.6 ± 3.1 | — | — |
| Sample 4 | 170 ± 8 | 167 ± 9 | 172 ± 8 | 168 ± 8 | — | −1.3 ± 4.4 | — | — |
| Sample 5 | 180 ± 10 | 180 ± 14 | 181 ± 8 | 178 ± 8* | 5.2 ± 1.7 | 11.4 ± 6.4 | 2.6 ± 2.2 | 7.1 ± 2.8 |

*p < 0.05 vs. Placebo
Untreated 1 and untreated 2 are the controls of study 1 and study number 2, respectively.

TABLE 2

Diastolic blood pressure after gavage.

| Groupe | Period | | | | Variation vs. Placebo | | | |
|---|---|---|---|---|---|---|---|---|
| | 0-24 | 3-6 | 12-15 | 21-24 | 0-24 | 3-6 | 12-15 | 21-24 |
| Untreated | 126± | 127± | 124± | 129± | | | | |
| Sample 1 | | | | | | | | |
| Dose 1 | 120± | 118± | 118± | 124± | — | — | — | −5.3 ± 2.4 |
| Dose 2 | 122± | 120± | 120± | 129± | — | — | — | −0.3 ± 2.3 |
| Dose 3 | 123± | 120± | 121± | 128± | — | — | — | −1.4 ± 1.6 |
| Untreated | 131 ± 5 | 125 ± 5 | 134 ± 5 | 125 ± 5 | | | | |
| Sample 2 | 123± | 119± | 125± | 119± | — | — | — | −5.7 ± 3.3 |
| Sample 3 | 126± | 127± | 125± | 121± | — | 2.7 ± 2.6 | — | −4.1 ± 2.3 |
| Sample 4 | 127± | 126± | 128± | 123± | — | 1.2 ± 3.5 | — | −2.5 ± 2.6 |
| Sample 5 | 133± | 135± | 133± | 130± | 3.2 ± 2.3 | 9.7 ± 5.5 | — | 4.8 ± 3.3 |

*p < 0.05 vs. Placebo
Untreated 1 and untreated 2 are the controls of study 1 and study number 2, respectively The results demonstrate that there is no need to up-concentrate the fermented milk product. Sample 3 is just the fermented milk product and it has a corresponding blood pressure reducing effects as for the freeze dried concentrated fermented samples 1 (Dose 1, 2, 3) and sample 2.

Sample 2 is freeze-dried fermented milk suspended in neutral pH milk. It reduces the blood pressure. This demonstrates the wide application of a fermented product as described herein since it may be dissolved in different liquids to get a required final appropriate use. Characteristic such as different pH are not affecting the blood reducing pressure activity of the product.

Sample 4 with heat treatment after fermentation reduce also the blood pressure. Substantially all bacteria are killed in this sample. Accordingly, this demonstrates that there is no need to have live bacteria in the final product.

Sample 5 has not been fermented but it includes the live bacteria. It does not reduce the blood pressure. It demonstrates that the fermentation step is required.

Example 7

Pulsed Field Gel Electrophoresis (PFGE) Fingerprinting

*Lactobacillus helveticus* strain CHCC5951 (deposited with accession number DSM 14998) was grown overnight at 37° C. in standard MRS media. Chromosomal DNA was isolated by use of a Qiagen kit. The isolated chromosomal DNA was completely digested with restriction enzyme SmaI (done according to manufacture instructions).

Electrophoresis conditions for the digested DNA were: CHEF Mapper XA System, Pulse times 2 to 30 sec linearly ramped over 24 hrs at 5.3 V/cm. 1.1% agarose, ½×TBE, 14° C.

The program used to run the gel was:

| Parameter | PFGE programme no. | | | | | |
|---|---|---|---|---|---|---|
| | 1 | 2 | 3 | 4 | 5 | 6 |
| Initial switch time in sec | 2 | 3 | 2 | 2 | 3 | 1 |
| final switch time in sec | 30 | 80 | 60 | 40 | 18 | 10 |
| ramp factor | linear | −1.53 | −1.24 | linear | linear | linear |
| run time in hrs | 24 | 24 | 24 | 24 | 24 | 21 |

The bands were compared on computer by using the Gel Compar II program.

Band sizes were determined by measuring band migration distances on three independent pulsed field electrophoreses and correlating the distances to the migration of a standard with known band sizes. The sizes are means of the three measured values ±5 kbp.

The resulting agarose gel is shown in FIG. 1. The sizes of the indicated 12 bands are:

band no. 1: 283 kbp
band no. 2: 259 kbp
band no. 3: 219 kbp
band no. 4: 138 kbp
band no. 5: 127 kbp
band no. 6: 119 kbp
band no. 7: 106 kbp
band no. 8: 88 kbp
band no. 9: 71 kbp
band no. 10: 59 kbp
band no. 11: 54 kbp
band no. 12: 46 kbp

REFERENCES

Below are mentioned references that are considered relevant in relation to the present invention.

Yamamoto et al , (1994), *J. Dairy Sci.*, 77: 917-922
Gobbetti M. et al (2000), *Appl Environ Microbiol*, 66 (9), 3898-3904
EP821968
EP1016709.
WO01/32836
Pederson et al (1999), J. of Bacteriology, 181: 4592-4597
Yamamoto et al (2000), *Biosci. Biotechnol. Biochem.*, 64(6): 1217-1222
EP058074

I claim:

1. A process for preparing peptides with anti-hypertensive properties, the process comprising fermenting a food material, comprising animal milk proteins or vegetable proteins, with a *Lactobacillus helveticus* strain to obtain a fermented food material which comprises said peptides with anti-hypertensive properties, characterized in that the *Lactobacillus helveticus* strain is the *Lactobacillus helveticus* strain with the registration number DSM 14998.

2. The process for preparing peptides of claim 1, wherein the food material comprises an animal milk protein.

3. The process for preparing peptides of claim 2, wherein the animal milk protein is casein.

4. The process for preparing peptides of claim 2, wherein the food material is milk or milk based material.

* * * * *

```
                         SEQUENCE LISTING

<160> NUMBER OF SEQ ID NOS: 20

<210> SEQ ID NO 1
<211> LENGTH: 5550
<212> TYPE: DNA
<213> ORGANISM: Lactobacillus helveticus
<220> FEATURE:
<221> NAME/KEY: CDS
<222> LOCATION: (1)..(5550)
<223> OTHER INFORMATION:
<300> PUBLICATION INFORMATION:
<308> DATABASE ACCESSION NUMBER: GeneBank/A133727
<309> DATABASE ENTRY DATE: 1999-08-23
<313> RELEVANT RESIDUES: (1)..(5550)

<400> SEQUENCE: 1 atg agg aga aac aaa tat gca ggc tta tta gtt tgt gcc act act cta        48
Met Arg Arg Asn Lys Tyr Ala Gly Leu Leu Val Cys Ala Thr Thr Leu
1               5                   10                  15 tcc gtc gta tct gtg ttc tct act gcc gaa caa caa gtt aag gct agt        96
Ser Val Val Ser Val Phe Ser Thr Ala Glu Gln Gln Val Lys Ala Ser
            20                  25                  30 gtt gac agc caa aca aaa act gtt gaa aaa agt act aaa gca gca gaa       144
Val Asp Ser Gln Thr Lys Thr Val Glu Lys Ser Thr Lys Ala Ala Glu
        35                  40                  45 tct act aca gca aat tta act aac aaa gca gtt gaa gcg caa tta gcc       192
Ser Thr Thr Ala Asn Leu Thr Asn Lys Ala Val Glu Ala Gln Leu Ala
    50                  55                  60
```

```
gca aaa ggt gtt aat ttt aaa cac tta act gtt aat caa aaa caa gat    240
Ala Lys Gly Val Asn Phe Lys His Leu Thr Val Asn Gln Lys Gln Asp
65              70                  75                  80 gta tat gtt gat gta att gtt cag tta tcg gct acc cca gct gct act    288
Val Tyr Val Asp Val Ile Val Gln Leu Ser Ala Thr Pro Ala Ala Thr
                    85                  90                  95 aat ggc tca gta agt gct aat tca agt agc gca gaa att gaa caa gct    336
Asn Gly Ser Val Ser Ala Asn Ser Ser Ser Ala Glu Ile Glu Gln Ala
                100                 105                 110 tct aaa aaa gta att gcc aat caa gct tct att aag gaa aaa gtt aag    384
Ser Lys Lys Val Ile Ala Asn Gln Ala Ser Ile Lys Glu Lys Val Lys
            115                 120                 125 gca att act aac caa gca att ggt aaa agt tat ggt tat gta gtt aac    432
Ala Ile Thr Asn Gln Ala Ile Gly Lys Ser Tyr Gly Tyr Val Val Asn
        130                 135                 140 gga ttt gca acc aaa gca aaa gta aag gat att caa aaa cta aga aat    480
Gly Phe Ala Thr Lys Ala Lys Val Lys Asp Ile Gln Lys Leu Arg Asn
145                 150                 155                 160 atc cct ggg gtt aaa tca gta act tta gct aaa gtt tat tac gca aat    528
Ile Pro Gly Val Lys Ser Val Thr Leu Ala Lys Val Tyr Tyr Ala Asn
                165                 170                 175 gat tct tca gct gac aat atg gct aac gtt tca acc gtt tgg aac aat    576
Asp Ser Ser Ala Asp Asn Met Ala Asn Val Ser Thr Val Trp Asn Asn
                180                 185                 190 tat aaa tac aaa ggg gaa ggt acc gtc gtt tct atc atc gat act ggt    624
Tyr Lys Tyr Lys Gly Glu Gly Thr Val Val Ser Ile Ile Asp Thr Gly
            195                 200                 205 att gat ccc aat cac aaa gat ttg cgc tta agc gat gat tcc aag gtc    672
Ile Asp Pro Asn His Lys Asp Leu Arg Leu Ser Asp Asp Ser Lys Val
        210                 215                 220 aaa tta acc aaa gat aag gtt aat gct ttt act aaa gaa tct ggt tat    720
Lys Leu Thr Lys Asp Lys Val Asn Ala Phe Thr Lys Glu Ser Gly Tyr
225                 230                 235                 240 ggt cgt tac ttt act gat aaa gtg cca tac ggt cac aat tat tca gac    768
Gly Arg Tyr Phe Thr Asp Lys Val Pro Tyr Gly His Asn Tyr Ser Asp
                245                 250                 255 aat aat gat aat att acc gat gat aat cct agc gag caa cat ggt atg    816
Asn Asn Asp Asn Ile Thr Asp Asp Asn Pro Ser Glu Gln His Gly Met
                260                 265                 270 cac gtt gct ggt atc gta gct gcc aat ggt act gcc gat tct gtt aac    864
His Val Ala Gly Ile Val Ala Ala Asn Gly Thr Ala Asp Ser Val Asn
            275                 280                 285 tct gtt gtt ggt gtt gcc cca gaa gct caa tta cta gct atg aag gct    912
Ser Val Val Gly Val Ala Pro Glu Ala Gln Leu Leu Ala Met Lys Ala
        290                 295                 300 ttc tct aat tca gat agt tca gcc tct act gat tct act agc att atc    960
Phe Ser Asn Ser Asp Ser Ser Ala Ser Thr Asp Ser Thr Ser Ile Ile
305                 310                 315                 320 ggt gca atc gat gat tct gcc aag ctt ggg gct gac gtt cta aac atg   1008
Gly Ala Ile Asp Asp Ser Ala Lys Leu Gly Ala Asp Val Leu Asn Met
                325                 330                 335 tca tta ggt tca gtt tct ggt gaa caa act gaa gac gat cca gaa gtt   1056
Ser Leu Gly Ser Val Ser Gly Glu Gln Thr Glu Asp Asp Pro Glu Val
                340                 345                 350 gcc gct gtt gaa cgt gcc act aag aaa ggt act gca gct gta att tct   1104
Ala Ala Val Glu Arg Ala Thr Lys Lys Gly Thr Ala Ala Val Ile Ser
            355                 360                 365 gcc ggt aac tcc ggc act tca aat tca gaa att gaa ggt gtt aat aaa   1152
Ala Gly Asn Ser Gly Thr Ser Asn Ser Glu Ile Glu Gly Val Asn Lys
        370                 375                 380
```

```
gct tat tac ggg aat cct gat atg gaa act tta ggt aat cca ggc act    1200
Ala Tyr Tyr Gly Asn Pro Asp Met Glu Thr Leu Gly Asn Pro Gly Thr
385                 390                 395                 400 gca aga agt gca aca act gtt gcc tct gct gaa aac act aag gct act    1248
Ala Arg Ser Ala Thr Thr Val Ala Ser Ala Glu Asn Thr Lys Ala Thr
        405                 410                 415 aca gat gga gta act att aca tct gct gat gga aaa act act atc gca    1296
Thr Asp Gly Val Thr Ile Thr Ser Ala Asp Gly Lys Thr Thr Ile Ala
420                 425                 430 ggt cca gaa gct act cag ctt tca gaa ggt act gac cgt gct ttc ttt    1344
Gly Pro Glu Ala Thr Gln Leu Ser Glu Gly Thr Asp Arg Ala Phe Phe
    435                 440                 445 aat gat aaa aaa ttc tac gtc gta aaa gat aag aat ggc aat tta ggc    1392
Asn Asp Lys Lys Phe Tyr Val Val Lys Asp Lys Asn Gly Asn Leu Gly
450                 455                 460 aca ggt tct gcc aag caa tat act tct gct gta aaa ggt aaa att gca    1440
Thr Gly Ser Ala Lys Gln Tyr Thr Ser Ala Val Lys Gly Lys Ile Ala
465                 470                 475                 480 att gtc aag cgt ggt gaa ctt act ttc act gat aaa caa aaa tat gcc    1488
Ile Val Lys Arg Gly Glu Leu Thr Phe Thr Asp Lys Gln Lys Tyr Ala
            485                 490                 495 caa gaa gct ggt gcc gct ggt tta atc att gtt aac aac aaa gcc ggc    1536
Gln Glu Ala Gly Ala Ala Gly Leu Ile Ile Val Asn Asn Lys Ala Gly
        500                 505                 510 gat ata act ggc atg tta ctt aac gct ggc ttc cct act gct ggt tta    1584
Asp Ile Thr Gly Met Leu Leu Asn Ala Gly Phe Pro Thr Ala Gly Leu
515                 520                 525 tca gct aca tca gga gaa aaa tta gta aaa tat gtt gaa gcc cat cct    1632
Ser Ala Thr Ser Gly Glu Lys Leu Val Lys Tyr Val Glu Ala His Pro
530                 535                 540 gat gaa gca ttg aag gta agt att gtt gtc caa gcc tta aat aat tct    1680
Asp Glu Ala Leu Lys Val Ser Ile Val Val Gln Ala Leu Asn Asn Ser
545                 550                 555                 560 gct cgt caa aca gac tta atg tct gat ttc acc tca tac ggt ccc act    1728
Ala Arg Gln Thr Asp Leu Met Ser Asp Phe Thr Ser Tyr Gly Pro Thr
            565                 570                 575 tct agc ttg gca ttt aag cca gat atc tca gca cca ggt gga cat att    1776
Ser Ser Leu Ala Phe Lys Pro Asp Ile Ser Ala Pro Gly Gly His Ile
        580                 585                 590 tgg tca act caa aat aac aat ggc tat act aac atg tct ggt act tca    1824
Trp Ser Thr Gln Asn Asn Asn Gly Tyr Thr Asn Met Ser Gly Thr Ser
595                 600                 605 atg gct tct cca ttt att gct ggt acc caa gca ctt gtt agt caa aca    1872
Met Ala Ser Pro Phe Ile Ala Gly Thr Gln Ala Leu Val Ser Gln Thr
610                 615                 620 atg aac gac aag aat ggt gct ttc tac gca act tat caa aag atg agc    1920
Met Asn Asp Lys Asn Gly Ala Phe Tyr Ala Thr Tyr Gln Lys Met Ser
625                 630                 635                 640 gca gaa gaa aga acg cca ttt att aag act cta gaa atg aat act gca    1968
Ala Glu Glu Arg Thr Pro Phe Ile Lys Thr Leu Glu Met Asn Thr Ala
            645                 650                 655 agt att caa cct gat att agc cat gat aat gtc atc gtt tca cca cgt    2016
Ser Ile Gln Pro Asp Ile Ser His Asp Asn Val Ile Val Ser Pro Arg
        660                 665                 670 aga caa ggt gct gga ttt att aac gct aac gct act atc caa gct tta    2064
Arg Gln Gly Ala Gly Phe Ile Asn Ala Asn Ala Thr Ile Gln Ala Leu
675                 680                 685 gct aaa aat cct tca act gta gtc agc agc aat ggc tat cct ggt gta    2112
Ala Lys Asn Pro Ser Thr Val Val Ser Ser Asn Gly Tyr Pro Gly Val
```

-continued

```
                    690                     695                     700
gaa ctc aaa agt ttt aaa gat aga act ctt aat ttc caa gtt aaa ttt       2160
Glu Leu Lys Ser Phe Lys Asp Arg Thr Leu Asn Phe Gln Val Lys Phe
705                     710                     715                 720 act aac cgt acc aac aag gcc tta act tat aaa tta gca aac aat ggt       2208
Thr Asn Arg Thr Asn Lys Ala Leu Thr Tyr Lys Leu Ala Asn Asn Gly
                    725                     730                 735 aaa aat tct gac gtt tac act tct gct act gat agt tct gca gtt tta       2256
Lys Asn Ser Asp Val Tyr Thr Ser Ala Thr Asp Ser Ser Ala Val Leu
                740                     745                 750 tat gat aag aag att gat ggc gca tca gtt aag gct agt ggt gac att       2304
Tyr Asp Lys Lys Ile Asp Gly Ala Ser Val Lys Ala Ser Gly Asp Ile
            755                     760                 765 ttt gtc ccg gca aat tct act aaa gaa cta act tta acc ttg acc tta       2352
Phe Val Pro Ala Asn Ser Thr Lys Glu Leu Thr Leu Thr Leu Thr Leu
        770                     775                 780 cct agt gac ttt aaa gaa aat caa tat gtt gaa ggc ttc tta aca ttt       2400
Pro Ser Asp Phe Lys Glu Asn Gln Tyr Val Glu Gly Phe Leu Thr Phe
785                     790                     795                 800 aat agt tca gat tct tca caa ttg cgt ctt cca tat atg ggc ttc ttt       2448
Asn Ser Ser Asp Ser Ser Gln Leu Arg Leu Pro Tyr Met Gly Phe Phe
                    805                     810                 815 ggc gat tgg gca agt tca gat ctt cca atc ttt gct agt ctt aat gat       2496
Gly Asp Trp Ala Ser Ser Asp Leu Pro Ile Phe Ala Ser Leu Asn Asp
                820                     825                 830 cca aat gta ttt cag cct gac aac aat atg ttt ggt aca ttg gta act       2544
Pro Asn Val Phe Gln Pro Asp Asn Asn Met Phe Gly Thr Leu Val Thr
            835                     840                 845 gta ggt aat agt tca gac aat act aat cct ggt tta agc caa gac gcc       2592
Val Gly Asn Ser Ser Asp Asn Thr Asn Pro Gly Leu Ser Gln Asp Ala
        850                     855                 860 tct ggt aac tta agt ttt gat tct tcg aaa ttt gca att tct aat gct       2640
Ser Gly Asn Leu Ser Phe Asp Ser Ser Lys Phe Ala Ile Ser Asn Ala
865                     870                     875                 880 aaa aat gca caa ttt aag tgg ttt aaa cct act tac tac tta tac aga       2688
Lys Asn Ala Gln Phe Lys Trp Phe Lys Pro Thr Tyr Tyr Leu Tyr Arg
                    885                     890                 895 aac gca aac aac gtt aaa atc caa att tta gat aag aat ggt aaa gta       2736
Asn Ala Asn Asn Val Lys Ile Gln Ile Leu Asp Lys Asn Gly Lys Val
                900                     905                 910 atc aat act tta gcc tct ttg agt aac gca acc aag act tac tat aac       2784
Ile Asn Thr Leu Ala Ser Leu Ser Asn Ala Thr Lys Thr Tyr Tyr Asn
            915                     920                 925 tct caa gct caa agc tat act tat ttt gac gat gct cct tct tgg gac       2832
Ser Gln Ala Gln Ser Tyr Thr Tyr Phe Asp Asp Ala Pro Ser Trp Asp
        930                     935                 940 ggc aca tac ttc gat caa caa gct aat aaa act gtt aat gct cct gat       2880
Gly Thr Tyr Phe Asp Gln Gln Ala Asn Lys Thr Val Asn Ala Pro Asp
945                     950                     955                 960 gga aac tat acc tac aga att tct gca act atc gat gga act aat act       2928
Gly Asn Tyr Thr Tyr Arg Ile Ser Ala Thr Ile Asp Gly Thr Asn Thr
                    965                     970                 975 gaa caa cat tac gat atc cct gtt aaa gtt gac agt gtt gca cct gta       2976
Glu Gln His Tyr Asp Ile Pro Val Lys Val Asp Ser Val Ala Pro Val
                980                     985                 990 gta aag aac ctt aaa tta gaa tca  agc aag gtt gaa gat  gct aaa ggt     3024
Val Lys Asn Leu Lys Leu Glu Ser  Ser Lys Val Glu Asp  Ala Lys Gly
            995                     1000                1005 caa gag  caa aca cgt tac tac  tta tct gca gaa gca  aaa gat gaa        3069
```

```
              Gln Glu Gln Thr Arg Tyr Tyr Leu Ser Ala Glu Ala Lys Asp Glu
                  1010            1015                1020 ctc agt ggt tta agt gga gac gca aat gtt tct gtc aat ggc gtt           3114
Leu Ser Gly Leu Ser Gly Asp Ala Asn Val Ser Val Asn Gly Val
    1025            1030                1035 tca gct caa tta gaa tac gat cct act gct aag gct gat aag gat           3159
Ser Ala Gln Leu Glu Tyr Asp Pro Thr Ala Lys Ala Asp Lys Asp
    1040            1045                1050 ggt ttc caa aaa gtg gaa atc gat tta tcc cca gct caa gca aag           3204
Gly Phe Gln Lys Val Glu Ile Asp Leu Ser Pro Ala Gln Ala Lys
    1055            1060                1065 gct ctt caa gca ggt aca aac acc ttt tct gtt gcc tta ttc gat           3249
Ala Leu Gln Ala Gly Thr Asn Thr Phe Ser Val Ala Leu Phe Asp
    1070            1075                1080 aat gct gca aat gca ggt aca gct tca ggt gaa ggc aat aaa cca           3294
Asn Ala Ala Asn Ala Gly Thr Ala Ser Gly Glu Gly Asn Lys Pro
    1085            1090                1095 ggt gaa act aac ttc ggt tta gtt ctt aga aac ggt ggc tta cca           3339
Gly Glu Thr Asn Phe Gly Leu Val Leu Arg Asn Gly Gly Leu Pro
    1100            1105                1110 gac aaa atc tca tct caa act aag ggc tac gat gcc aaa aat ggt           3384
Asp Lys Ile Ser Ser Gln Thr Lys Gly Tyr Asp Ala Lys Asn Gly
    1115            1120                1125 act tat gta ttc tct ggt act tac cca agc aaa ctc tat gga act           3429
Thr Tyr Val Phe Ser Gly Thr Tyr Pro Ser Lys Leu Tyr Gly Thr
    1130            1135                1140 tac act gat aaa gat ggt caa acc cat gac tta aat gta gaa agt           3474
Tyr Thr Asp Lys Asp Gly Gln Thr His Asp Leu Asn Val Glu Ser
    1145            1150                1155 gat ggc aac aag tta ttc gtt gca aag ctt cca ctt tct aaa gat           3519
Asp Gly Asn Lys Leu Phe Val Ala Lys Leu Pro Leu Ser Lys Asp
    1160            1165                1170 gac tat aag act act gtt acc ctt tac gct gat tct gac cat aag           3564
Asp Tyr Lys Thr Thr Val Thr Leu Tyr Ala Asp Ser Asp His Lys
    1175            1180                1185 acc ttg ctt aag aaa caa gac att acc gta agc tta gtc cca gct           3609
Thr Leu Leu Lys Lys Gln Asp Ile Thr Val Ser Leu Val Pro Ala
    1190            1195                1200 aag gtc gaa agt ttg tct gta gat aag aat gat act tat gat gag           3654
Lys Val Glu Ser Leu Ser Val Asp Lys Asn Asp Thr Tyr Asp Glu
    1205            1210                1215 act aaa gat tcg tcg gct gca tta gct caa act tct gaa aac act           3699
Thr Lys Asp Ser Ser Ala Ala Leu Ala Gln Thr Ser Glu Asn Thr
    1220            1225                1230 gta aaa ctt tct ggt aaa gta agt ggt gat act aag act tta gtg           3744
Val Lys Leu Ser Gly Lys Val Ser Gly Asp Thr Lys Thr Leu Val
    1235            1240                1245 gtt aaa caa aaa ggt cag aaa gac atc tca gtt aaa ctt aat gct           3789
Val Lys Gln Lys Gly Gln Lys Asp Ile Ser Val Lys Leu Asn Ala
    1250            1255                1260 gat cac aca ttt agt act gaa ctg cca gta agc ttt ggt gaa aat           3834
Asp His Thr Phe Ser Thr Glu Leu Pro Val Ser Phe Gly Glu Asn
    1265            1270                1275 gac ttt act att gta gca acc gac tct aat ggt aat tca tct agt           3879
Asp Phe Thr Ile Val Ala Thr Asp Ser Asn Gly Asn Ser Ser Ser
    1280            1285                1290 gta gaa caa aaa gtt aaa tct agt gat cgt ggt aaa act act gtt           3924
Val Glu Gln Lys Val Lys Ser Ser Asp Arg Gly Lys Thr Thr Val
    1295            1300                1305
```

-continued

| | | | | | | | | | | | | | | |
|---|---|---|---|---|---|---|---|---|---|---|---|---|---|---|
| tca | agt | agt | gat | gtt | acc | ttc | gat | aac | ggt | atc | aag | tgg | ggt | act | 3969 |
| Ser | Ser | Ser | Asp | Val | Thr | Phe | Asp | Asn | Gly | Ile | Lys | Trp | Gly | Thr | |
| 1310 | | | | 1315 | | | | | 1320 | | | | | | |
| cgt | aac | gtt | aac | ggt | att | cgt | aac | gtt | aac | gcc | aag | act | aag | aac | 4014 |
| Arg | Asn | Val | Asn | Gly | Ile | Arg | Asn | Val | Asn | Ala | Lys | Thr | Lys | Asn | |
| 1325 | | | | 1330 | | | | | 1335 | | | | | | |
| tac | aat | cct | aag | act | ggt | gag | tta | acc | ctt | act | ggt | aaa | gta | aaa | 4059 |
| Tyr | Asn | Pro | Lys | Thr | Gly | Glu | Leu | Thr | Leu | Thr | Gly | Lys | Val | Lys | |
| 1340 | | | | 1345 | | | | | 1350 | | | | | | |
| aga | cca | act | act | act | ttg | caa | att | ggc | ggt | aaa | aac | gta | aaa | att | 4104 |
| Arg | Pro | Thr | Thr | Thr | Leu | Gln | Ile | Gly | Gly | Lys | Asn | Val | Lys | Ile | |
| 1355 | | | | 1360 | | | | | 1365 | | | | | | |
| aat | tca | gat | cag | aca | ttt | aaa | gta | gta | tta | aat | att | ggt | act | cat | 4149 |
| Asn | Ser | Asp | Gln | Thr | Phe | Lys | Val | Val | Leu | Asn | Ile | Gly | Thr | His | |
| 1370 | | | | 1375 | | | | | 1380 | | | | | | |
| ggt | gct | aag | att | ttc | cct | gcg | ttg | atc | ggt | gat | tca | act | gtt | aga | 4194 |
| Gly | Ala | Lys | Ile | Phe | Pro | Ala | Leu | Ile | Gly | Asp | Ser | Thr | Val | Arg | |
| 1385 | | | | 1390 | | | | | 1395 | | | | | | |
| gaa | act | act | caa | gaa | aga | tta | agt | ttc | tat | gta | gat | gca | gaa | gct | 4239 |
| Glu | Thr | Thr | Gln | Glu | Arg | Leu | Ser | Phe | Tyr | Val | Asp | Ala | Glu | Ala | |
| 1400 | | | | 1405 | | | | | 1410 | | | | | | |
| cct | act | ttg | aac | tta | gat | agt | gaa | aac | act | gtc | tac | acc | aac | aag | 4284 |
| Pro | Thr | Leu | Asn | Leu | Asp | Ser | Glu | Asn | Thr | Val | Tyr | Thr | Asn | Lys | |
| 1415 | | | | 1420 | | | | | 1425 | | | | | | |
| gat | aag | ttt | act | atc | tca | ggc | act | ata | agt | gat | gat | tac | aag | ttc | 4329 |
| Asp | Lys | Phe | Thr | Ile | Ser | Gly | Thr | Ile | Ser | Asp | Asp | Tyr | Lys | Phe | |
| 1430 | | | | 1435 | | | | | 1440 | | | | | | |
| tac | gac | tta | tca | ata | aat | ggt | aac | gat | gtt | gaa | act | agc | tgg | agc | 4374 |
| Tyr | Asp | Leu | Ser | Ile | Asn | Gly | Asn | Asp | Val | Glu | Thr | Ser | Trp | Ser | |
| 1445 | | | | 1450 | | | | | 1455 | | | | | | |
| gcc | gta | gac | tac | cac | agc | aaa | gaa | ggt | atc | aag | aag | aac | ttt | aag | 4419 |
| Ala | Val | Asp | Tyr | His | Ser | Lys | Glu | Gly | Ile | Lys | Lys | Asn | Phe | Lys | |
| 1460 | | | | 1465 | | | | | 1470 | | | | | | |
| cat | gaa | gtt | gac | ttg | aag | aaa | ggt | aag | aat | act | ttt | aac | gtt | aaa | 4464 |
| His | Glu | Val | Asp | Leu | Lys | Lys | Gly | Lys | Asn | Thr | Phe | Asn | Val | Lys | |
| 1475 | | | | 1480 | | | | | 1485 | | | | | | |
| gta | act | gac | att | cag | ggt | aac | tca | agt | tca | caa | gca | tta | gtt | gta | 4509 |
| Val | Thr | Asp | Ile | Gln | Gly | Asn | Ser | Ser | Ser | Gln | Ala | Leu | Val | Val | |
| 1490 | | | | 1495 | | | | | 1500 | | | | | | |
| tac | tat | gaa | cct | gct | aag | act | tta | gct | gag | cct | agt | gta | gac | aag | 4554 |
| Tyr | Tyr | Glu | Pro | Ala | Lys | Thr | Leu | Ala | Glu | Pro | Ser | Val | Asp | Lys | |
| 1505 | | | | 1510 | | | | | 1515 | | | | | | |
| ttg | tta | aca | aag | acg | gca | aat | ttg | caa | ctt | ctt | aaa | gct | act | act | 4599 |
| Leu | Leu | Thr | Lys | Thr | Ala | Asn | Leu | Gln | Leu | Leu | Lys | Ala | Thr | Thr | |
| 1520 | | | | 1525 | | | | | 1530 | | | | | | |
| gat | gaa | tct | gaa | gct | aaa | gtt | gtt | tac | agc | ctt | gat | aat | ggc | aag | 4644 |
| Asp | Glu | Ser | Glu | Ala | Lys | Val | Val | Tyr | Ser | Leu | Asp | Asn | Gly | Lys | |
| 1535 | | | | 1540 | | | | | 1545 | | | | | | |
| aca | ttc | aac | gat | gta | cca | gct | gat | ggt | ttc | aag | gtt | act | gaa | aac | 4689 |
| Thr | Phe | Asn | Asp | Val | Pro | Ala | Asp | Gly | Phe | Lys | Val | Thr | Glu | Asn | |
| 1550 | | | | 1555 | | | | | 1560 | | | | | | |
| gga | act | gta | caa | ttt | aaa | gca | gtt | gat | aaa | tac | ggc | aac | gaa | tcc | 4734 |
| Gly | Thr | Val | Gln | Phe | Lys | Ala | Val | Asp | Lys | Tyr | Gly | Asn | Glu | Ser | |
| 1565 | | | | 1570 | | | | | 1575 | | | | | | |
| aaa | gtc | aag | tct | gta | gaa | att | aag | gga | ctt | aac | aag | gaa | aac | caa | 4779 |
| Lys | Val | Lys | Ser | Val | Glu | Ile | Lys | Gly | Leu | Asn | Lys | Glu | Asn | Gln | |
| 1580 | | | | 1585 | | | | | 1590 | | | | | | |
| cct | agc | gaa | gat | aag | gaa | tta | gct | aag | gct | aag | gaa | aat | ctt | cag | 4824 |
| Pro | Ser | Glu | Asp | Lys | Glu | Leu | Ala | Lys | Ala | Lys | Glu | Asn | Leu | Gln | |
| 1595 | | | | 1600 | | | | | 1605 | | | | | | |

```
gct aag gtt gat gcc ggt gaa aag aag gat ctt gat aag tac act       4869
Ala Lys Val Asp Ala Gly Glu Lys Lys Asp Leu Asp Lys Tyr Thr
    1610                1615                1620 gct gac tcc aag aag gac ttc aat gat gcc ttg aag aag gct aag       4914
Ala Asp Ser Lys Lys Asp Phe Asn Asp Ala Leu Lys Lys Ala Lys
1625                1630                1635 gat gtt tta gct gac aag aat gct aaa tta gct gac ctt caa gat       4959
Asp Val Leu Ala Asp Lys Asn Ala Lys Leu Ala Asp Leu Gln Asp
        1640                1645                1650 gct gct aag gct ctt gat aag gca gag caa gct tta act gaa aag       5004
Ala Ala Lys Ala Leu Asp Lys Ala Glu Gln Ala Leu Thr Glu Lys
    1655                1660                1665 cct gct gaa cca act atc cca ctg cta caa ggg aac aat aat gct       5049
Pro Ala Glu Pro Thr Ile Pro Leu Leu Gln Gly Asn Asn Asn Ala
1670                1675                1680 gta tcg aat att aat act tcc tct gat aac caa gtt gca gct cct       5094
Val Ser Asn Ile Asn Thr Ser Ser Asp Asn Gln Val Ala Ala Pro
        1685                1690                1695 gtg cat gct gaa aaa gac acc aag aat gat aac aag aat aca aca       5139
Val His Ala Glu Lys Asp Thr Lys Asn Asp Asn Lys Asn Thr Thr
    1700                1705                1710 gaa gaa ggt aag gac act aag gta atg ttc aag tca gtt ctt tac       5184
Glu Glu Gly Lys Asp Thr Lys Val Met Phe Lys Ser Val Leu Tyr
1715                1720                1725 act aaa gac ctt aaa aag aca agg agc act gcc caa gcc tac agt       5229
Thr Lys Asp Leu Lys Lys Thr Arg Ser Thr Ala Gln Ala Tyr Ser
        1730                1735                1740 tca ctc aaa ctt gta acc gaa aaa gga aag ctt aag gtt tac aca       5274
Ser Leu Lys Leu Val Thr Glu Lys Gly Lys Leu Lys Val Tyr Thr
    1745                1750                1755 ttc aaa ggt cac tac ttc tac aag gtt gtt gat cgg aat gca tat       5319
Phe Lys Gly His Tyr Phe Tyr Lys Val Val Asp Arg Asn Ala Tyr
1760                1765                1770 gtt cgt gta aga aat gtg act ggt act aag gca acg tta aag aga       5364
Val Arg Val Arg Asn Val Thr Gly Thr Lys Ala Thr Leu Lys Arg
        1775                1780                1785 aat tca ttt gtc tac caa tca aat ggt aag aaa gca tca cgt aaa       5409
Asn Ser Phe Val Tyr Gln Ser Asn Gly Lys Lys Ala Ser Arg Lys
    1790                1795                1800 ctt ctc aag aaa ggt act acc att acc gtc tac ggc gat caa tac       5454
Leu Leu Lys Lys Gly Thr Thr Ile Thr Val Tyr Gly Asp Gln Tyr
1805                1810                1815 aaa gct ctt aag cat tac aag aag tat gct tac aga atc ggt gaa       5499
Lys Ala Leu Lys His Tyr Lys Lys Tyr Ala Tyr Arg Ile Gly Glu
        1820                1825                1830 ggt aga tac ata aag agt gtc aat gtt aac aga gtt gat ctt gta       5544
Gly Arg Tyr Ile Lys Ser Val Asn Val Asn Arg Val Asp Leu Val
    1835                1840                1845 aaa taa                                                           5550
Lys

<210> SEQ ID NO 2
<211> LENGTH: 1849
<212> TYPE: PRT
<213> ORGANISM: Lactobacillus helveticus

<400> SEQUENCE: 2

Met Arg Arg Asn Lys Tyr Ala Gly Leu Leu Val Cys Ala Thr Thr Leu
1               5                   10                  15
```

-continued

```
Ser Val Val Ser Val Phe Ser Thr Ala Glu Gln Gln Val Lys Ala Ser
            20                  25                  30

Val Asp Ser Gln Thr Lys Thr Val Glu Lys Ser Thr Lys Ala Ala Glu
        35                  40                  45

Ser Thr Thr Ala Asn Leu Thr Asn Lys Ala Val Glu Ala Gln Leu Ala
    50                  55                  60

Ala Lys Gly Val Asn Phe Lys His Leu Thr Val Asn Gln Lys Gln Asp
65                  70                  75                  80

Val Tyr Val Asp Val Ile Val Gln Leu Ser Ala Thr Pro Ala Ala Thr
                85                  90                  95

Asn Gly Ser Val Ser Ala Asn Ser Ser Ala Glu Ile Glu Gln Ala
                    100                 105                 110

Ser Lys Lys Val Ile Ala Asn Gln Ala Ser Ile Lys Glu Lys Val Lys
            115                 120                 125

Ala Ile Thr Asn Gln Ala Ile Gly Lys Ser Tyr Gly Tyr Val Val Asn
130                 135                 140

Gly Phe Ala Thr Lys Ala Lys Val Lys Asp Ile Gln Lys Leu Arg Asn
145                 150                 155                 160

Ile Pro Gly Val Lys Ser Val Thr Leu Ala Lys Val Tyr Tyr Ala Asn
                165                 170                 175

Asp Ser Ser Ala Asp Asn Met Ala Asn Val Ser Thr Val Trp Asn Asn
            180                 185                 190

Tyr Lys Tyr Lys Gly Glu Gly Thr Val Val Ser Ile Ile Asp Thr Gly
        195                 200                 205

Ile Asp Pro Asn His Lys Asp Leu Arg Leu Ser Asp Ser Lys Val
    210                 215                 220

Lys Leu Thr Lys Asp Lys Val Asn Ala Phe Thr Lys Glu Ser Gly Tyr
225                 230                 235                 240

Gly Arg Tyr Phe Thr Asp Lys Val Pro Tyr Gly His Asn Tyr Ser Asp
                245                 250                 255

Asn Asn Asp Asn Ile Thr Asp Asp Asn Pro Ser Glu Gln His Gly Met
            260                 265                 270

His Val Ala Gly Ile Val Ala Ala Asn Gly Thr Ala Asp Ser Val Asn
        275                 280                 285

Ser Val Val Gly Val Ala Pro Glu Ala Gln Leu Leu Ala Met Lys Ala
    290                 295                 300

Phe Ser Asn Ser Asp Ser Ser Ala Ser Thr Asp Ser Thr Ser Ile Ile
305                 310                 315                 320

Gly Ala Ile Asp Asp Ser Ala Lys Leu Gly Ala Asp Val Leu Asn Met
                325                 330                 335

Ser Leu Gly Ser Val Ser Gly Glu Gln Thr Glu Asp Asp Pro Glu Val
            340                 345                 350

Ala Ala Val Glu Arg Ala Thr Lys Gly Thr Ala Ala Val Ile Ser
        355                 360                 365

Ala Gly Asn Ser Gly Thr Ser Asn Ser Glu Ile Glu Gly Val Asn Lys
370                 375                 380

Ala Tyr Tyr Gly Asn Pro Asp Met Glu Thr Leu Gly Asn Pro Gly Thr
385                 390                 395                 400

Ala Arg Ser Ala Thr Thr Val Ala Ser Ala Glu Asn Thr Lys Ala Thr
                405                 410                 415

Thr Asp Gly Val Thr Ile Thr Ser Ala Asp Gly Lys Thr Thr Ile Ala
            420                 425                 430

Gly Pro Glu Ala Thr Gln Leu Ser Glu Gly Thr Asp Arg Ala Phe Phe
```

-continued

```
            435                 440                 445
Asn Asp Lys Lys Phe Tyr Val Val Lys Asp Lys Asn Gly Asn Leu Gly
    450                 455                 460
Thr Gly Ser Ala Lys Gln Tyr Thr Ser Ala Val Lys Gly Lys Ile Ala
465                 470                 475                 480
Ile Val Lys Arg Gly Glu Leu Thr Phe Thr Asp Lys Gln Lys Tyr Ala
                485                 490                 495
Gln Glu Ala Gly Ala Ala Gly Leu Ile Ile Val Asn Asn Lys Ala Gly
                500                 505                 510
Asp Ile Thr Gly Met Leu Leu Asn Ala Gly Phe Pro Thr Ala Gly Leu
            515                 520                 525
Ser Ala Thr Ser Gly Glu Lys Leu Val Lys Tyr Val Glu Ala His Pro
        530                 535                 540
Asp Glu Ala Leu Lys Val Ser Ile Val Val Gln Ala Leu Asn Asn Ser
545                 550                 555                 560
Ala Arg Gln Thr Asp Leu Met Ser Asp Phe Thr Ser Tyr Gly Pro Thr
                565                 570                 575
Ser Ser Leu Ala Phe Lys Pro Asp Ile Ser Ala Pro Gly Gly His Ile
            580                 585                 590
Trp Ser Thr Gln Asn Asn Gly Tyr Thr Asn Met Ser Gly Thr Ser
        595                 600                 605
Met Ala Ser Pro Phe Ile Ala Gly Thr Gln Ala Leu Val Ser Gln Thr
    610                 615                 620
Met Asn Asp Lys Asn Gly Ala Phe Tyr Ala Thr Tyr Gln Lys Met Ser
625                 630                 635                 640
Ala Glu Glu Arg Thr Pro Phe Ile Lys Thr Leu Glu Met Asn Thr Ala
                645                 650                 655
Ser Ile Gln Pro Asp Ile Ser His Asp Asn Val Ile Val Ser Pro Arg
                660                 665                 670
Arg Gln Gly Ala Gly Phe Ile Asn Ala Asn Ala Thr Ile Gln Ala Leu
            675                 680                 685
Ala Lys Asn Pro Ser Thr Val Val Ser Ser Asn Gly Tyr Pro Gly Val
        690                 695                 700
Glu Leu Lys Ser Phe Lys Asp Arg Thr Leu Asn Phe Gln Val Lys Phe
705                 710                 715                 720
Thr Asn Arg Thr Asn Lys Ala Leu Thr Tyr Lys Leu Ala Asn Asn Gly
                725                 730                 735
Lys Asn Ser Asp Val Tyr Thr Ser Ala Thr Asp Ser Ser Ala Val Leu
            740                 745                 750
Tyr Asp Lys Lys Ile Asp Gly Ala Ser Val Lys Ala Ser Gly Asp Ile
        755                 760                 765
Phe Val Pro Ala Asn Ser Thr Lys Glu Leu Thr Leu Thr Leu Thr Leu
    770                 775                 780
Pro Ser Asp Phe Lys Glu Asn Gln Tyr Val Glu Gly Phe Leu Thr Phe
785                 790                 795                 800
Asn Ser Ser Asp Ser Ser Gln Leu Arg Leu Pro Tyr Met Gly Phe Phe
                805                 810                 815
Gly Asp Trp Ala Ser Ser Asp Leu Pro Ile Phe Ala Ser Leu Asn Asp
            820                 825                 830
Pro Asn Val Phe Gln Pro Asp Asn Asn Met Phe Gly Thr Leu Val Thr
        835                 840                 845
Val Gly Asn Ser Ser Asp Asn Thr Asn Pro Gly Leu Ser Gln Asp Ala
    850                 855                 860
```

```
Ser Gly Asn Leu Ser Phe Asp Ser Ser Lys Phe Ala Ile Ser Asn Ala
865                 870                 875                 880

Lys Asn Ala Gln Phe Lys Trp Phe Lys Pro Thr Tyr Tyr Leu Tyr Arg
            885                 890                 895

Asn Ala Asn Asn Val Lys Ile Gln Ile Leu Asp Lys Asn Gly Lys Val
            900                 905                 910

Ile Asn Thr Leu Ala Ser Leu Ser Asn Ala Thr Lys Thr Tyr Tyr Asn
        915                 920                 925

Ser Gln Ala Gln Ser Tyr Thr Tyr Phe Asp Asp Ala Pro Ser Trp Asp
    930                 935                 940

Gly Thr Tyr Phe Asp Gln Gln Ala Asn Lys Thr Val Asn Ala Pro Asp
945                 950                 955                 960

Gly Asn Tyr Thr Tyr Arg Ile Ser Ala Thr Ile Asp Gly Thr Asn Thr
                965                 970                 975

Glu Gln His Tyr Asp Ile Pro Val Lys Val Asp Ser Val Ala Pro Val
            980                 985                 990

Val Lys Asn Leu Lys Leu Glu Ser  Ser Lys Val Glu Asp  Ala Lys Gly
        995                 1000                1005

Gln Glu  Gln Thr Arg Tyr Tyr  Leu Ser Ala Glu Ala  Lys Asp Glu
    1010                1015                1020

Leu Ser  Gly Leu Ser Gly Asp  Ala Asn Val Ser Val  Asn Gly Val
    1025                1030                1035

Ser Ala  Gln Leu Glu Tyr Asp  Pro Thr Ala Lys Ala  Asp Lys Asp
    1040                1045                1050

Gly Phe  Gln Lys Val Glu Ile  Asp Leu Ser Pro Ala  Gln Ala Lys
    1055                1060                1065

Ala Leu  Gln Ala Gly Thr Asn  Thr Phe Ser Val Ala  Leu Phe Asp
    1070                1075                1080

Asn Ala  Ala Asn Ala Gly Thr  Ala Ser Gly Glu Gly  Asn Lys Pro
    1085                1090                1095

Gly Glu  Thr Asn Phe Gly Leu  Val Leu Arg Asn Gly  Gly Leu Pro
    1100                1105                1110

Asp Lys  Ile Ser Ser Gln Thr  Lys Gly Tyr Asp Ala  Lys Asn Gly
    1115                1120                1125

Thr Tyr  Val Phe Ser Gly Thr  Tyr Pro Ser Lys Leu  Tyr Gly Thr
    1130                1135                1140

Tyr Thr  Asp Lys Asp Gly Gln  Thr His Asp Leu Asn  Val Glu Ser
    1145                1150                1155

Asp Gly  Asn Lys Leu Phe Val  Ala Lys Leu Pro Leu  Ser Lys Asp
    1160                1165                1170

Asp Tyr  Lys Thr Thr Val Thr  Leu Tyr Ala Asp Ser  Asp His Lys
    1175                1180                1185

Thr Leu  Leu Lys Lys Gln Asp  Ile Thr Val Ser Leu  Val Pro Ala
    1190                1195                1200

Lys Val  Glu Ser Leu Ser Val  Asp Lys Asn Asp Thr  Tyr Asp Glu
    1205                1210                1215

Thr Lys  Asp Ser Ser Ala Ala  Leu Ala Gln Thr Ser  Glu Asn Thr
    1220                1225                1230

Val Lys  Leu Ser Gly Lys Val  Ser Gly Asp Thr Lys  Thr Leu Val
    1235                1240                1245

Val Lys  Gln Lys Gly Gln Lys  Asp Ile Ser Val Lys  Leu Asn Ala
    1250                1255                1260
```

-continued

```
Asp His Thr Phe Ser Thr Glu Leu Pro Val Ser Phe Gly Glu Asn
1265                 1270                1275

Asp Phe Thr Ile Val Ala Thr Asp Ser Asn Gly Asn Ser Ser Ser
1280                 1285                1290

Val Glu Gln Lys Val Lys Ser Ser Asp Arg Gly Lys Thr Thr Val
1295                 1300                1305

Ser Ser Ser Asp Val Thr Phe Asp Asn Gly Ile Lys Trp Gly Thr
1310                 1315                1320

Arg Asn Val Asn Gly Ile Arg Asn Val Asn Ala Lys Thr Lys Asn
1325                 1330                1335

Tyr Asn Pro Lys Thr Gly Glu Leu Thr Leu Thr Gly Lys Val Lys
1340                 1345                1350

Arg Pro Thr Thr Thr Leu Gln Ile Gly Gly Lys Asn Val Lys Ile
1355                 1360                1365

Asn Ser Asp Gln Thr Phe Lys Val Val Leu Asn Ile Gly Thr His
1370                 1375                1380

Gly Ala Lys Ile Phe Pro Ala Leu Ile Gly Asp Ser Thr Val Arg
1385                 1390                1395

Glu Thr Thr Gln Glu Arg Leu Ser Phe Tyr Val Asp Ala Glu Ala
1400                 1405                1410

Pro Thr Leu Asn Leu Asp Ser Glu Asn Thr Val Tyr Thr Asn Lys
1415                 1420                1425

Asp Lys Phe Thr Ile Ser Gly Thr Ile Ser Asp Asp Tyr Lys Phe
1430                 1435                1440

Tyr Asp Leu Ser Ile Asn Gly Asn Asp Val Glu Thr Ser Trp Ser
1445                 1450                1455

Ala Val Asp Tyr His Ser Lys Glu Gly Ile Lys Lys Asn Phe Lys
1460                 1465                1470

His Glu Val Asp Leu Lys Lys Gly Lys Asn Thr Phe Asn Val Lys
1475                 1480                1485

Val Thr Asp Ile Gln Gly Asn Ser Ser Ser Gln Ala Leu Val Val
1490                 1495                1500

Tyr Tyr Glu Pro Ala Lys Thr Leu Ala Glu Pro Ser Val Asp Lys
1505                 1510                1515

Leu Leu Thr Lys Thr Ala Asn Leu Gln Leu Leu Lys Ala Thr Thr
1520                 1525                1530

Asp Glu Ser Glu Ala Lys Val Val Tyr Ser Leu Asp Asn Gly Lys
1535                 1540                1545

Thr Phe Asn Asp Val Pro Ala Asp Gly Phe Lys Val Thr Glu Asn
1550                 1555                1560

Gly Thr Val Gln Phe Lys Ala Val Asp Lys Tyr Gly Asn Glu Ser
1565                 1570                1575

Lys Val Lys Ser Val Glu Ile Lys Gly Leu Asn Lys Glu Asn Gln
1580                 1585                1590

Pro Ser Glu Asp Lys Glu Leu Ala Lys Ala Lys Glu Asn Leu Gln
1595                 1600                1605

Ala Lys Val Asp Ala Gly Glu Lys Lys Asp Leu Asp Lys Tyr Thr
1610                 1615                1620

Ala Asp Ser Lys Lys Asp Phe Asn Asp Ala Leu Lys Lys Ala Lys
1625                 1630                1635

Asp Val Leu Ala Asp Lys Asn Ala Lys Leu Ala Asp Leu Gln Asp
1640                 1645                1650

Ala Ala Lys Ala Leu Asp Lys Ala Glu Gln Ala Leu Thr Glu Lys
```

-continued

```
                    1655                 1660                 1665

Pro Ala Glu Pro Thr Ile Pro  Leu Leu Gln Gly Asn  Asn Asn Ala
    1670                 1675                 1680

Val Ser Asn Ile Asn Thr Ser  Ser Asp Asn Gln Val  Ala Ala Pro
    1685                 1690                 1695

Val His Ala Glu Lys Asp Thr  Lys Asn Asp Asn Lys  Asn Thr Thr
    1700                 1705                 1710

Glu Glu Gly Lys Asp Thr Lys  Val Met Phe Lys Ser  Val Leu Tyr
    1715                 1720                 1725

Thr Lys Asp Leu Lys Lys Thr  Arg Ser Thr Ala Gln  Ala Tyr Ser
    1730                 1735                 1740

Ser Leu Lys Leu Val Thr Glu  Lys Gly Lys Leu Lys  Val Tyr Thr
    1745                 1750                 1755

Phe Lys Gly His Tyr Phe Tyr  Lys Val Val Asp Arg  Asn Ala Tyr
    1760                 1765                 1770

Val Arg Val Arg Asn Val Thr  Gly Thr Lys Ala Thr  Leu Lys Arg
    1775                 1780                 1785

Asn Ser Phe Val Tyr Gln Ser  Asn Gly Lys Lys Ala  Ser Arg Lys
    1790                 1795                 1800

Leu Leu Lys Lys Gly Thr Thr  Ile Thr Val Tyr Gly  Asp Gln Tyr
    1805                 1810                 1815

Lys Ala Leu Lys His Tyr Lys  Lys Tyr Ala Tyr Arg  Ile Gly Glu
    1820                 1825                 1830

Gly Arg Tyr Ile Lys Ser Val  Asn Val Asn Arg Val  Asp Leu Val
    1835                 1840                 1845

Lys

<210> SEQ ID NO 3
<211> LENGTH: 2679
<212> TYPE: DNA
<213> ORGANISM: Lactobacillus helveticus
<220> FEATURE:
<221> NAME/KEY: CDS
<222> LOCATION: (1)..(2679)
<223> OTHER INFORMATION:

<400> SEQUENCE: 3 atg ata aga cta ctg gga aga tgg ttg tgc tcc aga tgg tca ata cac      48
Met Ile Arg Leu Leu Gly Arg Trp Leu Cys Ser Arg Trp Ser Ile His
1               5                   10                  15 tta ccg ctt tgt tgc ccc ttg tac aac aat ggt gaa aac aaa gtt caa      96
Leu Pro Leu Cys Cys Pro Leu Tyr Asn Asn Gly Glu Asn Lys Val Gln
            20                  25                  30 act aat gac act cca gtt atc att gat act act gct cct gtt ttg aac     144
Thr Asn Asp Thr Pro Val Ile Ile Asp Thr Thr Ala Pro Val Leu Asn
        35                  40                  45 aat gtg aaa tat gat aca tct tct ttc aca ttg tca ggt gat tac gct     192
Asn Val Lys Tyr Asp Thr Ser Ser Phe Thr Leu Ser Gly Asp Tyr Ala
    50                  55                  60 gat gca ggt gca ggc ttt act gac tac tca tat gca act gta act gtt     240
Asp Ala Gly Ala Gly Phe Thr Asp Tyr Ser Tyr Ala Thr Val Thr Val
65                  70                  75                  80 aac gat cat gtc ttt ggc ttt aag tta aac gaa ggc gat aag tca aac     288
Asn Asp His Val Phe Gly Phe Lys Leu Asn Glu Gly Asp Lys Ser Asn
                85                  90                  95 ttt gat aat gct aat aaa acc aag gga cac ttt gtc ttt gtt ttg act     336
Phe Asp Asn Ala Asn Lys Thr Lys Gly His Phe Val Phe Val Leu Thr
            100                 105                 110
```

```
ccg gaa gaa caa gct gct tta act agc gct gct aac aag gtt acc gtt       384
Pro Glu Glu Gln Ala Ala Leu Thr Ser Ala Ala Asn Lys Val Thr Val
        115                 120                 125 gcc ttt agt gat gtc gca gat aac act gca acg caa aca ttt aat gtt       432
Ala Phe Ser Asp Val Ala Asp Asn Thr Ala Thr Gln Thr Phe Asn Val
130                 135                 140 gca cct gta gca ggt cat aaa aag att gca gtt tgg aat gca att aat       480
Ala Pro Val Ala Gly His Lys Lys Ile Ala Val Trp Asn Ala Ile Asn
145                 150                 155                 160 ggg tta cca ttc aat gaa aat tcc gat gat tat aat gtt ggt cgc aaa       528
Gly Leu Pro Phe Asn Glu Asn Ser Asp Asp Tyr Asn Val Gly Arg Lys
                165                 170                 175 gta ttt atg ctt cgt ggt ggt gct gaa cat gat ttc tat gtc aat ggt       576
Val Phe Met Leu Arg Gly Gly Ala Glu His Asp Phe Tyr Val Asn Gly
            180                 185                 190 aag tgg gtt cag gtt gat caa ggt caa ttt gta ttg cca gtt agt gtt       624
Lys Trp Val Gln Val Asp Gln Gly Gln Phe Val Leu Pro Val Ser Val
        195                 200                 205 gat gaa cag aat ttt gtt ttc agt tca gat caa gcg ggt aaa aat att       672
Asp Glu Gln Asn Phe Val Phe Ser Ser Asp Gln Ala Gly Lys Asn Ile
210                 215                 220 tta ggt aag ttc act act ttt act cct aaa gct caa ttc gca tgg caa       720
Leu Gly Lys Phe Thr Thr Phe Thr Pro Lys Ala Gln Phe Ala Trp Gln
225                 230                 235                 240 cat gtt gat ggt gaa gaa aga tca ttt ggt gtc agt gtt tac tca gta       768
His Val Asp Gly Glu Glu Arg Ser Phe Gly Val Ser Val Tyr Ser Val
                245                 250                 255 gaa ggc aag gat cca caa gat att gtt gtt caa gca tca gta ccc aag       816
Glu Gly Lys Asp Pro Gln Asp Ile Val Val Gln Ala Ser Val Pro Lys
            260                 265                 270 ggt gac aat gtt aaa gct ttt gcg aag gac tac ttc act cat gaa gtt       864
Gly Asp Asn Val Lys Ala Phe Ala Lys Asp Tyr Phe Thr His Glu Val
        275                 280                 285 tat acc ggt gag gtt cat gac ggt gta gct act ttc cac att cat acc       912
Tyr Thr Gly Glu Val His Asp Gly Val Ala Thr Phe His Ile His Thr
290                 295                 300 agt gtc aat aaa gac gct gca act ggc att aat tta aga gcc ctt ctt       960
Ser Val Asn Lys Asp Ala Ala Thr Gly Ile Asn Leu Arg Ala Leu Leu
305                 310                 315                 320 caa ggt tgg gtt gaa att gat gga cca aca ttt aat gct aaa caa gta      1008
Gln Gly Trp Val Glu Ile Asp Gly Pro Thr Phe Asn Ala Lys Gln Val
                325                 330                 335 acg gat cca tcg cca att aat gat gct aac tac ttg ggt gtg tac tac      1056
Thr Asp Pro Ser Pro Ile Asn Asp Ala Asn Tyr Leu Gly Val Tyr Tyr
            340                 345                 350 aat cca aat gct gaa gag aga aag aat tat gat aat cgc gat gat ctt      1104
Asn Pro Asn Ala Glu Glu Arg Lys Asn Tyr Asp Asn Arg Asp Asp Leu
        355                 360                 365 ggc gta gac ttt gaa gat gaa gca gct gac aca aac aca ttt ggc cca      1152
Gly Val Asp Phe Glu Asp Glu Ala Ala Asp Thr Asn Thr Phe Gly Pro
370                 375                 380 ggg aat tat tca agt gcg aaa gat gac gct aaa att cat ttc gac tac      1200
Gly Asn Tyr Ser Ser Ala Lys Asp Asp Ala Lys Ile His Phe Asp Tyr
385                 390                 395                 400 ttg aat aat aat ggt att tct act ttg ggt aat aaa gca gta gaa aag      1248
Leu Asn Asn Asn Gly Ile Ser Thr Leu Gly Asn Lys Ala Val Glu Lys
                405                 410                 415 ggt tat tac aat cca gca act cat aaa ttt act ttg act ggt cgg gtt      1296
Gly Tyr Tyr Asn Pro Ala Thr His Lys Phe Thr Leu Thr Gly Arg Val
```

```
                420             425             430
aat cca gaa gtt att agc tta aca ttc tta gct gat agt ccg tat gaa      1344
Asn Pro Glu Val Ile Ser Leu Thr Phe Leu Ala Asp Ser Pro Tyr Glu
        435                 440                 445 gtc gat cca gaa aat caa gct gat att cat gat aat ggt aaa ttc tct      1392
Val Asp Pro Glu Asn Gln Ala Asp Ile His Asp Asn Gly Lys Phe Ser
    450                 455                 460 gta aca ttc aca att gat aat cca gca aca cgt caa tta tca tat ttc      1440
Val Thr Phe Thr Ile Asp Asn Pro Ala Thr Arg Gln Leu Ser Tyr Phe
465                 470                 475                 480 ttt aag acg aat gat ggc aaa aca aca aga ggc tct ttg act tta att      1488
Phe Lys Thr Asn Asp Gly Lys Thr Thr Arg Gly Ser Leu Thr Leu Ile
                485                 490                 495 ctt gac act gtt gat cca act ctt act gta gat caa tta ggc gac aag      1536
Leu Asp Thr Val Asp Pro Thr Leu Thr Val Asp Gln Leu Gly Asp Lys
            500                 505                 510 gat gag gct gaa att act act aat aag cca acc ttt aag tta tcc ggt      1584
Asp Glu Ala Glu Ile Thr Thr Asn Lys Pro Thr Phe Lys Leu Ser Gly
        515                 520                 525 gag gcc aac gat aac att gat ggt tac aat gta ttt atc aat ggt gat      1632
Glu Ala Asn Asp Asn Ile Asp Gly Tyr Asn Val Phe Ile Asn Gly Asp
    530                 535                 540 aat gtt ttt ggg caa ttt ggt aat tcg ggt tat gat ttt ctg cca gga      1680
Asn Val Phe Gly Gln Phe Gly Asn Ser Gly Tyr Asp Phe Leu Pro Gly
545                 550                 555                 560 atc tac aat gat tta aat caa aat act cca aat ttg tac gga tct tac      1728
Ile Tyr Asn Asp Leu Asn Gln Asn Thr Pro Asn Leu Tyr Gly Ser Tyr
                565                 570                 575 aag ttt gat caa gaa gag caa ttg gat gat cag aat ggg caa cca aca      1776
Lys Phe Asp Gln Glu Glu Gln Leu Asp Asp Gln Asn Gly Gln Pro Thr
            580                 585                 590 acc cat gtc ttt act att gca gta gag gac caa gct ggt aac aga gtt      1824
Thr His Val Phe Thr Ile Ala Val Glu Asp Gln Ala Gly Asn Arg Val
        595                 600                 605 gaa aag aag gtt act gtt cat tac gat cca aat tat ctt aca gaa ccg      1872
Glu Lys Lys Val Thr Val His Tyr Asp Pro Asn Tyr Leu Thr Glu Pro
    610                 615                 620 ggt aat aca gga aaa aaa gat gat caa gca gat gta aaa ccg gca gaa      1920
Gly Asn Thr Gly Lys Lys Asp Asp Gln Ala Asp Val Lys Pro Ala Glu
625                 630                 635                 640 ggt caa aag caa gat aaa aat gac aac caa act gtt aac aat tca aaa      1968
Gly Gln Lys Gln Asp Lys Asn Asp Asn Gln Thr Val Asn Asn Ser Lys
                645                 650                 655 gaa gat cca gag agt ggt caa act act gaa aat gct caa tct aca gaa      2016
Glu Asp Pro Glu Ser Gly Gln Thr Thr Glu Asn Ala Gln Ser Thr Glu
            660                 665                 670 agt caa gag caa aat aag act gat gta act aaa cca gca gca aag cca      2064
Ser Gln Glu Gln Asn Lys Thr Asp Val Thr Lys Pro Ala Ala Lys Pro
        675                 680                 685 agt aac gat gat caa aaa gaa aat cac aga gct ggt gaa tcg acc att      2112
Ser Asn Asp Asp Gln Lys Glu Asn His Arg Ala Gly Glu Ser Thr Ile
    690                 695                 700 gag tta aat caa gag aaa caa cta ggt caa agt aat gtc caa gcc caa      2160
Glu Leu Asn Gln Glu Lys Gln Leu Gly Gln Ser Asn Val Gln Ala Gln
705                 710                 715                 720 gat act aaa cca gat aaa aca gta gtt caa ggt aat gtt caa aat act      2208
Asp Thr Lys Pro Asp Lys Thr Val Val Gln Gly Asn Val Gln Asn Thr
                725                 730                 735 gca ccg aca aca ggt cat ttg act aat tct tca gta aat gtg caa caa      2256
```

-continued

```
Ala Pro Thr Thr Gly His Leu Thr Asn Ser Ser Val Asn Val Gln Gln
            740                 745                 750 ttt aag act aag aaa gaa aca cta caa tta aag aag ttt aag tta tta       2304
Phe Lys Thr Lys Lys Glu Thr Leu Gln Leu Lys Lys Phe Lys Leu Leu
            755                 760                 765 aag aat aca tat ggc tac act tta aat ggt aaa att gct aaa aaa cac       2352
Lys Asn Thr Tyr Gly Tyr Thr Leu Asn Gly Lys Ile Ala Lys Lys His
            770                 775                 780 ggt aaa aag tta ctc ttt aag aaa gga aaa acc gtc ctt gtt tgg aac       2400
Gly Lys Lys Leu Leu Phe Lys Lys Gly Lys Thr Val Leu Val Trp Asn
785                 790                 795                 800 aac agt aga gtt gtg act atc aag gga caa aag tac tac cgt gct act       2448
Asn Ser Arg Val Val Thr Ile Lys Gly Gln Lys Tyr Tyr Arg Ala Thr
                805                 810                 815 aag aat gta ttt gtt aaa gtt tca act atc aag cag gtt aaa gac ttg       2496
Lys Asn Val Phe Val Lys Val Ser Thr Ile Lys Gln Val Lys Asp Leu
            820                 825                 830 aaa tta gtt tta acg aag aac tcc tac gtt tac aat aaa ttg ggc aaa       2544
Lys Leu Val Leu Thr Lys Asn Ser Tyr Val Tyr Asn Lys Leu Gly Lys
            835                 840                 845 cgc gtt aag tat aag agt caa agt ttg ctt aag gaa ggt aaa cat ctt       2592
Arg Val Lys Tyr Lys Ser Gln Ser Leu Leu Lys Glu Gly Lys His Leu
        850                 855                 860 tct acc cac aat aat gga aaa gtt gtg act att aaa aat ata cat ttt       2640
Ser Thr His Asn Asn Gly Lys Val Val Thr Ile Lys Asn Ile His Phe
865                 870                 875                 880 ttt aat ata tct ctt ttc tta aaa tat ttc caa caa cgt                   2679
Phe Asn Ile Ser Leu Phe Leu Lys Tyr Phe Gln Gln Arg
            885                 890

<210> SEQ ID NO 4
<211> LENGTH: 893
<212> TYPE: PRT
<213> ORGANISM: Lactobacillus helveticus

<400> SEQUENCE: 4

Met Ile Arg Leu Leu Gly Arg Trp Leu Cys Ser Arg Trp Ser Ile His
1               5                   10                  15

Leu Pro Leu Cys Cys Pro Leu Tyr Asn Asn Gly Glu Asn Lys Val Gln
            20                  25                  30

Thr Asn Asp Thr Pro Val Ile Asp Thr Thr Ala Pro Val Leu Asn
        35                  40                  45

Asn Val Lys Tyr Asp Thr Ser Ser Phe Thr Leu Ser Gly Asp Tyr Ala
    50                  55                  60

Asp Ala Gly Ala Gly Phe Thr Asp Tyr Ser Tyr Ala Thr Val Thr Val
65                  70                  75                  80

Asn Asp His Val Phe Gly Phe Lys Leu Asn Glu Gly Asp Lys Ser Asn
                85                  90                  95

Phe Asp Asn Ala Asn Lys Thr Lys Gly His Phe Val Phe Val Leu Thr
            100                 105                 110

Pro Glu Glu Gln Ala Ala Leu Thr Ser Ala Ala Asn Lys Val Thr Val
            115                 120                 125

Ala Phe Ser Asp Val Ala Asp Asn Thr Ala Thr Gln Thr Phe Asn Val
        130                 135                 140

Ala Pro Val Ala Gly His Lys Lys Ile Ala Val Trp Asn Ala Ile Asn
145                 150                 155                 160

Gly Leu Pro Phe Asn Glu Asn Ser Asp Asp Tyr Asn Val Gly Arg Lys
                165                 170                 175
```

```
Val Phe Met Leu Arg Gly Gly Ala Glu His Asp Phe Tyr Val Asn Gly
            180                 185                 190

Lys Trp Val Gln Val Asp Gln Gly Gln Phe Val Leu Pro Val Ser Val
            195                 200                 205

Asp Glu Gln Asn Phe Val Phe Ser Ser Asp Gln Ala Gly Lys Asn Ile
            210                 215                 220

Leu Gly Lys Phe Thr Thr Phe Thr Pro Lys Ala Gln Phe Ala Trp Gln
225                 230                 235                 240

His Val Asp Gly Glu Glu Arg Ser Phe Gly Val Ser Val Tyr Ser Val
                    245                 250                 255

Glu Gly Lys Asp Pro Gln Asp Ile Val Val Gln Ala Ser Val Pro Lys
                    260                 265                 270

Gly Asp Asn Val Lys Ala Phe Ala Lys Asp Tyr Phe Thr His Glu Val
                275                 280                 285

Tyr Thr Gly Glu Val His Asp Gly Val Ala Thr Phe His Ile His Thr
            290                 295                 300

Ser Val Asn Lys Asp Ala Ala Thr Gly Ile Asn Leu Arg Ala Leu Leu
305                 310                 315                 320

Gln Gly Trp Val Glu Ile Asp Gly Pro Thr Phe Asn Ala Lys Gln Val
                    325                 330                 335

Thr Asp Pro Ser Pro Ile Asn Asp Ala Asn Tyr Leu Gly Val Tyr Tyr
                340                 345                 350

Asn Pro Asn Ala Glu Glu Arg Lys Asn Tyr Asp Asn Arg Asp Asp Leu
            355                 360                 365

Gly Val Asp Phe Glu Asp Glu Ala Ala Asp Thr Asn Thr Phe Gly Pro
            370                 375                 380

Gly Asn Tyr Ser Ser Ala Lys Asp Asp Ala Lys Ile His Phe Asp Tyr
385                 390                 395                 400

Leu Asn Asn Asn Gly Ile Ser Thr Leu Gly Asn Lys Ala Val Glu Lys
                    405                 410                 415

Gly Tyr Tyr Asn Pro Ala Thr His Lys Phe Thr Leu Thr Gly Arg Val
                420                 425                 430

Asn Pro Glu Val Ile Ser Leu Thr Phe Leu Ala Asp Ser Pro Tyr Glu
            435                 440                 445

Val Asp Pro Glu Asn Gln Ala Asp Ile His Asp Asn Gly Lys Phe Ser
450                 455                 460

Val Thr Phe Thr Ile Asp Asn Pro Ala Thr Arg Gln Leu Ser Tyr Phe
465                 470                 475                 480

Phe Lys Thr Asn Asp Gly Lys Thr Thr Arg Gly Ser Leu Thr Leu Ile
                    485                 490                 495

Leu Asp Thr Val Asp Pro Thr Leu Thr Val Asp Gln Leu Gly Asp Lys
                500                 505                 510

Asp Glu Ala Glu Ile Thr Thr Asn Lys Pro Thr Phe Lys Leu Ser Gly
            515                 520                 525

Glu Ala Asn Asp Asn Ile Asp Gly Tyr Asn Val Phe Ile Asn Gly Asp
530                 535                 540

Asn Val Phe Gly Gln Phe Gly Asn Ser Gly Tyr Asp Phe Leu Pro Gly
545                 550                 555                 560

Ile Tyr Asn Asp Leu Asn Gln Asn Thr Pro Asn Leu Tyr Gly Ser Tyr
                    565                 570                 575

Lys Phe Asp Gln Glu Glu Gln Leu Asp Asp Gln Asn Gly Gln Pro Thr
                580                 585                 590
```

```
Thr His Val Phe Thr Ile Ala Val Glu Asp Gln Ala Gly Asn Arg Val
        595                 600                 605

Glu Lys Lys Val Thr Val His Tyr Asp Pro Asn Tyr Leu Thr Glu Pro
    610                 615                 620

Gly Asn Thr Gly Lys Lys Asp Asp Gln Ala Asp Val Lys Pro Ala Glu
625                 630                 635                 640

Gly Gln Lys Gln Asp Lys Asn Asp Asn Gln Thr Val Asn Asn Ser Lys
                645                 650                 655

Glu Asp Pro Glu Ser Gly Gln Thr Thr Glu Asn Ala Gln Ser Thr Glu
            660                 665                 670

Ser Gln Glu Gln Asn Lys Thr Asp Val Thr Lys Pro Ala Ala Lys Pro
        675                 680                 685

Ser Asn Asp Asp Gln Lys Glu Asn His Arg Ala Gly Glu Ser Thr Ile
    690                 695                 700

Glu Leu Asn Gln Glu Lys Gln Leu Gly Gln Ser Asn Val Gln Ala Gln
705                 710                 715                 720

Asp Thr Lys Pro Asp Lys Thr Val Val Gln Gly Asn Val Gln Asn Thr
                725                 730                 735

Ala Pro Thr Thr Gly His Leu Thr Asn Ser Ser Val Asn Val Gln Gln
            740                 745                 750

Phe Lys Thr Lys Lys Glu Thr Leu Gln Leu Lys Lys Phe Lys Leu Leu
        755                 760                 765

Lys Asn Thr Tyr Gly Tyr Thr Leu Asn Gly Lys Ile Ala Lys His
    770                 775                 780

Gly Lys Lys Leu Leu Phe Lys Lys Gly Lys Thr Val Leu Val Trp Asn
785                 790                 795                 800

Asn Ser Arg Val Val Thr Ile Lys Gly Gln Lys Tyr Tyr Arg Ala Thr
                805                 810                 815

Lys Asn Val Phe Val Lys Val Ser Thr Ile Lys Gln Val Lys Asp Leu
            820                 825                 830

Lys Leu Val Leu Thr Lys Asn Ser Tyr Val Tyr Asn Lys Leu Gly Lys
        835                 840                 845

Arg Val Lys Tyr Lys Ser Gln Ser Leu Leu Lys Glu Gly Lys His Leu
    850                 855                 860

Ser Thr His Asn Asn Gly Lys Val Val Thr Ile Lys Asn Ile His Phe
865                 870                 875                 880

Phe Asn Ile Ser Leu Phe Leu Lys Tyr Phe Gln Gln Arg
                885                 890

<210> SEQ ID NO 5
<211> LENGTH: 4881
<212> TYPE: DNA
<213> ORGANISM: Lactobacillus helveticus
<220> FEATURE:
<221> NAME/KEY: CDS
<222> LOCATION: (1)..(4881)
<223> OTHER INFORMATION:

<400> SEQUENCE: 5 atg cta ctg gta ttc cag aaa ttg cag tta tgg gtg gct gca gca att     48
Met Leu Leu Val Phe Gln Lys Leu Gln Leu Trp Val Ala Ala Ala Ile
1               5                  10                  15 att gct ctt gct tca ggc tcc act gtt ttt ctt agt caa aat act gct     96
Ile Ala Leu Ala Ser Gly Ser Thr Val Phe Leu Ser Gln Asn Thr Ala
            20                  25                  30 gaa gca gca act aat gat cct ggt gct tca gat gtt caa gtt aaa gta    144
Glu Ala Ala Thr Asn Asp Pro Gly Ala Ser Asp Val Gln Val Lys Val
```

```
                35                   40                   45
gta caa caa gat caa aaa caa gac caa aac agt act gct aac gca gct      192
Val Gln Gln Asp Gln Lys Gln Asp Gln Asn Ser Thr Ala Asn Ala Ala
     50                  55                  60 gtt tca aat tct gat tct gcc aag aca cag act aat gca acg gac cag      240
Val Ser Asn Ser Asp Ser Ala Lys Thr Gln Thr Asn Ala Thr Asp Gln
 65                  70                  75                  80 aca caa aat tca act gtg gtt tct ggt gat tcc acg act gcg aat tct      288
Thr Gln Asn Ser Thr Val Val Ser Gly Asp Ser Thr Thr Ala Asn Ser
                     85                  90                  95 aag acc tca cag act tct aat gca caa act aca agt aca aca aca aat      336
Lys Thr Ser Gln Thr Ser Asn Ala Gln Thr Thr Ser Thr Thr Thr Asn
                100                 105                 110 agt gta gat cca aac cag gaa caa caa cct gct aat caa gct gat cat      384
Ser Val Asp Pro Asn Gln Glu Gln Gln Pro Ala Asn Gln Ala Asp His
            115                 120                 125 gtt aaa gga aat gtg cag tct gca tgg gat caa gga tat agg gga caa      432
Val Lys Gly Asn Val Gln Ser Ala Trp Asp Gln Gly Tyr Arg Gly Gln
        130                 135                 140 gga aca gtt gtt gca gtc atc gat tcc ggt gca gat cca act cat aaa      480
Gly Thr Val Val Ala Val Ile Asp Ser Gly Ala Asp Pro Thr His Lys
145                 150                 155                 160 gat ttt aaa acc atg cca gaa gat cct aag ctg tcc gag gat gat atg      528
Asp Phe Lys Thr Met Pro Glu Asp Pro Lys Leu Ser Glu Asp Asp Met
                165                 170                 175 caa gct aag atc gcc aag caa ggc tat ggt aaa tat gtg aat gaa aag      576
Gln Ala Lys Ile Ala Lys Gln Gly Tyr Gly Lys Tyr Val Asn Glu Lys
            180                 185                 190 ttc cca tat gtt tat aat tat gcc gat cgt gat aat gac tat att act      624
Phe Pro Tyr Val Tyr Asn Tyr Ala Asp Arg Asp Asn Asp Tyr Ile Thr
        195                 200                 205 tcg gat gac acc aat gct aat gat tct cca cac ggt caa cac gtt tca      672
Ser Asp Asp Thr Asn Ala Asn Asp Ser Pro His Gly Gln His Val Ser
    210                 215                 220 gga atc att gca gct gat ggt aag cca gat gga aat aaa gaa tat gtc      720
Gly Ile Ile Ala Ala Asp Gly Lys Pro Asp Gly Asn Lys Glu Tyr Val
225                 230                 235                 240 gtt ggt gtt gct cct gaa gct caa ttg atg cag ctg aga gtt ttt gga      768
Val Gly Val Ala Pro Glu Ala Gln Leu Met Gln Leu Arg Val Phe Gly
                245                 250                 255 caa ttt tca gat gaa aaa act gat gat gtg gca aaa gca atc tac gat      816
Gln Phe Ser Asp Glu Lys Thr Asp Asp Val Ala Lys Ala Ile Tyr Asp
            260                 265                 270 gct acc aat tta ggt gcg gat gtc atc caa atg tca tta gga caa ggt      864
Ala Thr Asn Leu Gly Ala Asp Val Ile Gln Met Ser Leu Gly Gln Gly
        275                 280                 285 gtt gcc gat caa caa ttg acc aat att gag caa aaa gct gtt caa tat      912
Val Ala Asp Gln Gln Leu Thr Asn Ile Glu Gln Lys Ala Val Gln Tyr
    290                 295                 300 gca att gat cac ggt gta ttt gta tca att tca gca tct aat aac ggt      960
Ala Ile Asp His Gly Val Phe Val Ser Ile Ser Ala Ser Asn Asn Gly
305                 310                 315                 320 aat tca gct tca gtt gat aat cca agt aaa gtt aaa gat caa gga tat      1008
Asn Ser Ala Ser Val Asp Asn Pro Ser Lys Val Lys Asp Gln Gly Tyr
                325                 330                 335 caa tct ggt agc caa gct ggt aac tat gaa cct ctt aat tta agt act      1056
Gln Ser Gly Ser Gln Ala Gly Asn Tyr Glu Pro Leu Asn Leu Ser Thr
            340                 345                 350 gta gca aac cct ggt gtg tca aag aac gca tta act gtt gct gca gaa      1104
Val Ala Asn Pro Gly Val Ser Lys Asn Ala Leu Thr Val Ala Ala Glu
```

```
                Val Ala Asn Pro Gly Val Ser Lys Asn Ala Leu Thr Val Ala Ala Glu
                            355                 360                 365 aca tca gat act ggt gat tta agc gat atg gcc tac ttc tca tca tgg      1152
Thr Ser Asp Thr Gly Asp Leu Ser Asp Met Ala Tyr Phe Ser Ser Trp
            370                 375                 380 ggc cca gct caa gac tat act tta aag cca gat tta tca gca cct gga      1200
Gly Pro Ala Gln Asp Tyr Thr Leu Lys Pro Asp Leu Ser Ala Pro Gly
385                 390                 395                 400 tat caa gta gtt tct acc gtt aat cat gat cag tac caa aca atg agt      1248
Tyr Gln Val Val Ser Thr Val Asn His Asp Gln Tyr Gln Thr Met Ser
                405                 410                 415 ggt act tca atg gct ggt cca ttt gcc gca gct agt gct gcc tta gta      1296
Gly Thr Ser Met Ala Gly Pro Phe Ala Ala Ala Ser Ala Ala Leu Val
            420                 425                 430 att caa cga ttg aag caa act aat cct gaa ttg aag ggt gca caa tta      1344
Ile Gln Arg Leu Lys Gln Thr Asn Pro Glu Leu Lys Gly Ala Gln Leu
        435                 440                 445 gta gct gct gct aaa gca atg ctg atg aat acg gcc aaa cca caa aca      1392
Val Ala Ala Ala Lys Ala Met Leu Met Asn Thr Ala Lys Pro Gln Thr
    450                 455                 460 caa tta ggc tat aca aca cct gtt tca cca aga cgt caa ggt gca ggt      1440
Gln Leu Gly Tyr Thr Thr Pro Val Ser Pro Arg Arg Gln Gly Ala Gly
465                 470                 475                 480 caa att gat gtt ggt gct gct acg gct act cca gtt tat gta act act      1488
Gln Ile Asp Val Gly Ala Ala Thr Ala Thr Pro Val Tyr Val Thr Thr
                485                 490                 495 gat gac ggc act agt tca gta tca ctt cat caa gtt ggt gaa agt act      1536
Asp Asp Gly Thr Ser Ser Val Ser Leu His Gln Val Gly Glu Ser Thr
            500                 505                 510 aaa ttt acg tta acc ttc cat aat tta act gac caa agc cga act tat      1584
Lys Phe Thr Leu Thr Phe His Asn Leu Thr Asp Gln Ser Arg Thr Tyr
        515                 520                 525 act ttc gat gat tat ggt gga ggt tac act gaa caa aga gat aca acc      1632
Thr Phe Asp Asp Tyr Gly Gly Gly Tyr Thr Glu Gln Arg Asp Thr Thr
    530                 535                 540 acc ggc gtt ttt cat gat gtt caa tta gct ggt gct aga gta aat ggt      1680
Thr Gly Val Phe His Asp Val Gln Leu Ala Gly Ala Arg Val Asn Gly
545                 550                 555                 560 gaa cat agt ttt act tta gct cct aaa gaa gaa cgt caa gtt agc tat      1728
Glu His Ser Phe Thr Leu Ala Pro Lys Glu Glu Arg Gln Val Ser Tyr
                565                 570                 575 tca tta gac ttg acc ggc tta aag aag aac caa tta gtt gaa gga ttt      1776
Ser Leu Asp Leu Thr Gly Leu Lys Lys Asn Gln Leu Val Glu Gly Phe
            580                 585                 590 tta cgc ttt act aat gcc aat aat gca tct acg gtt tct gtt cct tac      1824
Leu Arg Phe Thr Asn Ala Asn Asn Ala Ser Thr Val Ser Val Pro Tyr
        595                 600                 605 tta gct tat tat ggg gac tta act agt gaa aac gtc ttt gat caa aat      1872
Leu Ala Tyr Tyr Gly Asp Leu Thr Ser Glu Asn Val Phe Asp Gln Asn
    610                 615                 620 gca aat gag gag cat cta gat atc cag ggt aat cgt tta gtt aat gaa      1920
Ala Asn Glu Glu His Leu Asp Ile Gln Gly Asn Arg Leu Val Asn Glu
625                 630                 635                 640 caa aac tat cct cgt ggt att gca gat caa gaa tca ttg aag gaa ctt      1968
Gln Asn Tyr Pro Arg Gly Ile Ala Asp Gln Glu Ser Leu Lys Glu Leu
                645                 650                 655 gta aat gtt gat gga aac tat aat tgg caa gaa gta gcc aaa tta tat      2016
Val Asn Val Asp Gly Asn Tyr Asn Trp Gln Glu Val Ala Lys Leu Tyr
            660                 665                 670
```

```
gaa agt ggt aaa gtt gcc ttt tca cca aat gat aat caa aag agc gat    2064
Glu Ser Gly Lys Val Ala Phe Ser Pro Asn Asp Asn Gln Lys Ser Asp
            675                 680                 685 tta ctg aag cca tat gtt tac ttg aag caa aat gtt aaa gat ctt aag    2112
Leu Leu Lys Pro Tyr Val Tyr Leu Lys Gln Asn Val Lys Asp Leu Lys
    690                 695                 700 gta gaa atc ctc gat gca caa ggt aac gtg gtt aga gtg gtt tct gac    2160
Val Glu Ile Leu Asp Ala Gln Gly Asn Val Val Arg Val Val Ser Asp
705                 710                 715                 720 gtt caa ggc gta gat aaa tct tac gat gaa aat ggt gta act aaa gat    2208
Val Gln Gly Val Asp Lys Ser Tyr Asp Glu Asn Gly Val Thr Lys Asp
                725                 730                 735 act agt tta tca gtt tca atg aga gat aat cct gac gct ctt gaa tgg    2256
Thr Ser Leu Ser Val Ser Met Arg Asp Asn Pro Asp Ala Leu Glu Trp
            740                 745                 750 gat ggt aaa gtt tat aac agc aaa aca ggc aaa atg gaa act gcc aaa    2304
Asp Gly Lys Val Tyr Asn Ser Lys Thr Gly Lys Met Glu Thr Ala Lys
    755                 760                 765 gat ggc aat tac act tac cgt tta gtt gct act ctt tgg aac aaa gga    2352
Asp Gly Asn Tyr Thr Tyr Arg Leu Val Ala Thr Leu Trp Asn Lys Gly
770                 775                 780 cca cat caa gtt caa aca gct gat ttc cca gta gta gtt gat aca gtt    2400
Pro His Gln Val Gln Thr Ala Asp Phe Pro Val Val Val Asp Thr Val
785                 790                 795                 800 gct cca aca ttg tca aat gtg aaa tat gat gct gcc tca cat act ttg    2448
Ala Pro Thr Leu Ser Asn Val Lys Tyr Asp Ala Ala Ser His Thr Leu
            805                 810                 815 tca ggt gaa tac caa gat gct ggt gca gga ttt acg aat tat tca tat    2496
Ser Gly Glu Tyr Gln Asp Ala Gly Ala Gly Phe Thr Asn Tyr Ser Tyr
    820                 825                 830 gca acg gta aca gtt aat gat aag gtc ttt ggc tat aag ttg agt gat    2544
Ala Thr Val Thr Val Asn Asp Lys Val Phe Gly Tyr Lys Leu Ser Asp
835                 840                 845 ggt gga tca ggc ttc gat aat gca gaa aag act aag gga cat ttt agc    2592
Gly Gly Ser Gly Phe Asp Asn Ala Glu Lys Thr Lys Gly His Phe Ser
                855                 860 ttt gtg tta ggt caa gat gca ctt tct gca tta aca gct gct gca aac    2640
Phe Val Leu Gly Gln Asp Ala Leu Ser Ala Leu Thr Ala Ala Ala Asn
865                 870                 875                 880 aag gtg acc gta gcc ttg agt gat gtc gct gat aat act tca ttg gct    2688
Lys Val Thr Val Ala Leu Ser Asp Val Ala Asp Asn Thr Ser Leu Ala
            885                 890                 895 act gtt aat gtt gcc ggt gac cat gat agt gag act ggt gta agt gtt    2736
Thr Val Asn Val Ala Gly Asp His Asp Ser Glu Thr Gly Val Ser Val
    900                 905                 910 tgg aat gct gtc aat ggt tta gcc ttt gat caa aaa tca cca aac tat    2784
Trp Asn Ala Val Asn Gly Leu Ala Phe Asp Gln Lys Ser Pro Asn Tyr
915                 920                 925 gat gca gct act aag act tac aca tta gtt ggt gga gct aac cat gac    2832
Asp Ala Ala Thr Lys Thr Tyr Thr Leu Val Gly Gly Ala Asn His Asp
                930                 935                 940 ttc tac tta aat ggc aag ttg gtc caa gta caa gat ggc aaa tat caa    2880
Phe Tyr Leu Asn Gly Lys Leu Val Gln Val Gln Asp Gly Lys Tyr Gln
945                 950                 955                 960 gtt cca gtc agt gta aat aca act aag ttt gtg ttt agt act gat cct    2928
Val Pro Val Ser Val Asn Thr Thr Lys Phe Val Phe Ser Thr Asp Pro
            965                 970                 975 gaa ggt caa cat gtt ctt aag gat ctt tca act gta acg gct aaa gca    2976
Glu Gly Gln His Val Leu Lys Asp Leu Ser Thr Val Thr Ala Lys Ala
    980                 985                 990
```

```
ttc ttt aat tgg caa aag act gat  aca ttt gat gga aac  ttt ggt gta     3024
Phe Phe Asn Trp Gln Lys Thr Asp  Thr Phe Asp Gly Asn  Phe Gly Val
        995                 1000                 1005 act att agt tca gtt aaa act  aat aat cca aat gat  aca gtt gtt         3069
Thr Ile Ser Ser Val Lys Thr  Asn Asn Pro Asn Asp  Thr Val Val
    1010                 1015                 1020 caa gct gtt gta acc aaa ggt  aaa aat gta aag gcc  tat gca atg         3114
Gln Ala Val Val Thr Lys Gly  Lys Asn Val Lys Ala  Tyr Ala Met
    1025                 1030                 1035 gat tac ttt act ggg gaa gtt  tat acc ggt gaa gta  aaa gac gga         3159
Asp Tyr Phe Thr Gly Glu Val  Tyr Thr Gly Glu Val  Lys Asp Gly
    1040                 1045                 1050 att gca aca ttc cat gtt cat  act tca atc aat aaa  gat gct aca         3204
Ile Ala Thr Phe His Val His  Thr Ser Ile Asn Lys  Asp Ala Thr
    1055                 1060                 1065 act ggt gtt tat agg aga gca  tta cta aca ggt tgg  act gaa gtg         3249
Thr Gly Val Tyr Arg Arg Ala  Leu Leu Thr Gly Trp  Thr Glu Val
    1070                 1075                 1080 gat gga cca tcc ttt aat gat  aaa caa gaa aca tct  aga gat ggt         3294
Asp Gly Pro Ser Phe Asn Asp  Lys Gln Glu Thr Ser  Arg Asp Gly
    1085                 1090                 1095 gta tca agt agt aac cac cta  ggg gtt ttc tac ttt  gct gat gca         3339
Val Ser Ser Ser Asn His Leu  Gly Val Phe Tyr Phe  Ala Asp Ala
    1100                 1105                 1110 gct aat cgc cca gtt tat aca  gat aga aat gcc ttg  gga gta gaa         3384
Ala Asn Arg Pro Val Tyr Thr  Asp Arg Asn Ala Leu  Gly Val Glu
    1115                 1120                 1125 gct aaa gat gaa gct gca aag  tta gat tca ttt tgc  cca ggt gca         3429
Ala Lys Asp Glu Ala Ala Lys  Leu Asp Ser Phe Cys  Pro Gly Ala
    1130                 1135                 1140 tac cca gga cac gca cca tca  gct ctg aca acc aga  acg gat cct         3474
Tyr Pro Gly His Ala Pro Ser  Ala Leu Thr Thr Arg  Thr Asp Pro
    1145                 1150                 1155 aat cca gat att cat ttt gat  tat atg aat gac aac  gat act act         3519
Asn Pro Asp Ile His Phe Asp  Tyr Met Asn Asp Asn  Asp Thr Thr
    1160                 1165                 1170 cgt ttt ggt cag aat gcc gtt  act cat gga tac tat  gat cct tca         3564
Arg Phe Gly Gln Asn Ala Val  Thr His Gly Tyr Tyr  Asp Pro Ser
    1175                 1180                 1185 act cag aag ttt acg gtt acc  ggt aaa gtt gat gac  aat gta gta         3609
Thr Gln Lys Phe Thr Val Thr  Gly Lys Val Asp Asp  Asn Val Val
    1190                 1195                 1200 tct cta act gtg tta ggc gat  aac tca aat gaa aat  gct cct gaa         3654
Ser Leu Thr Val Leu Gly Asp  Asn Ser Asn Glu Asn  Ala Pro Glu
    1205                 1210                 1215 aac caa gtt aag tta ggc aac  gac ggt aag ttt agc  ttt acg gta         3699
Asn Gln Val Lys Leu Gly Asn  Asp Gly Lys Phe Ser  Phe Thr Val
    1220                 1225                 1230 aca gct aac aga aca ggg caa  cgt cca att gca tat  att tac aaa         3744
Thr Ala Asn Arg Thr Gly Gln  Arg Pro Ile Ala Tyr  Ile Tyr Lys
    1235                 1240                 1245 gct aaa gat gga caa aga gtt  cgt ggt acc ttg aat  ctt att ctt         3789
Ala Lys Asp Gly Gln Arg Val  Arg Gly Thr Leu Asn  Leu Ile Leu
    1250                 1255                 1260 gat act gtt gct cct agc ttg  gaa gta aat cag gtt  aat ggg gat         3834
Asp Thr Val Ala Pro Ser Leu  Glu Val Asn Gln Val  Asn Gly Asp
    1265                 1270                 1275 gaa tta gag ctt tgg act aat  aat cca aaa ttc act  ctg tcc gga         3879
Glu Leu Glu Leu Trp Thr Asn  Asn Pro Lys Phe Thr  Leu Ser Gly
```

|      |      |      |      |      |      |      |      |      |      |      |      |      |      |      |      |
| ---- | ---- | ---- | ---- | ---- | ---- | ---- | ---- | ---- | ---- | ---- | ---- | ---- | ---- | ---- | ---- |
|      |      | 1280 |      |      |      |      | 1285 |      |      |      |      | 1290 |      |      |      |

```
aag gta aat gat aat ctt gat gga tat agg tta ttc gtt aat ggt      3924
Lys Val Asn Asp Asn Leu Asp Gly Tyr Arg Leu Phe Val Asn Gly
    1295                1300                1305 aat aat att tat cga gaa ttc cta aac tct ggt tat aat cag gtt      3969
Asn Asn Ile Tyr Arg Glu Phe Leu Asn Ser Gly Tyr Asn Gln Val
    1310                1315                1320 gca gga ttg aat acg gat act gag ttt act aat cca tat gga gct      4014
Ala Gly Leu Asn Thr Asp Thr Glu Phe Thr Asn Pro Tyr Gly Ala
    1325                1330                1335 cat gat ttt gaa gag gtt gaa aac tta aat gac aat aat gat caa      4059
His Asp Phe Glu Glu Val Glu Asn Leu Asn Asp Asn Asn Asp Gln
    1340                1345                1350 ccg act act cat gtc ttc aca gtt tat gtt gta gac caa gtt gga      4104
Pro Thr Thr His Val Phe Thr Val Tyr Val Val Asp Gln Val Gly
    1355                1360                1365 aac aag gta gaa aag aaa tta act gtt cac ttt gat cca aat tat      4149
Asn Lys Val Glu Lys Lys Leu Thr Val His Phe Asp Pro Asn Tyr
    1370                1375                1380 gtt gct cca gaa gaa gta cca aat act gat act tca tat act tta      4194
Val Ala Pro Glu Glu Val Pro Asn Thr Asp Thr Ser Tyr Thr Leu
    1385                1390                1395 gag aat cca tta agt act aca act gta gaa aac cca gtt act gat      4239
Glu Asn Pro Leu Ser Thr Thr Thr Val Glu Asn Pro Val Thr Asp
    1400                1405                1410 gtt tct acg gtt caa cct aag ggt gaa act tta act ggt aag tca      4284
Val Ser Thr Val Gln Pro Lys Gly Glu Thr Leu Thr Gly Lys Ser
    1415                1420                1425 ttc aac tta tta cac gat gct tat atc tac aac aaa gat ggt caa      4329
Phe Asn Leu Leu His Asp Ala Tyr Ile Tyr Asn Lys Asp Gly Gln
    1430                1435                1440 gtc gtt tta agt act gat act aat aag agt agc ttg ctt aag aaa      4374
Val Val Leu Ser Thr Asp Thr Asn Lys Ser Ser Leu Leu Lys Lys
    1445                1450                1455 ggc caa aga att act gca tta gac aat ggc aaa act gtt gta atc      4419
Gly Gln Arg Ile Thr Ala Leu Asp Asn Gly Lys Thr Val Val Ile
    1460                1465                1470 aat ggc gtg caa tac tat cgt gtc ggc gat aat cag ttt gtg aag      4464
Asn Gly Val Gln Tyr Tyr Arg Val Gly Asp Asn Gln Phe Val Lys
    1475                1480                1485 gta act aat acg att tta caa gcc ggt aag aga ttg cag tta aag      4509
Val Thr Asn Thr Ile Leu Gln Ala Gly Lys Arg Leu Gln Leu Lys
    1490                1495                1500 cat aat gca cac ctt tat gat aag aac ggt aaa gtt gtt aaa aga      4554
His Asn Ala His Leu Tyr Asp Lys Asn Gly Lys Val Val Lys Arg
    1505                1510                1515 aat ggc aaa cct gtc ttg tta aga aag ggt aga tgg atc agt gct      4599
Asn Gly Lys Pro Val Leu Leu Arg Lys Gly Arg Trp Ile Ser Ala
    1520                1525                1530 ttg aac aac gcc gat aag tat gta atc aat ggc aag acc ttc tac      4644
Leu Asn Asn Ala Asp Lys Tyr Val Ile Asn Gly Lys Thr Phe Tyr
    1535                1540                1545 aag tta gct aat ggt gaa ttt gtg aag gtg gca aac act aaa ctt      4689
Lys Leu Ala Asn Gly Glu Phe Val Lys Val Ala Asn Thr Lys Leu
    1550                1555                1560 caa aag cct aaa gct ttg aag ctt aca cac aat gca ttt gtt tac      4734
Gln Lys Pro Lys Ala Leu Lys Leu Thr His Asn Ala Phe Val Tyr
    1565                1570                1575 gat gaa aat ggt aag cgt gta aag aag agt aaa gtt tta aag aaa      4779
```

```
                                          -continued

Asp Glu Asn Gly Lys Arg Val Lys Lys Ser Lys Val Leu Lys Lys
         1580              1585               1590 ggc caa acg att tta gca gaa aat aat gca gaa aaa ttc cat atc    4824
Gly Gln Thr Ile Leu Ala Glu Asn Asn Ala Glu Lys Phe His Ile
    1595              1600              1605 aaa ggt aag gct tac tat aaa gtt aat ggt cat ttt gta aaa gtt    4869
Lys Gly Lys Ala Tyr Tyr Lys Val Asn Gly His Phe Val Lys Val
1610              1615              1620 gca aat act ttg                                                 4881
Ala Asn Thr Leu
    1625

<210> SEQ ID NO 6
<211> LENGTH: 1627
<212> TYPE: PRT
<213> ORGANISM: Lactobacillus helveticus

<400> SEQUENCE: 6

Met Leu Leu Val Phe Gln Lys Leu Gln Leu Trp Val Ala Ala Ile
1                5                  10                 15

Ile Ala Leu Ala Ser Gly Ser Thr Val Phe Leu Ser Gln Asn Thr Ala
             20                  25                 30

Glu Ala Ala Thr Asn Asp Pro Gly Ala Ser Asp Val Gln Val Lys Val
             35                  40                 45

Val Gln Gln Asp Gln Lys Gln Asp Gln Asn Ser Thr Ala Asn Ala Ala
        50                  55                 60

Val Ser Asn Ser Asp Ser Ala Lys Thr Gln Thr Asn Ala Thr Asp Gln
65                  70                  75                 80

Thr Gln Asn Ser Thr Val Val Ser Gly Asp Ser Thr Thr Ala Asn Ser
                85                  90                 95

Lys Thr Ser Gln Thr Ser Asn Ala Gln Thr Thr Ser Thr Thr Thr Asn
            100                 105                110

Ser Val Asp Pro Asn Gln Glu Gln Gln Pro Ala Asn Gln Ala Asp His
        115                 120                 125

Val Lys Gly Asn Val Gln Ser Ala Trp Asp Gln Gly Tyr Arg Gly Gln
    130                 135                 140

Gly Thr Val Val Ala Val Ile Asp Ser Gly Ala Asp Pro Thr His Lys
145                 150                 155                 160

Asp Phe Lys Thr Met Pro Glu Asp Pro Lys Leu Ser Glu Asp Asp Met
                165                 170                 175

Gln Ala Lys Ile Ala Lys Gln Gly Tyr Gly Lys Tyr Val Asn Glu Lys
            180                 185                 190

Phe Pro Tyr Val Tyr Asn Tyr Ala Asp Arg Asp Asn Asp Tyr Ile Thr
        195                 200                 205

Ser Asp Asp Thr Asn Ala Asn Asp Ser Pro His Gly Gln His Val Ser
    210                 215                 220

Gly Ile Ile Ala Ala Asp Gly Lys Pro Asp Gly Asn Lys Glu Tyr Val
225                 230                 235                 240

Val Gly Val Ala Pro Glu Ala Gln Leu Met Gln Leu Arg Val Phe Gly
                245                 250                 255

Gln Phe Ser Asp Glu Lys Thr Asp Asp Val Ala Lys Ala Ile Tyr Asp
            260                 265                 270

Ala Thr Asn Leu Gly Ala Asp Val Ile Gln Met Ser Leu Gly Gln Gly
        275                 280                 285

Val Ala Asp Gln Gln Leu Thr Asn Ile Glu Gln Lys Ala Val Gln Tyr
    290                 295                 300
```

-continued

```
Ala Ile Asp His Gly Val Phe Val Ser Ile Ser Ala Ser Asn Asn Gly
305                 310                 315                 320

Asn Ser Ala Ser Val Asp Asn Pro Ser Lys Val Lys Asp Gln Gly Tyr
            325                 330                 335

Gln Ser Gly Ser Gln Ala Gly Asn Tyr Glu Pro Leu Asn Leu Ser Thr
        340                 345                 350

Val Ala Asn Pro Gly Val Ser Lys Asn Ala Leu Thr Val Ala Ala Glu
    355                 360                 365

Thr Ser Asp Thr Gly Asp Leu Ser Asp Met Ala Tyr Phe Ser Ser Trp
370                 375                 380

Gly Pro Ala Gln Asp Tyr Thr Leu Lys Pro Asp Leu Ser Ala Pro Gly
385                 390                 395                 400

Tyr Gln Val Val Ser Thr Val Asn His Asp Gln Tyr Gln Thr Met Ser
            405                 410                 415

Gly Thr Ser Met Ala Gly Pro Phe Ala Ala Ser Ala Ala Leu Val
        420                 425                 430

Ile Gln Arg Leu Lys Gln Thr Asn Pro Glu Leu Lys Gly Ala Gln Leu
    435                 440                 445

Val Ala Ala Lys Ala Met Leu Met Asn Thr Ala Lys Pro Gln Thr
450                 455                 460

Gln Leu Gly Tyr Thr Thr Pro Val Ser Pro Arg Arg Gln Gly Ala Gly
465                 470                 475                 480

Gln Ile Asp Val Gly Ala Ala Thr Ala Thr Pro Val Tyr Val Thr Thr
            485                 490                 495

Asp Asp Gly Thr Ser Ser Val Ser Leu His Gln Val Gly Glu Ser Thr
        500                 505                 510

Lys Phe Thr Leu Thr Phe His Asn Leu Thr Asp Gln Ser Arg Thr Tyr
    515                 520                 525

Thr Phe Asp Asp Tyr Gly Gly Tyr Thr Glu Gln Arg Asp Thr Thr
530                 535                 540

Thr Gly Val Phe His Asp Val Gln Leu Ala Gly Ala Arg Val Asn Gly
545                 550                 555                 560

Glu His Ser Phe Thr Leu Ala Pro Lys Glu Glu Arg Gln Val Ser Tyr
            565                 570                 575

Ser Leu Asp Leu Thr Gly Leu Lys Lys Asn Gln Leu Val Glu Gly Phe
        580                 585                 590

Leu Arg Phe Thr Asn Ala Asn Asn Ala Ser Thr Val Ser Val Pro Tyr
    595                 600                 605

Leu Ala Tyr Tyr Gly Asp Leu Thr Ser Glu Asn Val Phe Asp Gln Asn
610                 615                 620

Ala Asn Glu Glu His Leu Asp Ile Gln Gly Asn Arg Leu Val Asn Glu
625                 630                 635                 640

Gln Asn Tyr Pro Arg Gly Ile Ala Asp Gln Glu Ser Leu Lys Glu Leu
            645                 650                 655

Val Asn Val Asp Gly Asn Tyr Asn Trp Gln Glu Val Ala Lys Leu Tyr
        660                 665                 670

Glu Ser Gly Lys Val Ala Phe Ser Pro Asn Asp Asn Gln Lys Ser Asp
    675                 680                 685

Leu Leu Lys Pro Tyr Val Tyr Leu Lys Gln Asn Val Lys Asp Leu Lys
690                 695                 700

Val Glu Ile Leu Asp Ala Gln Gly Asn Val Val Arg Val Val Ser Asp
705                 710                 715                 720
```

-continued

```
Val Gln Gly Val Asp Lys Ser Tyr Asp Glu Asn Gly Val Thr Lys Asp
            725                 730                 735

Thr Ser Leu Ser Val Ser Met Arg Asp Asn Pro Asp Ala Leu Glu Trp
            740                 745                 750

Asp Gly Lys Val Tyr Asn Ser Lys Thr Gly Lys Met Glu Thr Ala Lys
            755                 760                 765

Asp Gly Asn Tyr Thr Tyr Arg Leu Val Ala Thr Leu Trp Asn Lys Gly
770                 775                 780

Pro His Gln Val Gln Thr Ala Asp Phe Pro Val Val Asp Thr Val
785                 790                 795                 800

Ala Pro Thr Leu Ser Asn Val Lys Tyr Asp Ala Ala Ser His Thr Leu
                805                 810                 815

Ser Gly Glu Tyr Gln Asp Ala Gly Ala Gly Phe Thr Asn Tyr Ser Tyr
                820                 825                 830

Ala Thr Val Thr Val Asn Asp Lys Val Phe Gly Tyr Lys Leu Ser Asp
                835                 840                 845

Gly Gly Ser Gly Phe Asp Asn Ala Glu Lys Thr Lys Gly His Phe Ser
850                 855                 860

Phe Val Leu Gly Gln Asp Ala Leu Ser Ala Leu Thr Ala Ala Ala Asn
865                 870                 875                 880

Lys Val Thr Val Ala Leu Ser Asp Val Ala Asp Asn Thr Ser Leu Ala
                885                 890                 895

Thr Val Asn Val Ala Gly Asp His Asp Ser Glu Thr Gly Val Ser Val
                900                 905                 910

Trp Asn Ala Val Asn Gly Leu Ala Phe Asp Gln Lys Ser Pro Asn Tyr
            915                 920                 925

Asp Ala Ala Thr Lys Thr Tyr Thr Leu Val Gly Gly Ala Asn His Asp
930                 935                 940

Phe Tyr Leu Asn Gly Lys Leu Val Gln Val Gln Asp Gly Lys Tyr Gln
945                 950                 955                 960

Val Pro Val Ser Val Asn Thr Thr Lys Phe Val Phe Ser Thr Asp Pro
                965                 970                 975

Glu Gly Gln His Val Leu Lys Asp Leu Ser Thr Val Thr Ala Lys Ala
                980                 985                 990

Phe Phe Asn Trp Gln Lys Thr Asp Thr Phe Asp Gly Asn Phe Gly Val
            995                 1000                1005

Thr Ile Ser Ser Val Lys Thr Asn Asn Pro Asn Asp Thr Val Val
    1010                1015                1020

Gln Ala Val Val Thr Lys Gly Lys Asn Val Lys Ala Tyr Ala Met
    1025                1030                1035

Asp Tyr Phe Thr Gly Glu Val Tyr Thr Gly Glu Val Lys Asp Gly
    1040                1045                1050

Ile Ala Thr Phe His Val His Thr Ser Ile Asn Lys Asp Ala Thr
    1055                1060                1065

Thr Gly Val Tyr Arg Arg Ala Leu Leu Thr Gly Trp Thr Glu Val
    1070                1075                1080

Asp Gly Pro Ser Phe Asn Asp Lys Gln Glu Thr Ser Arg Asp Gly
    1085                1090                1095

Val Ser Ser Ser Asn His Leu Gly Val Phe Tyr Phe Ala Asp Ala
    1100                1105                1110

Ala Asn Arg Pro Val Tyr Thr Asp Arg Asn Ala Leu Gly Val Glu
    1115                1120                1125

Ala Lys Asp Glu Ala Ala Lys Leu Asp Ser Phe Cys Pro Gly Ala
```

-continued

```
         1130                1135                1140

Tyr Pro Gly His Ala Pro Ser Ala Leu Thr Thr Arg Thr Asp Pro
1145                1150                1155

Asn Pro Asp Ile His Phe Asp Tyr Met Asn Asp Asn Asp Thr Thr
1160                1165                1170

Arg Phe Gly Gln Asn Ala Val Thr His Gly Tyr Tyr Asp Pro Ser
1175                1180                1185

Thr Gln Lys Phe Thr Val Thr Gly Lys Val Asp Asp Asn Val Val
1190                1195                1200

Ser Leu Thr Val Leu Gly Asp Asn Ser Asn Glu Asn Ala Pro Glu
1205                1210                1215

Asn Gln Val Lys Leu Gly Asn Asp Gly Lys Phe Ser Phe Thr Val
1220                1225                1230

Thr Ala Asn Arg Thr Gly Gln Arg Pro Ile Ala Tyr Ile Tyr Lys
1235                1240                1245

Ala Lys Asp Gly Gln Arg Val Arg Gly Thr Leu Asn Leu Ile Leu
1250                1255                1260

Asp Thr Val Ala Pro Ser Leu Glu Val Asn Gln Val Asn Gly Asp
1265                1270                1275

Glu Leu Glu Leu Trp Thr Asn Asn Pro Lys Phe Thr Leu Ser Gly
1280                1285                1290

Lys Val Asn Asp Asn Leu Asp Gly Tyr Arg Leu Phe Val Asn Gly
1295                1300                1305

Asn Asn Ile Tyr Arg Glu Phe Leu Asn Ser Gly Tyr Asn Gln Val
1310                1315                1320

Ala Gly Leu Asn Thr Asp Thr Glu Phe Thr Asn Pro Tyr Gly Ala
1325                1330                1335

His Asp Phe Glu Glu Val Glu Asn Leu Asn Asp Asn Asn Asp Gln
1340                1345                1350

Pro Thr Thr His Val Phe Thr Val Tyr Val Val Asp Gln Val Gly
1355                1360                1365

Asn Lys Val Glu Lys Lys Leu Thr Val His Phe Asp Pro Asn Tyr
1370                1375                1380

Val Ala Pro Glu Glu Val Pro Asn Thr Asp Thr Ser Tyr Thr Leu
1385                1390                1395

Glu Asn Pro Leu Ser Thr Thr Thr Val Glu Asn Pro Val Thr Asp
1400                1405                1410

Val Ser Thr Val Gln Pro Lys Gly Glu Thr Leu Thr Gly Lys Ser
1415                1420                1425

Phe Asn Leu Leu His Asp Ala Tyr Ile Tyr Asn Lys Asp Gly Gln
1430                1435                1440

Val Val Leu Ser Thr Asp Thr Asn Lys Ser Ser Leu Leu Lys Lys
1445                1450                1455

Gly Gln Arg Ile Thr Ala Leu Asp Asn Gly Lys Thr Val Val Ile
1460                1465                1470

Asn Gly Val Gln Tyr Tyr Arg Val Gly Asp Asn Gln Phe Val Lys
1475                1480                1485

Val Thr Asn Thr Ile Leu Gln Ala Gly Lys Arg Leu Gln Leu Lys
1490                1495                1500

His Asn Ala His Leu Tyr Asp Lys Asn Gly Lys Val Val Lys Arg
1505                1510                1515

Asn Gly Lys Pro Val Leu Leu Arg Lys Gly Arg Trp Ile Ser Ala
1520                1525                1530
```

```
Leu Asn  Asn Ala Asp Lys Tyr  Val Ile Asn Gly Lys  Thr Phe Tyr
    1535             1540                 1545

Lys Leu  Ala Asn Gly Glu Phe  Val Lys Val Ala Asn  Thr Lys Leu
    1550             1555                 1560

Gln Lys  Pro Lys Ala Leu Lys  Leu Thr His Asn Ala  Phe Val Tyr
    1565             1570                 1575

Asp Glu  Asn Gly Lys Arg Val  Lys Lys Ser Lys Val  Leu Lys Lys
    1580             1585                 1590

Gly Gln  Thr Ile Leu Ala Glu  Asn Asn Ala Glu Lys  Phe His Ile
    1595             1600                 1605

Lys Gly  Lys Ala Tyr Tyr Lys  Val Asn Gly His Phe  Val Lys Val
    1610             1615                 1620

Ala Asn  Thr Leu
    1625
```

```
<210> SEQ ID NO 7
<211> LENGTH: 20
<212> TYPE: DNA
<213> ORGANISM: Artificial Sequence
<220> FEATURE:
<223> OTHER INFORMATION: PCR Primer

<400> SEQUENCE: 7
cgatgataat cctagcgagc                                         20

<210> SEQ ID NO 8
<211> LENGTH: 18
<212> TYPE: DNA
<213> ORGANISM: Artificial Sequence
<220> FEATURE:
<223> OTHER INFORMATION: PCR Primer

<400> SEQUENCE: 8
tggcagaacc tgtgccta                                           18

<210> SEQ ID NO 9
<211> LENGTH: 18
<212> TYPE: DNA
<213> ORGANISM: Artificial Sequence
<220> FEATURE:
<223> OTHER INFORMATION: PCR Primer

<400> SEQUENCE: 9
gccaagacgc ctctggta                                           18

<210> SEQ ID NO 10
<211> LENGTH: 21
<212> TYPE: DNA
<213> ORGANISM: Artificial Sequence
<220> FEATURE:
<223> OTHER INFORMATION: PCR Primer

<400> SEQUENCE: 10
taggtatagt ttccatcagg a                                       21

<210> SEQ ID NO 11
<211> LENGTH: 23
<212> TYPE: DNA
<213> ORGANISM: Artificial Sequence
<220> FEATURE:
<223> OTHER INFORMATION: PCR Primer

<400> SEQUENCE: 11
```

```
aargtwccwt ayggyywyaa yta                                              23

<210> SEQ ID NO 12
<211> LENGTH: 23
<212> TYPE: DNA
<213> ORGANISM: Artificial Sequence
<220> FEATURE:
<223> OTHER INFORMATION: PCR Primer

<400> SEQUENCE: 12
gccatdswdg trccdswcat dtk                                              23

<210> SEQ ID NO 13
<211> LENGTH: 30
<212> TYPE: DNA
<213> ORGANISM: Artificial Sequence
<220> FEATURE:
<223> OTHER INFORMATION: PCR Primer

<400> SEQUENCE: 13
cgaaggcgat aagtcaaact ttgataatgc                                       30

<210> SEQ ID NO 14
<211> LENGTH: 27
<212> TYPE: DNA
<213> ORGANISM: Artificial Sequence
<220> FEATURE:
<223> OTHER INFORMATION: PCR Primer

<400> SEQUENCE: 14
cccggttctg taagataatt tggatcg                                          27

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
astcwrrytt ygatratgcw                                                  20

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
bhkyamsawa rtttggatcr                                                  20

<210> SEQ ID NO 17
<211> LENGTH: 17
<212> TYPE: DNA
<213> ORGANISM: Artificial Sequence
<220> FEATURE:
<223> OTHER INFORMATION: PCR Primer

<400> SEQUENCE: 17
ggtgttgctc ctgaagc                                                     17

<210> SEQ ID NO 18
<211> LENGTH: 29
<212> TYPE: DNA
```

-continued

```
<213> ORGANISM: Artificial Sequence
<220> FEATURE:
<223> OTHER INFORMATION: PCR Primer

<400> SEQUENCE: 18
actctagcac cagctaattg aacatcatg                                    29

<210> SEQ ID NO 19
<211> LENGTH: 5358
<212> TYPE: DNA
<213> ORGANISM: Lactobacillus helveticus
<220> FEATURE:
<221> NAME/KEY: CDS
<222> LOCATION: (1)..(5358)
<223> OTHER INFORMATION:

<400> SEQUENCE: 19 atg aat aaa tct gat tta aaa gaa gcg aat cag ttt aaa tat gtc tac     48
Met Asn Lys Ser Asp Leu Lys Glu Ala Asn Gln Phe Lys Tyr Val Tyr
1               5                   10                  15 caa agt gga caa aag ctg aac gca gtc cac aat caa aaa agt tca cgc     96
Gln Ser Gly Gln Lys Leu Asn Ala Val His Asn Gln Lys Ser Ser Arg
            20                  25                  30 ttt tta agt aag tta cat aag aaa tgg gct gga gca aca att gtt gcc    144
Phe Leu Ser Lys Leu His Lys Lys Trp Ala Gly Ala Thr Ile Val Ala
        35                  40                  45 tta gct tca agt acc gtt ctc ttg ttc tca agt cat aat gtt aaa gct    192
Leu Ala Ser Ser Thr Val Leu Leu Phe Ser Ser His Asn Val Lys Ala
    50                  55                  60 gat gct caa gca cca agc gat gat aag caa cca gat cct gtt gta caa    240
Asp Ala Gln Ala Pro Ser Asp Asp Lys Gln Pro Asp Pro Val Val Gln
65                  70                  75                  80 aag agt gaa caa agt caa ggt caa act ttg caa gct gtt caa cgt aaa    288
Lys Ser Glu Gln Ser Gln Gly Gln Thr Leu Gln Ala Val Gln Arg Lys
                85                  90                  95 gac gat gca gta cca tct gat gca tac caa caa tct gca gct gta caa    336
Asp Asp Ala Val Pro Ser Asp Ala Tyr Gln Gln Ser Ala Ala Val Gln
            100                 105                 110 gct aat aac aat aat gat caa caa gct caa gac aat aaa caa gct agt    384
Ala Asn Asn Asn Asn Asp Gln Gln Ala Gln Asp Asn Lys Gln Ala Ser
        115                 120                 125 caa cca act agt cca gtg gca caa gct caa ccg gct caa caa caa aaa    432
Gln Pro Thr Ser Pro Val Ala Gln Ala Gln Pro Ala Gln Gln Gln Lys
    130                 135                 140 gca aag gat gtt gtt cca agt aag cca caa cct caa cca caa ccg gct    480
Ala Lys Asp Val Val Pro Ser Lys Pro Gln Pro Gln Pro Gln Pro Ala
145                 150                 155                 160 aag caa act act aat ggt caa act gaa gat gaa gat ggt caa aag gat    528
Lys Gln Thr Thr Asn Gly Gln Thr Glu Asp Glu Asp Gly Gln Lys Asp
                165                 170                 175 aag aat ggt gtt caa tta cca gct aat aat caa gac cat gta aaa ggt    576
Lys Asn Gly Val Gln Leu Pro Ala Asn Asn Gln Asp His Val Lys Gly
            180                 185                 190 aat gtt caa tcc gct tgg gat caa ggc tac cgc ggt gaa cat act gtt    624
Asn Val Gln Ser Ala Trp Asp Gln Gly Tyr Arg Gly Glu His Thr Val
        195                 200                 205 gta gca gtt att gac tct ggg gta gat gtt cat cat aaa gat ttc tta    672
Val Ala Val Ile Asp Ser Gly Val Asp Val His His Lys Asp Phe Leu
    210                 215                 220 acc atg cct aag aat cct aaa tta act gct gat caa atg aaa cgt ttg    720
Thr Met Pro Lys Asn Pro Lys Leu Thr Ala Asp Gln Met Lys Arg Leu
225                 230                 235                 240
```

```
att aag aga tta ggt tat ggt cgt tat gta aat gaa aaa ttc cca ttt        768
Ile Lys Arg Leu Gly Tyr Gly Arg Tyr Val Asn Glu Lys Phe Pro Phe
            245                 250                 255 gct tat aat tat gtt gat aat gaa aat gat cat tta aag gct cca aat        816
Ala Tyr Asn Tyr Val Asp Asn Glu Asn Asp His Leu Lys Ala Pro Asn
            260                 265                 270 ggt gag cct cac gga caa cac gtt tcc ggt att att gct gct gat ggt        864
Gly Glu Pro His Gly Gln His Val Ser Gly Ile Ile Ala Ala Asp Gly
            275                 280                 285 cat cca gat ggt gat aat act tat gtt gtg ggt gtt gct cct gaa gca        912
His Pro Asp Gly Asp Asn Thr Tyr Val Val Gly Val Ala Pro Glu Ala
    290                 295                 300 caa tta atg caa ttg aaa gta ttt ggc gat aac tca act tct ctt gat        960
Gln Leu Met Gln Leu Lys Val Phe Gly Asp Asn Ser Thr Ser Leu Asp
305                 310                 315                 320 atg gcc aaa gaa att tgc gat gct gtt aac ttg ggt gcc gat gtt atc       1008
Met Ala Lys Glu Ile Cys Asp Ala Val Asn Leu Gly Ala Asp Val Ile
                325                 330                 335 aat atg tca tta ggt ggt ggt gtt tct gct gct gac ctc aac att cag       1056
Asn Met Ser Leu Gly Gly Gly Val Ser Ala Ala Asp Leu Asn Ile Gln
                340                 345                 350 gat caa aga gca gtt caa tat gct gtt gat cat ggg gtt gtc gtt gtc       1104
Asp Gln Arg Ala Val Gln Tyr Ala Val Asp His Gly Val Val Val Val
                355                 360                 365 att tca gct gct aat aat ggt aat gca gct tct gtt gat aat cca act       1152
Ile Ser Ala Ala Asn Asn Gly Asn Ala Ala Ser Val Asp Asn Pro Thr
        370                 375                 380 cac tta aca gat tta gat aac tac caa gca ggt ggt aac gct ggt aac       1200
His Leu Thr Asp Leu Asp Asn Tyr Gln Ala Gly Gly Asn Ala Gly Asn
385                 390                 395                 400 tat aat cca ttt agt tca agt act gta gct aac cca ggt gct gcc aga       1248
Tyr Asn Pro Phe Ser Ser Ser Thr Val Ala Asn Pro Gly Ala Ala Arg
                405                 410                 415 agt gcg atc aca gta gca gct gaa act tct ggt act ggt aaa gat agc       1296
Ser Ala Ile Thr Val Ala Ala Glu Thr Ser Gly Thr Gly Lys Asp Ser
                420                 425                 430 gat atg gcc ttc ttt agt tct tgg ggt cca tta cct gat ttc act tta       1344
Asp Met Ala Phe Phe Ser Ser Trp Gly Pro Leu Pro Asp Phe Thr Leu
            435                 440                 445 aag cca gat gtt tcg gcc cca ggt tat gat gtc att tca acc gct aac       1392
Lys Pro Asp Val Ser Ala Pro Gly Tyr Asp Val Ile Ser Thr Ala Asn
        450                 455                 460 ggc aat tca tac acg caa atg agc ggt act tca atg gct agt cca ttc       1440
Gly Asn Ser Tyr Thr Gln Met Ser Gly Thr Ser Met Ala Ser Pro Phe
465                 470                 475                 480 gtg gct ggt gct gca gct ctt gtg aga gaa aga tta tta aag acc aat       1488
Val Ala Gly Ala Ala Ala Leu Val Arg Glu Arg Leu Leu Lys Thr Asn
                485                 490                 495 cct aag tta aag ggt gct gct tta gtt gaa gcc atc aaa gct ttg tta       1536
Pro Lys Leu Lys Gly Ala Ala Leu Val Glu Ala Ile Lys Ala Leu Leu
            500                 505                 510 act aat acg gct gat cca caa gtt caa aat ggc tac aac act ttg gtc       1584
Thr Asn Thr Ala Asp Pro Gln Val Gln Asn Gly Tyr Asn Thr Leu Val
        515                 520                 525 tca cca aga aga caa ggt gct ggt caa att aat gtt ggt gcc gca act       1632
Ser Pro Arg Arg Gln Gly Ala Gly Gln Ile Asn Val Gly Ala Ala Thr
530                 535                 540 aaa tct ccg gtt tat gtt act act gct gac gga act ggt gcc tta agc       1680
Lys Ser Pro Val Tyr Val Thr Thr Ala Asp Gly Thr Gly Ala Leu Ser
```

```
                   545                 550                 555                 560 tta cgc caa gtt ggc aat tcg acc act ttt gtc ttg aac ttg cat aac         1728
Leu Arg Gln Val Gly Asn Ser Thr Thr Phe Val Leu Asn Leu His Asn
                        565                 570                 575 tta tca aat gaa gaa caa gaa tat aat ttt gat gac ttc ggc ggt ggc         1776
Leu Ser Asn Glu Glu Gln Glu Tyr Asn Phe Asp Asp Phe Gly Gly Gly
                580                 585                 590 ttt act gaa ctt agg aat aag gct aac ggt gtc ttc cat gat gtt caa         1824
Phe Thr Glu Leu Arg Asn Lys Ala Asn Gly Val Phe His Asp Val Gln
            595                 600                 605 tta gct ggt gct aga gtt aac ggt gac aat gtt gtt gtc tta aag cca         1872
Leu Ala Gly Ala Arg Val Asn Gly Asp Asn Val Val Val Leu Lys Pro
        610                 615                 620 aat gaa act aaa caa gtt acc tat act ttg aat tta act agc att aaa         1920
Asn Glu Thr Lys Gln Val Thr Tyr Thr Leu Asn Leu Thr Ser Ile Lys
625                 630                 635                 640 aag aat caa tta gtt gaa ggt ttc ttg aga ttt act aac tcc aag gat         1968
Lys Asn Gln Leu Val Glu Gly Phe Leu Arg Phe Thr Asn Ser Lys Asp
                    645                 650                 655 aaa tca acc tta gtt gta cct tac ttg tca tac tat ggc gat atg act         2016
Lys Ser Thr Leu Val Val Pro Tyr Leu Ser Tyr Tyr Gly Asp Met Thr
                660                 665                 670 aag gaa aat gtc ttt gac caa aat gct aat gat cct aag cct gat att         2064
Lys Glu Asn Val Phe Asp Gln Asn Ala Asn Asp Pro Lys Pro Asp Ile
            675                 680                 685 caa ggt aat cgt tta gtt aac gaa gat aat tat cct cgt ggt att gct         2112
Gln Gly Asn Arg Leu Val Asn Glu Asp Asn Tyr Pro Arg Gly Ile Ala
        690                 695                 700 gac gaa aat tca tta aaa gaa tta gtc aat gtt gac ggt aat tat aac         2160
Asp Glu Asn Ser Leu Lys Glu Leu Val Asn Val Asp Gly Asn Tyr Asn
705                 710                 715                 720 tgg caa gaa gtt gct aag tta tat gag agt ggt aaa gtt gcc ttc tca         2208
Trp Gln Glu Val Ala Lys Leu Tyr Glu Ser Gly Lys Val Ala Phe Ser
                    725                 730                 735 cca aat ggt gat cat aag agt gac tta att aag cca tac gct tac ttg         2256
Pro Asn Gly Asp His Lys Ser Asp Leu Ile Lys Pro Tyr Ala Tyr Leu
                740                 745                 750 aaa caa aat gtc aag gac ttg aag gtt gag att ctt gat ggt tca ggt         2304
Lys Gln Asn Val Lys Asp Leu Lys Val Glu Ile Leu Asp Gly Ser Gly
            755                 760                 765 aaa gtt gtt cgt gtc ctt gct gat tct cgt ggc gtt gaa aag tca tac         2352
Lys Val Val Arg Val Leu Ala Asp Ser Arg Gly Val Glu Lys Ser Tyr
        770                 775                 780 cat tca gac ggt gat ggt gca aca gtt gac ctt gat aat ggt gca act         2400
His Ser Asp Gly Asp Gly Ala Thr Val Asp Leu Asp Asn Gly Ala Thr
785                 790                 795                 800 aac tct gat gtc ttc gac tgg gat ggt aaa tta tat gat gct aag act         2448
Asn Ser Asp Val Phe Asp Trp Asp Gly Lys Leu Tyr Asp Ala Lys Thr
                    805                 810                 815 ggt aag atg gtt gcc gct cca gat ggc aat tac act tac cgc ttc atc         2496
Gly Lys Met Val Ala Ala Pro Asp Gly Asn Tyr Thr Tyr Arg Phe Ile
                820                 825                 830 gca act ttg tat aac gat ggc cca caa aaa gtt caa act aat gat acc         2544
Ala Thr Leu Tyr Asn Asp Gly Pro Gln Lys Val Gln Thr Asn Asp Thr
            835                 840                 845 cca gtt atc atc gat acc act gct cct gtt tta agc gat gtt cac tac         2592
Pro Val Ile Ile Asp Thr Thr Ala Pro Val Leu Ser Asp Val His Tyr
        850                 855                 860 aac cgc aga agt aat aca att act ggt agt tac gct gat aag ggt gct         2640
```

```
Asn Arg Arg Ser Asn Thr Ile Thr Gly Ser Tyr Ala Asp Lys Gly Ala
865                 870                 875                 880 ggc ttt act gac tac tca tac gct aca gta act att aat gat cat gca         2688
Gly Phe Thr Asp Tyr Ser Tyr Ala Thr Val Thr Ile Asn Asp His Ala
                885                 890                 895 ttt ggt ttc aag ttg aat gat ggc aag aac tct ggt ttc gat gat gct         2736
Phe Gly Phe Lys Leu Asn Asp Gly Lys Asn Ser Gly Phe Asp Asp Ala
                900                 905                 910 aac aag aca aaa ggt cac ttc agt ttc aag tta act ggg gat gaa ctt         2784
Asn Lys Thr Lys Gly His Phe Ser Phe Lys Leu Thr Gly Asp Glu Leu
            915                 920                 925 aaa gca tta act agt gca gat aac cta gtt tca gta gct ttc agt gac         2832
Lys Ala Leu Thr Ser Ala Asp Asn Leu Val Ser Val Ala Phe Ser Asp
            930                 935                 940 gtt gca gat aac aca gtt gta aag agc ttg aaa ctt gat ggt agt ttt         2880
Val Ala Asp Asn Thr Val Val Lys Ser Leu Lys Leu Asp Gly Ser Phe
945                 950                 955                 960 gat caa cca ggc gtt tca att tgg aat gca act aat ggt tta cca ttt         2928
Asp Gln Pro Gly Val Ser Ile Trp Asn Ala Thr Asn Gly Leu Pro Phe
                965                 970                 975 aat gaa aac tca gct gac tat gac aag gct gct aac acc ttc aac tta         2976
Asn Glu Asn Ser Ala Asp Tyr Asp Lys Ala Ala Asn Thr Phe Asn Leu
                980                 985                 990 cgt ggt agt gct agt gat gac ttc    tac ctt aat ggt aag    tgg gtt caa   3024
Arg Gly Ser Ala Ser Asp Asp Phe    Tyr Leu Asn Gly Lys    Trp Val Gln
            995                    1000                1005 ctt gat    gac aat ggt caa ttc    gtt gtc cca gtt agt    gcg caa gga    3069
Leu Asp    Asp Asn Gly Gln Phe    Val Val Pro Val Ser    Ala Gln Gly
1010                   1015                           1020 gaa caa    gat tta gtc ttc agt    tct gat gat ggt ggt    aaa gat gtc    3114
Glu Gln    Asp Leu Val Phe Ser    Ser Asp Asp Gly Gly    Lys Asp Val
1025                   1030                           1035 ctt act    acc ttt aga aat tac    aca cca aag gct aaa    ttt gca tgg    3159
Leu Thr    Thr Phe Arg Asn Tyr    Thr Pro Lys Ala Lys    Phe Ala Trp
1040                   1045                           1050 caa cat    gta gat ggt caa gat    gaa cac ttt ggc cca    gca att tac    3204
Gln His    Val Asp Gly Gln Asp    Glu His Phe Gly Pro    Ala Ile Tyr
1055                   1060                           1065 tca atc    ttt ggt agt aac cca    gat gat att gtt gtt    caa gct gca    3249
Ser Ile    Phe Gly Ser Asn Pro    Asp Asp Ile Val Val    Gln Ala Ala
1070                   1075                           1080 gtt act    aag ggt gat aac gtt    aag gcc ttt gct aag    gat tac ttc    3294
Val Thr    Lys Gly Asp Asn Val    Lys Ala Phe Ala Lys    Asp Tyr Phe
1085                   1090                           1095 act ggt    caa att tat act ggt    gtt gta aaa gat ggg    gtt gcc aca    3339
Thr Gly    Gln Ile Tyr Thr Gly    Val Val Lys Asp Gly    Val Ala Thr
1100                   1105                           1110 ttc cac    gtt aag aca agt att    aac aaa gat cca aag    act aat atc    3384
Phe His    Val Lys Thr Ser Ile    Asn Lys Asp Pro Lys    Thr Asn Ile
1115                   1120                           1125 ttt gct    cgt gcc tta tta caa    ggt tgg act gaa gtt    gat gga cca    3429
Phe Ala    Arg Ala Leu Leu Gln    Gly Trp Thr Glu Val    Asp Gly Pro
1130                   1135                           1140 acc ttt    aat gat aag caa aag    act gat cca act gct    att aag gat    3474
Thr Phe    Asn Asp Lys Gln Lys    Thr Asp Pro Thr Ala    Ile Lys Asp
1145                   1150                           1155 gct aac    tac atc ggt gtc tac    tat gat aaa gat gct    gta gct cat    3519
Ala Asn    Tyr Ile Gly Val Tyr    Tyr Asp Lys Asp Ala    Val Ala His
1160                   1165                           1170
```

| | |
|---|---|
| gta tac act aat cgt gat gat tta ggt gta gta atg acg gat gaa<br>Val Tyr Thr Asn Arg Asp Asp Leu Gly Val Val Met Thr Asp Glu<br>1175                    1180                    1185 | 3564 |
| gtg gca gat cca aag gac ttc ggc cca ggt cta tat cca ggt cat<br>Val Ala Asp Pro Lys Asp Phe Gly Pro Gly Leu Tyr Pro Gly His<br>1190                    1195                    1200 | 3609 |
| tct gct cca agt gca cat aat cca cat atc aag ttt gat tac ttg<br>Ser Ala Pro Ser Ala His Asn Pro His Ile Lys Phe Asp Tyr Leu<br>1205                    1210                    1215 | 3654 |
| gat gat aat aat gta gct agt gtt ggt gca gaa gcc gtt aag aag<br>Asp Asp Asn Asn Val Ala Ser Val Gly Ala Glu Ala Val Lys Lys<br>1220                    1225                    1230 | 3699 |
| ggc tac tac aac cca aga aca cat gag ttt acg cta act ggc caa<br>Gly Tyr Tyr Asn Pro Arg Thr His Glu Phe Thr Leu Thr Gly Gln<br>1235                    1240                    1245 | 3744 |
| gtt gat gct aat gta atc agt tta acc ttc tta gca gct agt cca<br>Val Asp Ala Asn Val Ile Ser Leu Thr Phe Leu Ala Ala Ser Pro<br>1250                    1255                    1260 | 3789 |
| tat gaa gaa gct gca gaa aat caa gct gat att agc caa aat ggt<br>Tyr Glu Glu Ala Ala Glu Asn Gln Ala Asp Ile Ser Gln Asn Gly<br>1265                    1270                    1275 | 3834 |
| aag ttt aag ttt agc ttc aag att cca aat gct ggt aca aga gaa<br>Lys Phe Lys Phe Ser Phe Lys Ile Pro Asn Ala Gly Thr Arg Glu<br>1280                    1285                    1290 | 3879 |
| tta tca tac ttg tac atg act tct gac ggt aaa gta aca cgt ggt<br>Leu Ser Tyr Leu Tyr Met Thr Ser Asp Gly Lys Val Thr Arg Gly<br>1295                    1300                    1305 | 3924 |
| tct ttg aca ctt atc tta gat act gtt ttg cct act tta cat gtt<br>Ser Leu Thr Leu Ile Leu Asp Thr Val Leu Pro Thr Leu His Val<br>1310                    1315                    1320 | 3969 |
| gat caa atg cca gca aat cgt gca gaa gtt gaa tac act acc agc<br>Asp Gln Met Pro Ala Asn Arg Ala Glu Val Glu Tyr Thr Thr Ser<br>1325                    1330                    1335 | 4014 |
| aat cca acc ttt acc ctt tct ggt gta gct aat gat aac tta gat<br>Asn Pro Thr Phe Thr Leu Ser Gly Val Ala Asn Asp Asn Leu Asp<br>1340                    1345                    1350 | 4059 |
| gct tac agt gtc tac atc aat ggt gat aac gtc ttt agt caa ttt<br>Ala Tyr Ser Val Tyr Ile Asn Gly Asp Asn Val Phe Ser Gln Phe<br>1355                    1360                    1365 | 4104 |
| ggc aat tct ggc tac aac ttc att cca ggt ttg tac aat gat cca<br>Gly Asn Ser Gly Tyr Asn Phe Ile Pro Gly Leu Tyr Asn Asp Pro<br>1370                    1375                    1380 | 4149 |
| aag caa aag aca cct aat act tat ggt cca tat aac ttt aat gtt<br>Lys Gln Lys Thr Pro Asn Thr Tyr Gly Pro Tyr Asn Phe Asn Val<br>1385                    1390                    1395 | 4194 |
| aag gaa gct ttg gat gat gaa aat agt caa cca act act cac gtc<br>Lys Glu Ala Leu Asp Asp Glu Asn Ser Gln Pro Thr Thr His Val<br>1400                    1405                    1410 | 4239 |
| ttt gtt gtt gca att gtt gat gct gta ggg aac cgc gtt gaa aag<br>Phe Val Val Ala Ile Val Asp Ala Val Gly Asn Arg Val Glu Lys<br>1415                    1420                    1425 | 4284 |
| aga tta gtt gtt cac tat gat cca aac ttt ggt aag acc gca gct<br>Arg Leu Val Val His Tyr Asp Pro Asn Phe Gly Lys Thr Ala Ala<br>1430                    1435                    1440 | 4329 |
| aaa cca gaa gat aat aaa ggc gag ggt aat aaa caa caa tct act<br>Lys Pro Glu Asp Asn Lys Gly Glu Gly Asn Lys Gln Gln Ser Thr<br>1445                    1450                    1455 | 4374 |
| agt cct gct gaa cca gtg aag gta cca gct ggt caa tca agt cag<br>Ser Pro Ala Glu Pro Val Lys Val Pro Ala Gly Gln Ser Ser Gln<br>1460                    1465                    1470 | 4419 |

-continued

| | | |
|---|---|---|
| cca aaa caa cca act gct cca gtt caa tca tca act ggt aag aag<br>Pro Lys Gln Pro Thr Ala Pro Val Gln Ser Ser Thr Gly Lys Lys<br>1475                    1480                    1485 | 4464 |
| gaa gag agt agc aag cca gct gca act cca act aag cca gaa gca<br>Glu Glu Ser Ser Lys Pro Ala Ala Thr Pro Thr Lys Pro Glu Ala<br>1490                    1495                    1500 | 4509 |
| ggt aag gaa gta act cca gct aag cca agt aaa cca gaa aat gtt<br>Gly Lys Glu Val Thr Pro Ala Lys Pro Ser Lys Pro Glu Asn Val<br>1505                    1510                    1515 | 4554 |
| gct caa cca aca act ggt aag aag gaa gag agt agc aag cca gct<br>Ala Gln Pro Thr Thr Gly Lys Lys Glu Glu Ser Ser Lys Pro Ala<br>1520                    1525                    1530 | 4599 |
| gta act cca act aag cca gaa gga ggc aag gaa gta gcc cca gct<br>Val Thr Pro Thr Lys Pro Glu Gly Gly Lys Glu Val Ala Pro Ala<br>1535                    1540                    1545 | 4644 |
| aag cca agt aaa cca gcc agt gcc act caa cca aca act ggt aag<br>Lys Pro Ser Lys Pro Ala Ser Ala Thr Gln Pro Thr Thr Gly Lys<br>1550                    1555                    1560 | 4689 |
| aag gaa gaa agt ggc aag cca gcc gca act cca gct caa cca gct<br>Lys Glu Glu Ser Gly Lys Pro Ala Ala Thr Pro Ala Gln Pro Ala<br>1565                    1570                    1575 | 4734 |
| aag cca gca agt gaa aac aat caa gct agt caa gca act caa cct<br>Lys Pro Ala Ser Glu Asn Asn Gln Ala Ser Gln Ala Thr Gln Pro<br>1580                    1585                    1590 | 4779 |
| tca caa cct gca ggt caa ccg gtc gct gct aag aaa gat gaa agt<br>Ser Gln Pro Ala Gly Gln Pro Val Ala Ala Lys Lys Asp Glu Ser<br>1595                    1600                    1605 | 4824 |
| aac aaa caa gat act cct ctg aca aaa cca gct aat ggt tca caa<br>Asn Lys Gln Asp Thr Pro Leu Thr Lys Pro Ala Asn Gly Ser Gln<br>1610                    1615                    1620 | 4869 |
| tca gaa act tca aca tta tca act gct cca act gaa tca act aaa<br>Ser Glu Thr Ser Thr Leu Ser Thr Ala Pro Thr Glu Ser Thr Lys<br>1625                    1630                    1635 | 4914 |
| tca agt tca gaa aat aat aat tta cct tca tct cct gca caa agt<br>Ser Ser Ser Glu Asn Asn Asn Leu Pro Ser Ser Pro Ala Gln Ser<br>1640                    1645                    1650 | 4959 |
| aac gaa caa tca gtt gct ggt cct gtt aaa gct caa aag gtt gca<br>Asn Glu Gln Ser Val Ala Gly Pro Val Lys Ala Gln Lys Val Ala<br>1655                    1660                    1665 | 5004 |
| aga aga gct aaa caa gtt aag tta acc cgt aat gca cgt gca tat<br>Arg Arg Ala Lys Gln Val Lys Leu Thr Arg Asn Ala Arg Ala Tyr<br>1670                    1675                    1680 | 5049 |
| aat ctt aat ggg aaa tta gtc ctt aag aag ggt aaa gtt ctt act<br>Asn Leu Asn Gly Lys Leu Val Leu Lys Lys Gly Lys Val Leu Thr<br>1685                    1690                    1695 | 5094 |
| ctt aga aat aat ggc cgt gta gta act att aaa tgt cat aaa tat<br>Leu Arg Asn Asn Gly Arg Val Val Thr Ile Lys Cys His Lys Tyr<br>1700                    1705                    1710 | 5139 |
| tac cag gtt ggt aag aat gtt tac gtt gct gtt gcc aac act tta<br>Tyr Gln Val Gly Lys Asn Val Tyr Val Ala Val Ala Asn Thr Leu<br>1715                    1720                    1725 | 5184 |
| aag caa aga aca ttt aaa cat aat gtt gct gtt tat aac cat aaa<br>Lys Gln Arg Thr Phe Lys His Asn Val Ala Val Tyr Asn His Lys<br>1730                    1735                    1740 | 5229 |
| ggc aag aaa gtt ggt gtt ctt aaa gct ggc aga aaa gtt gtt tta<br>Gly Lys Lys Val Gly Val Leu Lys Ala Gly Arg Lys Val Val Leu<br>1745                    1750                    1755 | 5274 |
| tta aac aat ggt aga acg aca act att cat ggt aag aag ttt tat<br>Leu Asn Asn Gly Arg Thr Thr Thr Ile His Gly Lys Lys Phe Tyr | 5319 |

-continued

```
                                        1760                1765                1770
       caa  gtt  ggt  aag  gat  caa  ttt  gtt  aag  gct  agt  gat  ctt                    5358
       Gln  Val  Gly  Lys  Asp  Gln  Phe  Val  Lys  Ala  Ser  Asp  Leu
            1775                1780                1785
```

<210> SEQ ID NO 20
<211> LENGTH: 1786
<212> TYPE: PRT
<213> ORGANISM: Lactobacillus helveticus

<400> SEQUENCE: 20

```
Met Asn Lys Ser Asp Leu Lys Glu Ala Asn Gln Phe Lys Tyr Val Tyr
1               5                   10                  15

Gln Ser Gly Gln Lys Leu Asn Ala Val His Asn Gln Lys Ser Ser Arg
            20                  25                  30

Phe Leu Ser Lys Leu His Lys Lys Trp Ala Gly Ala Thr Ile Val Ala
        35                  40                  45

Leu Ala Ser Ser Thr Val Leu Leu Phe Ser Ser His Asn Val Lys Ala
    50                  55                  60

Asp Ala Gln Ala Pro Ser Asp Lys Gln Pro Asp Pro Val Val Gln
65                  70                  75                  80

Lys Ser Glu Gln Ser Gln Gly Gln Thr Leu Gln Ala Val Gln Arg Lys
                85                  90                  95

Asp Asp Ala Val Pro Ser Asp Ala Tyr Gln Gln Ser Ala Ala Val Gln
            100                 105                 110

Ala Asn Asn Asn Asp Gln Gln Ala Gln Asp Asn Lys Gln Ala Ser
        115                 120                 125

Gln Pro Thr Ser Pro Val Ala Gln Ala Gln Pro Ala Gln Gln Lys
    130                 135                 140

Ala Lys Asp Val Val Pro Ser Lys Pro Gln Pro Gln Pro Gln Pro Ala
145                 150                 155                 160

Lys Gln Thr Thr Asn Gly Gln Thr Glu Asp Glu Asp Gly Gln Lys Asp
                165                 170                 175

Lys Asn Gly Val Gln Leu Pro Ala Asn Asn Gln Asp His Val Lys Gly
            180                 185                 190

Asn Val Gln Ser Ala Trp Asp Gln Gly Tyr Arg Gly Glu His Thr Val
        195                 200                 205

Val Ala Val Ile Asp Ser Gly Val Asp Val His His Lys Asp Phe Leu
    210                 215                 220

Thr Met Pro Lys Asn Pro Lys Leu Thr Ala Asp Gln Met Lys Arg Leu
225                 230                 235                 240

Ile Lys Arg Leu Gly Tyr Gly Arg Tyr Val Asn Glu Lys Phe Pro Phe
                245                 250                 255

Ala Tyr Asn Tyr Val Asp Asn Glu Asn Asp His Leu Lys Ala Pro Asn
            260                 265                 270

Gly Glu Pro His Gly Gln His Val Ser Gly Ile Ile Ala Ala Asp Gly
        275                 280                 285

His Pro Asp Gly Asp Asn Thr Tyr Val Val Gly Val Ala Pro Glu Ala
    290                 295                 300

Gln Leu Met Gln Leu Lys Val Phe Gly Asp Asn Ser Thr Ser Leu Asp
305                 310                 315                 320

Met Ala Lys Glu Ile Cys Asp Ala Val Asn Leu Gly Ala Asp Val Ile
                325                 330                 335

Asn Met Ser Leu Gly Gly Gly Val Ser Ala Ala Asp Leu Asn Ile Gln
            340                 345                 350
```

-continued

```
Asp Gln Arg Ala Val Gln Tyr Ala Val Asp His Gly Val Val Val
        355                 360                 365
Ile Ser Ala Ala Asn Asn Gly Asn Ala Ala Ser Val Asp Asn Pro Thr
    370                 375                 380
His Leu Thr Asp Leu Asp Asn Tyr Gln Ala Gly Gly Asn Ala Gly Asn
385                 390                 395                 400
Tyr Asn Pro Phe Ser Ser Thr Val Ala Asn Pro Gly Ala Ala Arg
            405                 410                 415
Ser Ala Ile Thr Val Ala Ala Glu Thr Ser Gly Thr Gly Lys Asp Ser
        420                 425                 430
Asp Met Ala Phe Phe Ser Ser Trp Gly Pro Leu Pro Asp Phe Thr Leu
        435                 440                 445
Lys Pro Asp Val Ser Ala Pro Gly Tyr Asp Val Ile Ser Thr Ala Asn
        450                 455                 460
Gly Asn Ser Tyr Thr Gln Met Ser Gly Thr Ser Met Ala Ser Pro Phe
465                 470                 475                 480
Val Ala Gly Ala Ala Ala Leu Val Arg Glu Arg Leu Leu Lys Thr Asn
            485                 490                 495
Pro Lys Leu Lys Gly Ala Ala Leu Val Glu Ala Ile Lys Ala Leu Leu
        500                 505                 510
Thr Asn Thr Ala Asp Pro Gln Val Gln Asn Gly Tyr Asn Thr Leu Val
        515                 520                 525
Ser Pro Arg Arg Gln Gly Ala Gly Gln Ile Asn Val Gly Ala Ala Thr
        530                 535                 540
Lys Ser Pro Val Tyr Val Thr Thr Ala Asp Gly Thr Gly Ala Leu Ser
545                 550                 555                 560
Leu Arg Gln Val Gly Asn Ser Thr Thr Phe Val Leu Asn Leu His Asn
            565                 570                 575
Leu Ser Asn Glu Glu Gln Glu Tyr Asn Phe Asp Asp Phe Gly Gly Gly
        580                 585                 590
Phe Thr Glu Leu Arg Asn Lys Ala Asn Gly Val Phe His Asp Val Gln
        595                 600                 605
Leu Ala Gly Ala Arg Val Asn Gly Asp Asn Val Val Leu Lys Pro
        610                 615                 620
Asn Glu Thr Lys Gln Val Thr Tyr Thr Leu Asn Leu Thr Ser Ile Lys
625                 630                 635                 640
Lys Asn Gln Leu Val Glu Gly Phe Leu Arg Phe Thr Asn Ser Lys Asp
            645                 650                 655
Lys Ser Thr Leu Val Val Pro Tyr Leu Ser Tyr Tyr Gly Asp Met Thr
        660                 665                 670
Lys Glu Asn Val Phe Asp Gln Asn Ala Asn Asp Pro Lys Pro Asp Ile
        675                 680                 685
Gln Gly Asn Arg Leu Val Asn Glu Asp Asn Tyr Pro Arg Gly Ile Ala
        690                 695                 700
Asp Glu Asn Ser Leu Lys Glu Leu Val Asn Val Asp Gly Asn Tyr Asn
705                 710                 715                 720
Trp Gln Glu Val Ala Lys Leu Tyr Glu Ser Gly Lys Val Ala Phe Ser
            725                 730                 735
Pro Asn Gly Asp His Lys Ser Asp Leu Ile Lys Pro Tyr Ala Tyr Leu
        740                 745                 750
Lys Gln Asn Val Lys Asp Leu Lys Val Glu Ile Leu Asp Gly Ser Gly
        755                 760                 765
```

```
Lys Val Val Arg Val Leu Ala Asp Ser Arg Gly Val Glu Lys Ser Tyr
770                 775                 780

His Ser Asp Gly Asp Gly Ala Thr Val Asp Leu Asp Asn Gly Ala Thr
785                 790                 795                 800

Asn Ser Asp Val Phe Asp Trp Asp Gly Lys Leu Tyr Asp Ala Lys Thr
            805                 810                 815

Gly Lys Met Val Ala Ala Pro Asp Gly Asn Tyr Thr Tyr Arg Phe Ile
        820                 825                 830

Ala Thr Leu Tyr Asn Asp Gly Pro Gln Lys Val Gln Thr Asn Asp Thr
    835                 840                 845

Pro Val Ile Ile Asp Thr Thr Ala Pro Val Leu Ser Asp Val His Tyr
850                 855                 860

Asn Arg Arg Ser Asn Thr Ile Thr Gly Ser Tyr Ala Asp Lys Gly Ala
865                 870                 875                 880

Gly Phe Thr Asp Tyr Ser Tyr Ala Thr Val Thr Ile Asn Asp His Ala
            885                 890                 895

Phe Gly Phe Lys Leu Asn Asp Gly Lys Asn Ser Gly Phe Asp Asp Ala
        900                 905                 910

Asn Lys Thr Lys Gly His Phe Ser Phe Lys Leu Thr Gly Asp Glu Leu
    915                 920                 925

Lys Ala Leu Thr Ser Ala Asp Asn Leu Val Ser Val Ala Phe Ser Asp
930                 935                 940

Val Ala Asp Asn Thr Val Val Lys Ser Leu Lys Leu Asp Gly Ser Phe
945                 950                 955                 960

Asp Gln Pro Gly Val Ser Ile Trp Asn Ala Thr Asn Gly Leu Pro Phe
            965                 970                 975

Asn Glu Asn Ser Ala Asp Tyr Asp Lys Ala Ala Asn Thr Phe Asn Leu
        980                 985                 990

Arg Gly Ser Ala Ser Asp Asp Phe Tyr Leu Asn Gly Lys Trp Val Gln
    995                 1000                1005

Leu Asp Asp Asn Gly Gln Phe Val Val Pro Val Ser Ala Gln Gly
1010                1015                1020

Glu Gln Asp Leu Val Phe Ser Ser Asp Gly Gly Lys Asp Val
1025                1030                1035

Leu Thr Thr Phe Arg Asn Tyr Thr Pro Lys Ala Lys Phe Ala Trp
1040                1045                1050

Gln His Val Asp Gly Gln Asp Glu His Phe Gly Pro Ala Ile Tyr
1055                1060                1065

Ser Ile Phe Gly Ser Asn Pro Asp Asp Ile Val Gln Ala Ala
1070                1075                1080

Val Thr Lys Gly Asp Asn Val Lys Ala Phe Ala Lys Asp Tyr Phe
1085                1090                1095

Thr Gly Gln Ile Tyr Thr Gly Val Val Lys Asp Gly Val Ala Thr
1100                1105                1110

Phe His Val Lys Thr Ser Ile Asn Lys Asp Pro Lys Thr Asn Ile
1115                1120                1125

Phe Ala Arg Ala Leu Leu Gln Gly Trp Thr Glu Val Asp Gly Pro
1130                1135                1140

Thr Phe Asn Asp Lys Gln Lys Thr Asp Pro Thr Ala Ile Lys Asp
1145                1150                1155

Ala Asn Tyr Ile Gly Val Tyr Tyr Asp Lys Asp Ala Val Ala His
1160                1165                1170

Val Tyr Thr Asn Arg Asp Asp Leu Gly Val Val Met Thr Asp Glu
```

-continued

```
            1175                1180                1185

Val Ala Asp Pro Lys Asp Phe Gly Pro Gly Leu Tyr Pro Gly His
    1190                1195                1200

Ser Ala Pro Ser Ala His Asn Pro His Ile Lys Phe Asp Tyr Leu
    1205                1210                1215

Asp Asp Asn Asn Val Ala Ser Val Gly Ala Glu Ala Val Lys Lys
    1220                1225                1230

Gly Tyr Tyr Asn Pro Arg Thr His Glu Phe Thr Leu Thr Gly Gln
    1235                1240                1245

Val Asp Ala Asn Val Ile Ser Leu Thr Phe Leu Ala Ala Ser Pro
    1250                1255                1260

Tyr Glu Glu Ala Ala Glu Asn Gln Ala Asp Ile Ser Gln Asn Gly
    1265                1270                1275

Lys Phe Lys Phe Ser Phe Lys Ile Pro Asn Ala Gly Thr Arg Glu
    1280                1285                1290

Leu Ser Tyr Leu Tyr Met Thr Ser Asp Gly Lys Val Thr Arg Gly
    1295                1300                1305

Ser Leu Thr Leu Ile Leu Asp Thr Val Leu Pro Thr Leu His Val
    1310                1315                1320

Asp Gln Met Pro Ala Asn Arg Ala Glu Val Glu Tyr Thr Thr Ser
    1325                1330                1335

Asn Pro Thr Phe Thr Leu Ser Gly Val Ala Asn Asp Asn Leu Asp
    1340                1345                1350

Ala Tyr Ser Val Tyr Ile Asn Gly Asp Asn Val Phe Ser Gln Phe
    1355                1360                1365

Gly Asn Ser Gly Tyr Asn Phe Ile Pro Gly Leu Tyr Asn Asp Pro
    1370                1375                1380

Lys Gln Lys Thr Pro Asn Thr Tyr Gly Pro Tyr Asn Phe Asn Val
    1385                1390                1395

Lys Glu Ala Leu Asp Asp Glu Asn Ser Gln Pro Thr Thr His Val
    1400                1405                1410

Phe Val Val Ala Ile Val Asp Ala Val Gly Asn Arg Val Glu Lys
    1415                1420                1425

Arg Leu Val Val His Tyr Asp Pro Asn Phe Gly Lys Thr Ala Ala
    1430                1435                1440

Lys Pro Glu Asp Asn Lys Gly Glu Gly Asn Lys Gln Gln Ser Thr
    1445                1450                1455

Ser Pro Ala Glu Pro Val Lys Val Pro Ala Gly Gln Ser Ser Gln
    1460                1465                1470

Pro Lys Gln Pro Thr Ala Pro Val Gln Ser Ser Thr Gly Lys Lys
    1475                1480                1485

Glu Glu Ser Ser Lys Pro Ala Ala Thr Pro Thr Lys Pro Glu Ala
    1490                1495                1500

Gly Lys Glu Val Thr Pro Ala Lys Pro Ser Lys Pro Glu Asn Val
    1505                1510                1515

Ala Gln Pro Thr Thr Gly Lys Lys Glu Glu Ser Ser Lys Pro Ala
    1520                1525                1530

Val Thr Pro Thr Lys Pro Glu Gly Gly Lys Glu Val Ala Pro Ala
    1535                1540                1545

Lys Pro Ser Lys Pro Ala Ser Ala Thr Gln Pro Thr Thr Gly Lys
    1550                1555                1560

Lys Glu Glu Ser Gly Lys Pro Ala Ala Thr Pro Ala Gln Pro Ala
    1565                1570                1575
```

-continued

```
Lys Pro Ala Ser Glu Asn Asn Gln Ala Ser Gln Ala Thr Gln Pro
    1580                1585                1590

Ser Gln Pro Ala Gly Gln Pro Val Ala Ala Lys Lys Asp Glu Ser
    1595                1600                1605

Asn Lys Gln Asp Thr Pro Leu Thr Lys Pro Ala Asn Gly Ser Gln
    1610                1615                1620

Ser Glu Thr Ser Thr Leu Ser Thr Ala Pro Thr Glu Ser Thr Lys
    1625                1630                1635

Ser Ser Ser Glu Asn Asn Asn Leu Pro Ser Ser Pro Ala Gln Ser
    1640                1645                1650

Asn Glu Gln Ser Val Ala Gly Pro Val Lys Ala Gln Lys Val Ala
    1655                1660                1665

Arg Arg Ala Lys Gln Val Lys Leu Thr Arg Asn Ala Arg Ala Tyr
    1670                1675                1680

Asn Leu Asn Gly Lys Leu Val Leu Lys Lys Gly Lys Val Leu Thr
    1685                1690                1695

Leu Arg Asn Asn Gly Arg Val Val Thr Ile Lys Cys His Lys Tyr
    1700                1705                1710

Tyr Gln Val Gly Lys Asn Val Tyr Val Ala Val Ala Asn Thr Leu
    1715                1720                1725

Lys Gln Arg Thr Phe Lys His Asn Val Ala Val Tyr Asn His Lys
    1730                1735                1740

Gly Lys Lys Val Gly Val Leu Lys Ala Gly Arg Lys Val Val Leu
    1745                1750                1755

Leu Asn Asn Gly Arg Thr Thr Thr Ile His Gly Lys Lys Phe Tyr
    1760                1765                1770

Gln Val Gly Lys Asp Gln Phe Val Lys Ala Ser Asp Leu
    1775                1780                1785
```